US008901097B2

(12) United States Patent
Feinstein et al.

(10) Patent No.: US 8,901,097 B2
(45) Date of Patent: Dec. 2, 2014

(54) METHODS FOR DELIVERY OF SIRNA TO THE SPINAL CORD AND THERAPIES ARISING THEREFROM

(75) Inventors: Elena Feinstein, Rehovot (IL); Martin Grumet, New York, NY (US)

(73) Assignees: Quark Pharmaceuticals, Inc., Fremont, CA (US); Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/508,493

(22) PCT Filed: Nov. 8, 2010

(86) PCT No.: PCT/US2010/055759
§ 371 (c)(1),
(2), (4) Date: Jun. 7, 2012

(87) PCT Pub. No.: WO2011/057171
PCT Pub. Date: May 12, 2011

(65) Prior Publication Data
US 2012/0252874 A1     Oct. 4, 2012

Related U.S. Application Data

(60) Provisional application No. 61/259,173, filed on Nov. 8, 2009.

(51) Int. Cl.
*C12N 15/11*      (2006.01)
*G01N 33/00*      (2006.01)
*C12N 15/113*     (2010.01)

(52) U.S. Cl.
CPC .......... *C12N 15/111* (2013.01); *C12N 2310/14* (2013.01); *C12N 2320/32* (2013.01); *C12N 15/1135* (2013.01); *C12N 15/1138* (2013.01)
USPC .......................................... 514/44 A; 436/94

(58) Field of Classification Search
None
See application file for complete search history.

(56) References Cited

U.S. PATENT DOCUMENTS

| 5,945,290 | A  | 8/1999  | Cowsert |
| 6,506,559 | B1 | 1/2003  | Fire et al. |
| 7,056,704 | B2 | 6/2006  | Tuschl et al. |
| 7,078,196 | B2 | 7/2006  | Tuschl et al. |
| 7,452,987 | B2 | 11/2008 | Giese et al. |
| 7,772,200 | B2 | 8/2010  | Soutschek et al. |
| 7,829,693 | B2 | 11/2010 | Kreutzer et al. |
| 7,888,325 | B2 | 2/2011  | Li et al. |
| 7,893,245 | B2 | 2/2011  | Giese et al. |
| 7,943,588 | B2 | 5/2011  | DeLeo et al. |
| 7,943,755 | B2 | 5/2011  | Ahmed |
| 8,097,710 | B2 | 1/2012  | Baulcombe et al. |
| 2003/0355820 |  | 1/2003 | Brown et al. |
| 2003/0027783 | A1 | 2/2003 | Zernicka-Goetz et al. |
| 2003/0108923 | A1 | 6/2003 | Tuschl et al. |
| 2004/0191291 | A1 | 9/2004 | Tohyama et al. |
| 2004/0192626 | A1 | 9/2004 | McSwiggen et al. |
| 2004/0229266 | A1 | 11/2004 | Tuschl et al. |
| 2004/0265839 | A1 | 12/2004 | Mello et al. |
| 2005/0020525 | A1 | 1/2005 | McSwiggen et al. |
| 2005/0037988 | A1 | 2/2005 | Zamore et al. |
| 2005/0181382 | A1 | 8/2005 | Zamore et al. |
| 2005/0209147 | A1 | 9/2005 | Laudanna |
| 2005/0223427 | A1 | 10/2005 | Leake et al. |
| 2005/0255487 | A1 | 11/2005 | Khvorova et al. |
| 2007/0031844 | A1 | 2/2007 | Khvorova et al. |
| 2007/0032441 | A1 | 2/2007 | McSwiggen et al. |
| 2007/0042984 | A1* | 2/2007 | Soutschek et al. ............... 514/44 |
| 2007/0244066 | A1* | 10/2007 | DeLeo et al. .................... 514/44 |
| 2009/0162365 | A1 | 6/2009 | Feinstein et al. |
| 2009/0221521 | A1 | 9/2009 | Hurtt |
| 2011/0112168 | A1 | 5/2011 | Feinstein et al. |

OTHER PUBLICATIONS

WO 2008050329 A2, Feinstein et al, May 2008, partial document of pp. 1-85 and 1178-1186 (95 pages total).*
Fougerolles et al., Interfering with disease: a progress report on siRNA-based therapeutics, Jun. 2007, Nature Reviews, 6: 443-453.*
Inoue et al, Initiation of neuropathic pain requires lysophosphatidic acid receptor signaling, 2004, vol. 10, 7: 712-718.*
International Preliminary Report on Patentability (Chapter I of the Patent Cooperation Treaty), including Written Opinion of the International Searching Authority, issued May 8, 2012 in connection with PCT International Application No. PCT/US2010/055759, filed Nov. 8, 2010.
Amarzguioui et al., (2003) "Tolerance for Mutations and Chemical Modifications in a siRNA." Nucl Acids Res. 31(2):589-95.
Barik, (2005) "Silence of the transcripts; RNA Interference in Medicine" Mol. Med 2005, 83:764-773.
Beattie et al., (2000) "Review of current evidence for apoptosis after spinal cord injury" J Neurotrauma. 17:915-25.
Bettoni et al., (2008) Glial TLR4 receptor as new target to treat neuropathic pain: efficacy of a new receptor antagonist in a model of peripheral nerve injury in mice. Glia. 56(12):1312-9.
Braash et al., (2003) "RNA Interference in Mammalian Cells by Chemically-Modified RNA." Biochemistry, 42:7967-7975.
Caplen et al., (2001) "Specific Inhibition of Gene Expression by Small Double-Stranded RNAs in Invertebrate Vertebrate Systems" Proc Nati Acad Sci, 98(17):9742-9747.
Chakraborty, (2007) "Potentiality of Small Interfering RNAs-(siRNA)as Recent Therapeutic Targets for Gene-Silencing" Current Drug Targets, 8(3):469-82.
Chiu & Rana, (2003) "SiRNA Function in RNAi: a Chemical Modification Analysis". RNA. 9:1034-1048.
Chiu & Rana (2002) "RNAi in Human Cells: basic Structural and Function Features of Small Interfering RNA" Mol Cell, 19:549-561.
Christoph et al., (2006) "Silencing of vanilloid receptor TRPV1 by RNAi reduces neuropathic and visceral pain in vivo." Biochem Biophys Res Commun. 350:238-43.

(Continued)

*Primary Examiner* — Tracy Vivlemore
*Assistant Examiner* — Kate Poliakova-Georgantas
(74) *Attorney, Agent, or Firm* — JMB Davis Ben-David

(57) ABSTRACT

The present application relates at least in part to methods for the administration of small interfering RNAs (siRNAs) to the spinal cord of a human or animal patient and also to a method of treatment for spinal cord injury and other diseases and disorders of the CNS. In particular, the application discloses methods to deliver an siRNA compound locally, directly and without the need for transduction vehicles and formulations in effective doses to the injured spinal cord to promote recovery of CNS function and or attenuation of allodynia.

14 Claims, 14 Drawing Sheets

(56) References Cited

OTHER PUBLICATIONS

Conrad et al., (2005) "Prolonged lesional expression of RhoA and RhoB following spinal cord injury." J Comp Neurol 487(2): 166-75.
Czauderna et al., (2003) "Structural Variations and Stabilising Modifications of Synthetic siRNAs in Mammalian Cells." Nucl Acids Res, 31(11):2705-16.
Dorn et al. (2004) "siRNA relieves chronic neuropathic pain" Nucl. Acids Res 32(5):e49.
Dubreuil et al., (2003) "Rho activation patterns after spinal cord injury and the role of activated Rho in apoptosis in the central nervous system." J Cell Biol. 162:233-43.
Elbashir et al., (2001) "Functional Anatomy of siRNAs for Mediating Efficient RNAi in Drosophila Melanogaster Embryo Lysate." EMBO Journal, 20(23):6877-88.
Elbashir et al., (2001) "RNA Interference is Mediated by 21- and 22-nucleotide RNAs" Genes Dev. 15:188-200.
Elbashir et al., (2001) "Duplexes of 21-nucleotide Mediated RNA Interference in Cultured Mammalian Cells" Nature 411:494-498.
Erschsamer et al., (2005) "RhoA, RhoB, RhoC, Rac1, Cdc42, and Tc10 mRNA levels in spinal cord, sensory ganglia, and corticospinal tract neurons and long-lasting specific changes following spinal cord injury." J Comp Neurol. 484:224-33.
Fu et al., (2007) "Nonsteroidal anti-inflammatory drugs promote axon regeneration via RhoA inhibition." J Neurosci. 27:4154-64.
Fire et al., (1998) "Potent and Specific Genetic Interference by Double-Stranded RNA in *Caenorhabditis Elegans*." Nature 391:806-811.
Holen et al., (2002) "Positional Effects of Short Interfering siRNAs targeting the human coagulation trigger Tissue Factor." Nucl. Acids Res. 30(8):1757-1766.
Lord-Fontaine et al., (2008) "Local inhibition of Rho signaling by cell-permeable recombinant protein BA-210 prevents secondary damage and promotes functional recovery following acute spinal cord injury." J Neurotrauma. 25:1309-22.
Luo, et al., (2005) "An efficient intrathecal delivery of small interfering RNA to the spinal cord and peripheral neurons." Mol Pain. 1:29.
Mahato et al., (2005) "Modulation of Gene Expression by Antisense and Antigene Oligodeoxynucleotides and Small Interfering RNA." Expert Opinion on Drug Delivery 2(1):3-28.
McManus et al., (2002) "Gene Silencing in Mammals by Small Interfering RNAs" Nature Reviews Genetics, vol. 3:737-747.
Otsuka et al., (2011) "Delayed intrathecal delivery of RhoA siRNA to the contused spinal cord inhibits allodynia, preserves white matter, and increases serotonergic fiber growth". J. Neurotrauma. 28(6):1063-76.
Pixley et al., (2005) "BCL6 suppresses RhoA activity to alter macrophage morphology and motility." J Cell Sci. 118:1873-83.
Prakash et al., (2005) "Positional effect of chemical modifications on short interference RNA activity in mammalian cells.", J. Med Chem. :48(13) pp. 4247-4253.
Rohl & Kurreck (2006) "RNA interference in pain research." J. Neurochem. 99:371-380.
Scherer and Rossi (2004) "Therapeutic Applications of RNA Interferences: Recent Advances in siRNA Design." Advances in Genetics 22:1-21.
Schreibelt et al., (2007) "Reactive oxygen species alter brain endothelial tight junction dynamics via RhoA, PI3 kinase, and PKB signaling." FASEB J. Nov. 2007;21(13):3666-76.
Schwab et al., (2004) "Lesional RhoA+ cell numbers are suppressed by anti-inflammatory, cyclooxygenase-inhibiting treatment following subacute spinal cord injury." Glia. 47:377-86.

Sioud et al., (2004) "Potential Design Rules and Enzymatic Synthesis of siRNAs" Methods in Molec Biol. 252:457-468.
Sung et al., (2003) "A possible role of RhoA/Rho-kinase in experimental spinal cord injury in rat." Brain Res 959(1):29-38.
Thakker et al., (2004) "Neurochemical and behavioral consequences of widespread gene knockdown in the adult mouse brain by using nonviral RNA interference" Proc Nati Acad Sci USA. 101:17270-5.
Ui Tei et al, (2008) "Functional dissection of siRNA Sequence by Systematic DNA Substitution: Modified si RNA with aDNA Seed Arm is a powerful Tool for Mammalian Gene Silencing with significantly reduced off-target effect", Nucl Acids Res, 36(7):2136-51.
Ui-Tei et al., (2006) "Essential notes regarding the design of functional siRNAs for efficient mammalian RNAi", J. Biomed Biotechnol, 2006:65052.
Ui-Tei et al., (2008) "DNA-modified siRNA dependent gene silencing with reduced off target effect is induced through a pathway parallel to that for siRNA-mediated RNA interference". Proc 2008 Micro-NanoMechatronics and Human Science (MHS2008) 339-345.
Wang et al., (2008) "Therapeutic Gene Silencing Delivered by a Chemically Modified Small Interfering RNA against Mutant SOD1 Slows Amyotrophic Lateral Sclerosis Progression" J Biol Chem. 283:15845-52.
Wu, et al. (2010) Intrathecal siRNA against Toll-like receptor 4 reduces nociception in a rat model of neuropathic pain. Int. J. Med. Sci. 7(5):251-259.
Yune et al., (2007) "Minocycline alleviates death of oligodendrocytes by inhibiting pro-nerve growth factor production in microglia after spinal cord injury." J Neurosci. 27(29):7751-61.
International Search Report, mailed Jan. 19, 2011 in connection with PCT International Application No. PCT/US2010/055759, filed Nov. 8, 2010.
Inoue et al. (2006). Loss of spinal substance P pain transmission under the condition of $LPA_1$ receptor-mediated neuropathic pain. *Molecular Pain*, 2(25), 1-5.
English translation of Search Report dated Jan. 28, 2013 issued in connection with Chinese Application No. 2010800528205.
English translation of Office Action dated Feb. 5, 2013, issued in connection with Chinese Application No. 2010800528205.
Inoue, et al., (2006) "Loss of spinal substance P pain transmission under the condition of LPA1 receptor-mediated neuropathic pain" Molecular Pain 2(25):1-5.
Ishida et al., "Botulinum Toxin Type A Targets RhoB to Inhibit Lysophosphatidic Acid-Stimulated Actin Reorganization and Acetylcholine Release in Nerve Growth Factor-Treated PC12 Cells", The Journal of Pharmacology and Experimental Therapeutics, , vol. 310: 881-889, 2004.
Baastrup C, Finnerup NB. (2008) CNS drugs vol. 22(6), pp. 455-475. Abstract.
Mann R. et al. (2013) Burden of spinal cord injury-related neuropathic pain in the United States: retrospective chart review and cross-sectional survey. Spinal Cord, vol. 51, pp. 564-570.
DeFrates S., Cook AM. (2011). Pharmacologic Treatment of Neuropathic Pain Following Spinal Cord Injury. Orthopedics, vol. 34, issue 3, pp. 203-207.
Neuropathic Pain Management. http://www.webmd.com/pain-management/guide/neuropathic-pain , 2013.
Neuropathic Pain. http://www.patient.co.uk/health/neuropathic-pain, 2013.

\* cited by examiner

FIGURE 1A
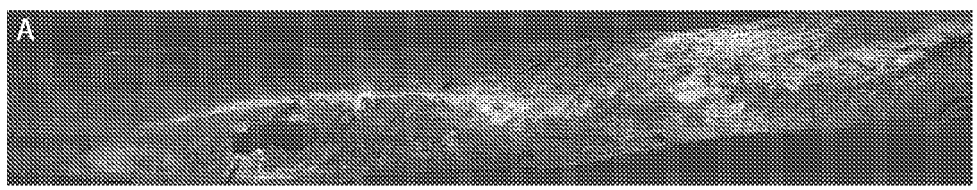
FIGURE 1B             FIGURE 1C             FIGURE 1D             FIGURE 1E
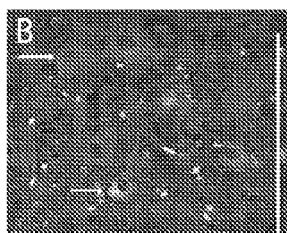 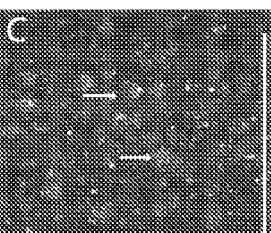 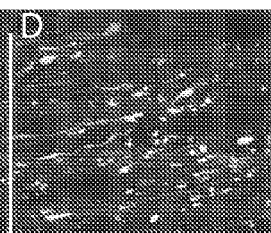 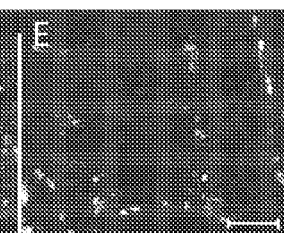
FIGURE 1F
| Days post injection | Motorneurons | Macrophages | Axons | Endothelial cells |
|---|---|---|---|---|
| 1   (n=3) | +++ | + | ++++ | ++++ |
| 3   (n=3) | ++ | +++ | ++++ | +++ |
| 7   (n=1) | ++++ | + | + | +++ |
| 14  (n=3) | +++ | + | + | +++ |

| FIGURE 6B | FIGURE 6C | FIGURE 6D |
|---|---|---|
| Cervical level | Proximal site (P) | Injury site (I) |

| FIGURE 6E | FIGURE 6F | FIGURE 6G |
|---|---|---|
| Distal-1 site (D1) | Distal-2 site (D2) | Distal-5 site (D5) |

FIGURE 12A    FIGURE 12B
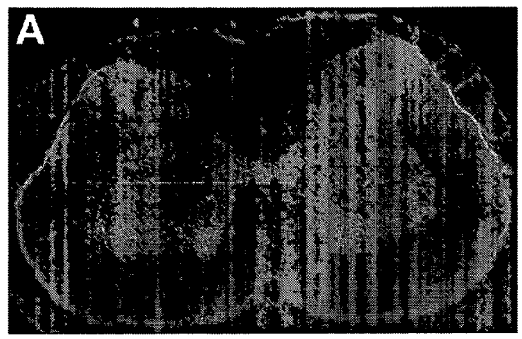 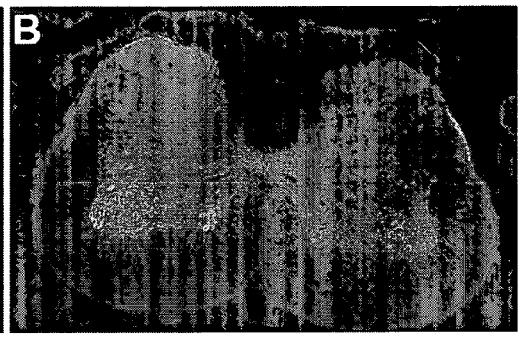
FIGURE 12C    FIGURE 12D
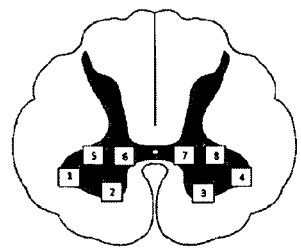 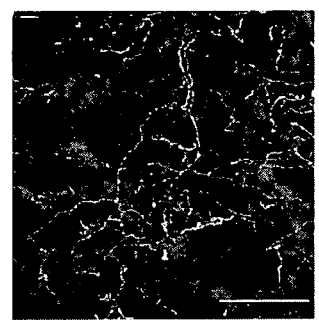
FIGURE 12E
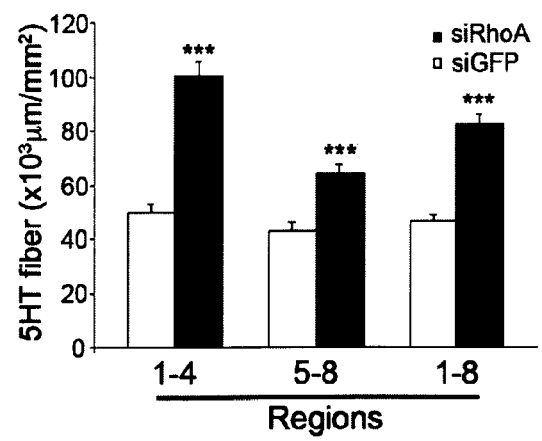

METHODS FOR DELIVERY OF SIRNA TO THE SPINAL CORD AND THERAPIES ARISING THEREFROM

This application is a §371 national stage of PCT International Application No. PCT/US2010/055759, filed Nov. 8, 2010, claiming the benefit of U.S. Provisional Patent Application No. 61/259,173, filed Nov. 8, 2009, the contents of each of which are hereby incorporated by reference in their entirety.

The work disclosed herein was supported in part with grant no. 04-023-SCR2 from the New Jersey Commission on Spinal Cord Research (NJCSCR).

REFERENCE TO SEQUENCE LISTING

This application incorporates-by-reference nucleotide and/or amino acid sequences which are present in the file named "120507_2094_84119_Substitute_Sequence_Listing_GC.txt," which is 26.0 kilobytes in size, and which was created May 2, 2012 in the IBM-PC machine format, having an operating system compatibility with MS-Windows, which is contained in the text file filed May 7, 2012 as part of this application.

FIELD OF THE INVENTION

The present application relates at least in part to methods for the administration of small interfering RNAs (siRNAs) to the spinal cord of a human or animal patient and also to a method for treatment of spinal cord injury and neuopathic pain. In particular, the application discloses methods to prevent and treat neuropathic pain and allodynia and methods to treat an injured spinal cord to promote recovery of CNS function.

BACKGROUND siRNA represents a promising therapeutic technology, however hurdles remain to be overcome in the administration of siRNA to a patient. Various techniques have been employed to introduce siRNA into cells including cationic lipid-mediated transfection, viral delivery and nucleofection. Delivery using cationic lipids appears to be the easiest method for transfection, however its efficiency is often low and limited to specific types of cells. While viral delivery works well for some difficult cells, cell lines, and for in vivo delivery (Garraway et al., 2007, J Pharmacol Exp Ther. 322:982-8) it has raised safety concerns. Unmodified siRNA single strands or duplexes are extremely unstable in serum, with a half-life of less than 1 minute for the single strands and 3.3 to 5 minutes for the duplexes (Sioud, 2005. Curr Drug Targets. 6:647-53; Sioud and Iversen, 2005. Curr Drug Targets. 6:647-53). However, chemical modifications of the siRNAs have demonstrated dramatic improvement in stabilities; modified siRNA were approximately 900-fold more stable than unmodified siRNAs (Morrissey et al., 2005. Nat Biotechnol. 23:1002-7). Certain stable and active siRNA compounds are disclosed in PCT patent publications WO 2008/050329 and WO 2009/044392, assigned to an applicant of the present invention and hereby incorporated by reference in their entirety.

Delivery of siRNAs to the central nervous system (CNS) is problematic because of the blood brain barrier (BBB) and most successful strategies have used an intrathecal route. Intracerebroventricular infusion of naked siRNA at a high concentration via minipumps into the rodent brain have successfully inhibited target gene expression, however, knockdown of target gene expression drops off significantly in regions distant from the infusion site (Thakker et al., 2004. Proc Natl Acad Sci USA. 101:17270-5). Using a lumbar indwelling cannula attached to an osmotic minipump, intrathecal application of high doses (400 μg/day) of siRNAs in the spinal cord silenced the ATP-gated cation-channel P2X3, and relieved chronic neuropathic pain (Dorn et al., 2004. Nucleic Acids Res. 32:e49). Other studies achieved therapeutic effects after intrathecal delivery with substantially lower doses using an implanted Alzet pump in a chronic mouse model for ALS progression (Wang et al., 2008. J Biol Chem. 283:15845-52) and with pretreatment in acute pain models (Christoph et al., 2006. Biochem Biophys Res Commun. 350:238-43; Luo et al., 2005. Mol Pain. 1:29). Rohl and Kerreck review various methods of RNAi in pain models (J. Neurochem. 99:371-380). Inoue has implicated RhoA activation in neuropathic pain (Inoue et al., 2004. Nat Med 10(7):712-8).

Contusive injuries to the spinal cord produce primary damage to the tissue and initiate a cascade of events called secondary injury, which progresses in several phases over days to weeks (Beattie et al., 2000. J Neurotrauma. 17:915-25). Microglia within the spinal cord become activated rapidly after injury. Activated macrophages begin to accumulate by 3 days after spinal cord injury in the rat (Schwab et al., 2004. Glia. 47:377-86). During the first several days after SCI there is extensive cell death in and around the injury site and the axonal processes of neurons die back from the injury site. These processes are accompanied by complex molecular changes including upregulation of RhoA and its activation in both neural (D'Alessandri et al., 1995. Curr. Eye Res. 14:911-926; Dubreuil et al., 2003. J Cell Biol. 162:233-43; Erschbamer et al., 2005. J Comp Neurol. 484:224-33; Yune et al., 2007. J Neurosci. 27:7751-61) and immune cells (Fu et al., 2007. J Neurosci. 27:4154-64; Pixley et al., 2005 J Cell Sci. 118:1873-83; Schwab et al., 2004), which are believed to contribute to secondary damage as well as to limit axonal regeneration and functional recovery. Cell permeable Rho antagonists (e.g. BA-210), which inhibit the activity of phosphorylated Rho family proteins including RhoA, have shown improved recovery after spinal cord injury in rodents (Lord-Fontaine et al., 2008. J Neurotrauma. 25:1309-22) and are being tested in clinical trials to promote axon regeneration and functional recovery (Baptiste et al., 2009. Expert Opin Investig Drugs. 18:663-73). RhoA protein levels are upregulated several fold reaching their highest levels in the rat spinal cord ~7 days following spinal cord contusion, providing a window for therapeutic intervention after SCI (Erschbamer et al., 2005 supra). However, BA-210 inhibition of RhoA was found only up to 4 days after acute treatment but not at one week (Lord-Fontaine et al., 2008) when RhoA expression is robust (Erschbamer et al., 2005). Methods for targeted delivery of siRNA to the CNS and enhanced activity in the target cells would be desirable.

Pain is the most common symptom of disease and the most frequent complaint with which patients present to physicians. Inadequate pain management remains a major public health problem. Currently available treatment options for allodynia/SCI associated pain are limited and since many SCI pain conditions are not amenable to treatment, particularly at-level and below-level neuropathic pain, management becomes largely symptomatic. A solution for the treatment of allodynia/SCI associated pain is therefore required.

SUMMARY OF THE INVENTION

Methods for treatment of diseases, disorders and injury of the central nervous system are provided herein. The application discloses a method to deliver siRNA to an injured or diseased spinal cord in a subject in the absence of transduction vehicles, delivery carriers or delivery systems and provides a method of treating diseases, disorders and injury of the central nervous system including spinal cord injury, neurodegeneration and neuropathic pain.

In one aspect provided is a method of treating a subject suffering from a disease, a disorder or an injury of the CNS associated with expression of a target gene, comprising locally administering to the subject's spinal cord a double stranded RNA compound directed to the target gene in an amount effective to treat the subject. In some embodiments the double stranded RNA compound is administered intraparenchymally and/or by lumbar injection. In some embodiments the double stranded RNA compound is administered intraparenchymally. In preferred embodiments the double stranded RNA compound is administered by lumbar injection. In some embodiments the double stranded RNA is administered to the subject by lumber puncture 0 to 48 hours post injury or onset of the disease. In some embodiments the double stranded RNA is administered to the subject by lumber puncture 0 to 42 hours, 0 to 36 hours, 0 to 30 hours or 0 to 24 hours post injury or onset of disease.

In some embodiments the subject is suffering from pain. In various embodiments the pain is neuropathic pain. In particular embodiments provided is a method of treating or preventing neuropathic pain in a subject, comprising administering to the subject a double stranded RNA compound directed to a target gene selected from RhoA or TLR4, in an amount effective to treat or prevent neuropathic pain in the subject. In prefered embodiments the double stranded RNA compound is administered by lumbar injection.

In some embodiments the neuropathic pain is postherpatic neuralgia, trigeminal neuralgia, and neuropathic pain associated with a condition selected from the group consisting of herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, and cancer chemotherapeutic-induced neuropathic pain.

In some embodiments the double stranded RNA is siRNA. In preferred embodiments the siRNA compound is administered as naked siRNA.

In some embodiments the siRNA is synthetic, chemically modified siRNA. In some embodiments the disease, disorder or injury of the CNS is associated with expression of a gene selected from a nociceptor-specific gene or a gene expressed in a nociceptive neuron.

In some embodiments the disease, disorder or injury of the CNS is associated with expression of a gene selected from APP, MAPT, SOD1, BACE1, CASP3, TGM2, NFE2L3, TARDBP, ADRB1, CAMK2A, CBLN1, CDK5R1, GABRA1, MAPK10, NOS1, NPTX2, NRGN, NTS, PDCD2, PDE4D, PENK, SYT1, TTR, FUS, LRDD, CYBA, ATF3, ATF6, CASP2, CASP1, CASP7, CASP8, CASP9, HRK, C1QBP, BNIP3, MAPK8, MAPK14, Rac1, GSK3B, P2RX7, TRPM2, PARG, CD38, STEAP4, BMP2, GJA1, TYROBP, CTGF, ANXA2, RHOA, DUOX1, RTP801, RTP801L, NOX4, NOX1, NOX2 (gp91pho, CYBB), NOX5, DUOX2, NOXO1, NOXO2 (p47phox, NCF1), NOXA1, NOXA2 (p67phox, NCF2), p53 (TP53), HTRA2, KEAP1, SHC1, ZNHIT1, LGALS3, HI95, SOX9, ASPP1, ASPP2, CTSD, CAPNS1, FAS and FASLG, NOGO and NOGO-R; TLR1, TLR2, TLR3, TLR4, TLR6, TLR7, TLR8, TLR9, IL1bR, MYD88, TICAM, TIRAP, HSP47.

In some embodiments the method disclosed herein results in recovery of certain lost functions including motor functions in a subject having SCI. Motor functions include use of arms and legs, including regaining walking function. In some embodiments the method results in preservation of white matter in a subject suffering from a disease, disorder or injury of the CNS. In some embodiments the method suppresses SCI-induced neuropathic pain or allodynia. In some embodiments the method prevents allodynia in a subject with SCI.

Without wishing to be bound to theory, the siRNA when administered in accordance with the present method, diffuse rapidly in the CNS tissue and are taken up by various cell types including neurons, astrocytes, macrophages and endothelial cells and reduce the SCI-induced increase in target protein (i.e. target genes in Table A) at one week after treatment.

Other objects, features and advantages of the present invention will become clear from the following description and examples.

BRIEF DESCRIPTION OF THE DRAWINGS

FIGS. 1A-1F: Uptake of siRNA in SCI. Micrographs (FIG. 1A) taken 3 days following SCI and intraparenchymal injections at 3 sites (centered at impact site, and 2 mm rostral and caudal) with 1 µl of 1 µg/µl Cy3.5-siRNA each at a depth of 1 mm. Uptake is widespread with labeled cells identified as far as 5 mm rostral and caudal from the injection sites. Micrographs show examples of different types of cells analyzed including motor neurons (FIG. 1B), macrophages (FIG. 1C), axons (FIG. 1D) and endothelial cells (FIG. 1E). Scale bar=20 µm (micrometer). The relative prevalence (rare, + to frequent, ++++) for the each type of labeled cells at different incubation times are summarized in the table in FIG. 1F.

FIGS. 6A-6G. Distribution of Cy3.5-labeled siRNA one day following delivery by lumbar puncture. About 24 h after 12.5 mm MASCIS contusion at T9-10, Cy3.5-labeled siRNA was injected at the L¾level. Dorsal view of a whole spinal cord under fluorescence dissection microscope (FIG. 6A); the arrow shows the location of lumbar puncture. After fixation and cryosectioning cross sections were photographed at the injury center (I) and at locations proximal (P) including the cervical region in FIG. 6B (location is not shown in FIG. 6A), and distal (D-) to the injury site as indicated (FIGS. 6B-6G). Labeled siRNA was observed in gray matter in injury site and very weakly in the proximal region (FIG. 6C), but not in the cervical region (FIG. 6B). In distal regions (FIGS. 6E-6G), Cy3.5-labeled siRNA was localized primarily surrounding the surface of the spinal cord, in the central canal and in the grey matter.

FIG. 7A shows that gene expression level of RhoA (as measured by q-RTPCR) at the injury site (I) at day 4 after moderate contusion injury was significantly decreased by treatment of siRhoA when administered using lumbar puncture (SCI only: n=5; control siRNA: n=8; 30 ug siRhoA: n=5 and 100 ug siRhoA: n=5). FIG. 7B shows that RhoA protein level as measured by ELISA in the injury site (I) at day 4 after moderate contusion injury was also significantly suppressed by 100 ug siRhoA administered using lumbar puncture.

(FIG. 9A) One day after 12.5 mm MASCIS contusion siRNAs were injected in lumbar spinal cords and measurements were made of pressure withdrawal threshold (PWT) with von Frye filaments on the glabrous surface of the hindpaw (siGFP n=7, siRhoA n=7); ANOVA, p=0.0023. (FIG. 9B) The lateral hindpaw test was performed on the same groups of rats included in FIG. 9A; the sensitivity was higher but the pattern of change parallels that observed for the glabrous paw test (siGFP n=7, siRhoA n=7); ANOVA, p=0.0001.

FIGS. 12A-12E. siRhoA promoted higher serotonergic fiber reactivity caudal to the injury site. Transverse sections of the spinal cord at 12 mm distal to lesion showed higher intensities of serotonergic fibers in multiple regions of siRhoA—treated rats (FIG. 12B) than in siGFP treated controls (FIG. 12A). The location of eight areas (each area is 167.41 um×167.41 um) that were measured (FIG. 12C). A representative higher power confocal microscopic image of serotonergic staining shows fiber staining (FIG. 12D). Serotonin fiber lengths in the designated areas (FIG. 12C) were quantified and the averages in area 1-4, 5-8 and 1-8 were all found to be significantly (*** p=0.018) higher in the siRhoA group (n=8) by comparison to the siGFP (n=8) control (FIG. 12E), Scale bar=50 µm.

DETAILED DESCRIPTION OF THE INVENTION

Figure 2A:
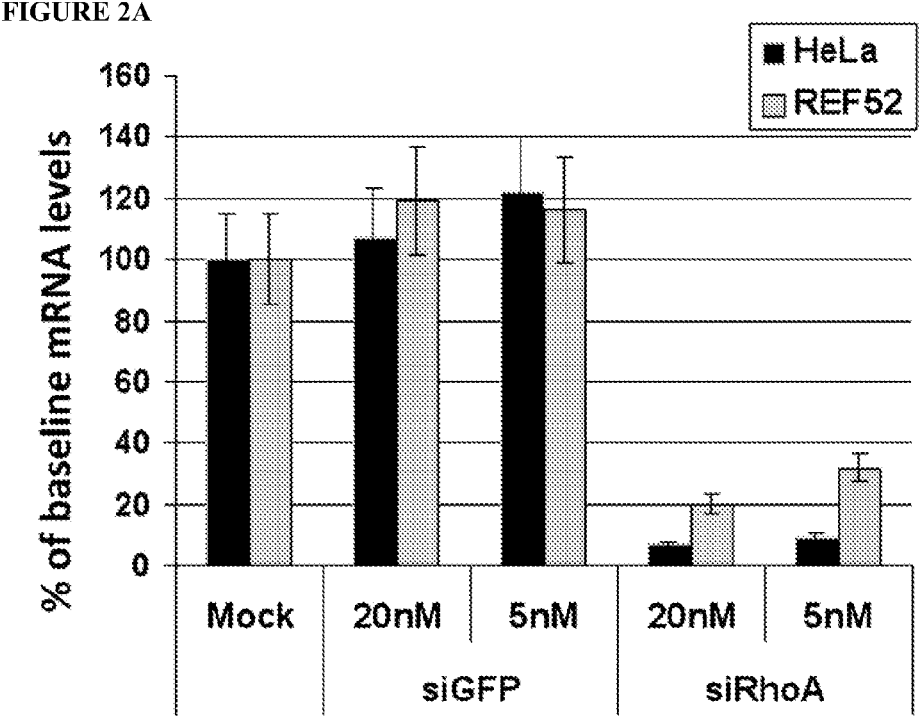
FIGS. 2A-2B. Activity and stability of siRhoA in vitro. Effects of siGFP and siRhoA on RhoA mRNA were quantified using qPCR after transfection into HeLa and REF52 cells using Lipofectamine™2000. Vertical axis shows RhoA mRNA quantities as the percentage of control mock-transfected cells (FIG. 2A). Aliquots of 1 µg of siRhoA were incubated in 20 µL of complete rat CSF at 37° C. for different time intervals and then analyzed on nondenaturing 20% polyacrylamide gel electrophoresis (FIG. 2B). Similar quantities of siRhoA dissolved in PBS were used for size control.

Representative delivery methods of the present invention include 1) intraparenchymal injection at the time of surgery to stabilize damaged vertebrae (Lenehan B et al., 2010) or at the time of any other surgery on the spinal cord, for example for decompression, tumors, etc.; and 2) bolus injection via lumbar puncture delivery.

Definitions

For convenience certain terms employed in the specification, examples and claims are described herein.

It is to be noted that, as used herein, the singular forms "a", "an" and "the" include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

An "inhibitor" is a compound which is capable of reducing the expression of a gene or the activity of the product of such gene to an extent sufficient to achieve a desired biological or physiological effect. The term "inhibitor" as used herein refers to one or more of an oligonucleotide inhibitor, including double stranded RNA and antisense compounds. Double stranded RNA includes siRNA, shRNA and miRNA. The application includes for example, antisense and siRNA oligonucleotides to RhoA, TLR4 and other target genes, such as disclosed in in Table A. Inhibition may also be referred to as down-regulation or, for RNAi, silencing.

The term "inhibit" as used herein refers to reducing the expression of a gene or the activity of the product of such gene to an extent sufficient to achieve a desired biological or physiological effect. Inhibition may be complete or partial.

"Spinal cord injury" or "SCI" or myelopathy, is a disturbance of the spinal cord that results in loss of sensation and/or mobility. The two common types of spinal cord injury are due to trauma and disease. Traumatic injury can result from automobile accidents, falls, gunshot, diving accidents inter alia, and diseases that can affect the spinal cord include polio, spina bifida, tumors, Amyotrophic Lateral Sclerosis (ALS), Multiple Sclerosis (MS) syringomyelia, transverse myelitis and Friedreich's ataxia. SCI refers to damage to the spinal cord resulting from compression, interruption of the to the blood supply to the nerves of the spinal cord, or severing of the spinal cord. SCI includes spinal cord trauma which is damage to the spinal cord resulting from direct injury to the cord per se or indirectly from damage to surrounding bones, tissues, or blood vessels.

A "nociceptor" refers to a sensory receptor that responds to pain or pressure, temperature or chemicals. Nociceptors are typically classified by the environmental stimuli to which they respond. Some nociceptors respond to more than one stimulus and are designated polymodal. The nociceptors of particular relevance to the disclosure, are nociceptors expressed in GABAergic neurons. (For example, see Pharmacological Management Of Neuropathic Pain Following Spinal Cord Injury. Baastrup C, Finnerup N B. CNS Drugs. 2008;22(6):455-75).

Neuropathic pain is characterized by a distinct set of symptoms which can include enhanced sensitivity to innocuous thermal-mechanical stimuli, abnormal sensitivity to noxious stimuli, tenderness, and spontaneous burning pain. Neuropathic pain is also progressive and generally worsens over time. Neuropathic pain is produced by damage to, or pathological changes in, the peripheral nervous system (PNS) or central nervous system (CNS).

Examples of pathological changes include prolonged peripheral or central neuronal sensitization, central sensitization related damage to nervous system inhibitory functions, and abnormal interactions between the somatic and sympathetic nervous systems. Examples of neuropathic pain include monoradiculopathies, trigeminal neuralgia, postherpetic neuralgia, phantom limb pain, complex regional pain syndromes and the various peripheral neuropathies. In some embodiments neuropathic pain is postherpatic neuralgia, or neuropathic pain associated with a condition selected from herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, and cancer chemotherapeutic-induced neuropathic pain. The method of claim 1, wherein the neuropathic pain is associated with a condition selected from the group consisting of traumatic nerve injury, post-ischemia, fibromyalgia, reflex sympathetic dystrophy, complex regional pain syndrome, sciatica, phantom limb pain, diabetic neuropathy, and cancer chemotherapeutic-induced neuropathic pain. In some embodiments neuropathic pain is caused by a malignant tumor, stroke, postherpetic neuralgia, neuropathy with monoclonal protein, vasculitic neuropathy, neuropathy associated with Guillain-Barre syndrome, neuropathy associated with Fabry's disease, an inflammatory condition, an autoimmune disorder including mulitiple sclerosis, a toxin, a drug, a hereditary abnormality, a mastectomy, or an amputation.

The hallmarks of neuropathic pain are chronic allodynia and hyperalgesia.

Allodynia refers to pain resulting from a stimulus that ordinarily does not elicit a painful response, for example light pressure.

Hyperalgesia refers to increased sensitivity to a normally painful stimulus. Primary hyperalgesia, caused by sensitization of C-fibers, occurs immediately within the area of the injury. Secondary hyperalgesia, caused by sensitization of dorsal horn neurons, occurs in the undamaged area surrounding the injury.

Analgesia, or the reduction of pain perception, can be affected by decreasing transmission along the nociceptive pathways. CNS-mediated analgesia leads to an overall inhibition of the pain transmission.

Pain is the most common symptom of disease and the most frequent complaint with which patients present to physicians. The phrase "pain management medication" includes one or more therapeutic agents that are administered to prevent, alleviate or remove pain entirely. According to the present application a pain management medication includes double stranded RNA molecules, including siRNA molecules, that inhibit or down regulate a target gene, selected from Table A.

A "siRNA inhibitor" is a compound which is capable of reducing the expression of a gene or the activity of the product of such gene to an extent sufficient to achieve a desired biological or physiological effect. The term "siRNA inhibitor" as used herein refers to one or more of a siRNA, siNA, shRNA, synthetic shRNA; miRNA Inhibition may also be referred to as down-regulation or, for RNA interference (RNAi), silencing The term "inhibit" as used herein refers to reducing or down regulating the expression of a gene or the activity of the product of such gene to an extent sufficient to achieve a desired biological or physiological effect. Inhibition may be complete or partial.

As used herein, the term "inhibition" of a target gene means inhibition of gene expression (transcription or translation) or polypeptide activity. The polynucleotide sequence of the target mRNA sequence, refers to the mRNA sequences, or any homologous sequences thereof preferably having at least 70% identity, more preferably 80% identity, even more preferably 90% or 95% identity to a target mRNA, in a non-limiting example mRNA sequences of target genes set forth in SEQ ID NO:1 and SEQ ID NO:2. Therefore, polynucleotide sequences, which have undergone mutations, alterations or modifications as described herein are encompassed in the present invention. The terms "mRNA polynucleotide sequence" and "mRNA" are used interchangeably. RhoA is a GTPase that regulates the actin cytoskeleton and it is upregulated following spinal cord injury and has been shown to be expressed in the trabecular meshwork of the eye.

As used herein, the terms "polynucleotide" and "nucleic acid" may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs. Throughout this application, mRNA sequences are set forth as representing the corresponding genes.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds disclosed herein encompass molecules comprising deoxyribonucleotides, ribonucleotides, modified deoxyribonucleotides, modified ribonucleotides and combinations thereof.

"Nucleotide" is meant to encompass deoxyribonucleotides and ribonucleotides, which may be natural or synthetic, and or modified or unmodified. Modifications include changes to the sugar moiety, the base moiety and or the linkages between ribonucleotides in the oligoribonucleotide. As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide.

RNA Interference and siNA Nucleic Acid Molecules

RNA interference (RNAi) refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13:139-141; and Strauss, 1999, Science, 286, 886). The corresponding process in plants (Heifetz et al., International PCT Publication No. WO 99/61631) is often referred to as post-transcriptional gene silencing (PTGS) or RNA silencing.

The presence of long dsRNAs in cells stimulates the activity of a ribonuclease III enzyme referred to as Dicer (Bass, 2000, Cell, 101, 235; Zamore et al., 2000, Cell, 101, 25-33; Hammond et al., 2000, Nature, 404, 293). Dicer is involved in the processing of the dsRNA into short dsRNA segments known as short interfering RNAs (siRNAs) (Zamore et al., 2000, Cell, 101, 25-33; Bass, 2000, Cell, 101, 235; Berstein et al., 2001, Nature, 409, 363). Short interfering RNAs derived from Dicer activity are typically about 21 to about 23 nucleotides in length and include about 19 base pair duplexes (Zamore et al., 2000, Cell, 101, 25-33; Elbashir et al., 2001, Genes Dev., 15, 188). The cytoplasmic RNAi response features an endonuclease complex, commonly referred to as RISC, RNA-induced silencing complex, which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

The inhibitors or therapeutic agents disclosed herein comprise nucleic acid molecules. As used herein, the term "nucleic acid molecule" or "nucleic acid" are used interchangeably and refer to an oligonucleotide, nucleotide or polynucleotide. Variations of "nucleic acid molecule" are described in more detail herein. A nucleic acid molecule encompasses both modified nucleic acid molecules and unmodified nucleic acid molecules as described herein. A nucleic acid molecule may include deoxyribonucleotides, ribonucleotides, modified nucleotides or nucleotide analogs in any combination.

In some embodiments provided re the double stranded nucleic acid molecules having the structure (A)

(A)   '5 (N)x-Z 3'          (antisense strand)

3' Z'-(N')y-z" 5'      (sense strand)

wherein each of N and N' is a nucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present independently includes 1-5 consecutive nucleotides or non-nucleotide moieties or a combination thereof covalently attached at the 3' terminus of the strand in which it is present;

wherein z" may be present or absent, but if present is a capping moiety covalently attached at the 5' terminus of (N')y;

each of x and y is independently an integer from 18 to 40;

wherein the sequence of (N')y has complementary to the sequence of (N)x; and wherein (N)x includes an antisense sequence to mRNA of a gene upregulated in spinal cord injury, disease or disorder.

In some embodiments the covalent bond joining each consecutive N or N' is a phosphodiester bond.

In some embodiments x=y and each of x and y is 19, 20, 21, 22 or 23. In various embodiments x=y=19. In some embodiments the antisense and sense strands form a duplex by base pairing In some embodiments the 5' terminal nucleotide of the antisense strand (position 1 of the antisense strand) is mismatched to the target mRNA. In some embodiments the 5' terminal nucleotide of the antisense strand is a modified riboadenosine or a modified ribouridine.

In some embodiments Z and Z' are absent. In other embodiments one of Z or Z' is present.

As used herein, the term "nucleotide" refers to a chemical moiety having a sugar (or an analog thereof, or a modified sugar), a nucleotide base (or an analog thereof, or a modified base), and a phosphate group (or analog thereof, or a modified phosphate group). A nucleotide encompasses both modified nucleotides or unmodified nucleotides as described herein. As used herein, nucleotides may include deoxyribonucleotides (e.g., unmodified deoxyribonucleotides), ribonucleotides (e g , unmodified ribonucleotides), and modified nucleotide analogs including, inter alia, locked nucleic acids and unlocked nucleic acids, peptide nucleic acids, L-nucleotides (also referred to as mirror nucleotides), ethylene-bridged nucleic acid (ENA), arabinoside, PACE, nucleotides with a 6 carbon sugar, as well as nucleotide analogs (including abasic nucleotides) often considered to be non-nucleotides.

In some embodiments, nucleotides may be modified in the sugar, nucleotide base and/or in the phosphate group with any modification known in the art, such as modifications described herein. A "polynucleotide" or "oligonucleotide" as used herein refer to a chain of linked nucleotides; polynucleotides and oligonucleotides may likewise have modifications in the nucleotide sugar, nucleotide bases and phosphate backbones as are well known in the art and/or are disclosed herein.

As used herein, the term "short interfering nucleic acid", "siNA", or "short interfering nucleic acid molecule" refers to any nucleic acid molecule capable of modulating gene expression or viral replication. Preferably siNA inhibits or down regulates gene expression or viral replication. siNA includes without limitation nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. As used herein, "short interfering nucleic acid", "siNA", or "short interfering nucleic acid molecule" has the meaning described in more detail elsewhere herein.

As used herein, the term "complementary" means that a nucleic acid can form hydrogen bond(s) with another nucleic acid sequence by either traditional Watson-Crick or other non-traditional types. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Fully complementary" means that all the contiguous residues of a nucleic acid sequence will hydrogen bond with the same number of contiguous residues in a second nucleic acid sequence. In one embodiment, a nucleic acid molecule disclosed herein includes about 15 to about 35 or more (e.g., about 15, 16, 17, 18, 19, 20, 21, 22, 23, 24, 25, 26, 27, 28, 29, 30, 31, 32, 33, 34 or 35 or more) nucleotides that are complementary to one or more target nucleic acid molecules or a portion thereof.

As used herein, the term "sense region" refers to a nucleotide sequence of a siNA molecule complementary (partially or fully) to an antisense region of the siNA molecule. The sense strand of a siNA molecule can include a nucleic acid sequence having homology with a target nucleic acid sequence. As used herein, "sense strand" refers to nucleic acid molecule that includes a sense region and may also include additional nucleotides. The sense strand is also referred to as the passenger strand.

As used herein, the term "antisense region" refers to a nucleotide sequence of a siNA molecule complementary (partially or fully) to a target nucleic acid sequence. The antisense strand of a siNA molecule can optionally include a nucleic acid sequence complementary to a sense region of the siNA molecule. As used herein, "antisense strand" refers to nucleic acid molecule that includes an antisense region and may also include additional nucleotides. The antisense strand is also referred to as the guide strand.

As used herein, the term "RNA" refers to a molecule that includes at least one ribonucleotide residue.

As used herein, the term "duplex region" refers to the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well know in the art. Alternatively, two strands can be synthesized and added together under biological conditions to determine if they anneal to one another.

As used herein, the terms "non-pairing nucleotide analog" means a nucleotide analog which includes a non-base pairing moiety including but not limited to: 6des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide.

As used herein, the term, "terminal functional group" includes without limitation a halogen, alcohol, amine, carboxylic, ester, amide, aldehyde, ketone, ether groups.

An "abasic moiety" or "abasic nucleotide analog" is as used herein may also be referred to herein and in the art as a pseudo-nucleotide or an unconventional moiety. While a nucleotide is a monomeric unit of nucleic acid, generally consisting of a ribose or deoxyribose sugar, a phosphate, and a base (adenine, guanine, thymine, or cytosine in DNA; adenine, guanine, uracil, or cytosine in RNA). an abasic or pseudo-nucleotide lacks a base, and thus is not strictly a nucleotide as the term is generally used in the art. Abasic deoxyribose moieties include for example, abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moieties include inverted deoxyriboabasic; 3',5' inverted deoxyabasic 5'-phosphate.

The term "capping moiety" (or " z" in structure (A)) as used herein includes a moiety which can be covalently linked to the 5' terminus of (N')y and includes abasic ribose moiety, abasic deoxyribose moiety, modifications abasic ribose and abasic deoxyribose moieties including 2'O alkyl modifications; inverted abasic ribose and abasic deoxyribose moieties and modifications thereof; C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain capping moieties may be abasic ribose or abasic deoxyribose moieties; inverted abasic ribose or abasic deoxyribose moieties; C6-amino-Pi; a mirror nucleotide including L-DNA and L-RNA. The nucleic acid molecules as disclosed herein may be synthesized using one or more inverted nucleotides, for example inverted thymidine or inverted adenine (for example see Takei, et al., 2002. JBC 277(26):23800-06).

The term "unconventional moiety" as used herein refers to non-nucleotide moieties including an abasic moiety, an inverted abasic moiety, a hydrocarbon (alkyl) moiety and derivatives thereof, and further includes a deoxyribonucleotide, a modified deoxyribonucleotide, a mirror nucleotide (L-DNA or L-RNA), a non-base pairing nucleotide analog and a nucleotide joined to an adjacent nucleotide by a 2'-5' internucleotide phosphate bond; bridged nucleic acids including LNA and ethylene bridged nucleic acids, linkage modified (e.g. PACE) and base modified nucleotides as well as additional moieties explicitly disclosed herein as unconventional moieties.

As used herein, the term "inhibit", "down-regulate", or "reduce" with respect to gene expression means the expression of the gene, or level of RNA molecules or equivalent RNA molecules encoding one or more proteins or protein subunits (e.g., mRNA), or activity of one or more proteins or protein subunits, is reduced below that observed in the absence of an inhibitory factor (such as a nucleic acid molecule, e.g., an siNA, for example having structural features as described herein); for example the expression may be reduced to 90%, 80%, 70%, 60%, 50%, 40%, 30%, 20%, 10%, 5% or less than that observed in the absence of an inhibitor.

An siNA nucleic acid molecule can be assembled from two separate polynucleotide strands, where one strand is the sense strand and the other is the antisense strand in which the antisense and sense strands are self-complementary (i.e. each strand includes nucleotide sequence that is complementary to nucleotide sequence in the other strand); such as where the antisense strand and sense strand form a duplex or double stranded structure having any length and structure as described herein for nucleic acid molecules as provided, for example wherein the double stranded region (duplex region) is about 17 to about 40 (e.g., about 17, 18, 19, 20, 21, 22, 23, 24, 25, 26, 27, 28, 29, 30, 31, 32, 33, 34, 35, 36, 37, 38, 39 or 40 base pairs); the antisense strand includes nucleotide sequence that is complementary to nucleotide sequence in a target nucleic acid molecule (i.e., RhoA or TLR4 mRNA) or a portion thereof and the sense strand includes nucleotide sequence corresponding to the target nucleic acid sequence or a portion thereof (e.g., about 17 to about 49 or more nucleotides of the nucleic acid molecules herein are complementary to the target nucleic acid or a portion thereof).

In certain aspects and embodiments a nucleic acid molecule (e.g., a siNA molecule) provided herein may be a "RISC length" molecule or may be a Dicer substrate as described in more detail below.

An siNA nucleic acid molecule may include separate sense and antisense sequences or regions, where the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. Nucleic acid molecules may include a nucleotide sequence that is complementary to nucleotide sequence of a target gene. Nucleic acid molecules may interact with nucleotide sequence of a target gene in a manner that causes inhibition of expression of the target gene.

Alternatively, an siNA nucleic acid molecule is assembled from a single polynucleotide, where the self-complementary sense and antisense regions of the nucleic acid molecules are linked by means of a nucleic acid based or non-nucleic acid-based linker(s) for example to form a "hairpin" structure as is well known in the art). Such siNA nucleic acid molecules can be a polynucleotide with a duplex, asymmetric duplex, hairpin or asymmetric hairpin secondary structure, having self-complementary sense and antisense regions, wherein the antisense region includes nucleotide sequence that is complementary to nucleotide sequence in a separate target nucleic acid molecule or a portion thereof and the sense region having nucleotide sequence corresponding to the target nucleic acid sequence (e.g., a sequence of RhoA and TLR4 mRNA). Such siNA nucleic acid molecules can be a circular single-stranded polynucleotide having two or more loop structures and a stem comprising self-complementary sense and antisense regions, wherein the antisense region includes nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active nucleic acid molecule capable of mediating RNAi.

The following nomenclature is often used in the art to describe lengths and overhangs of siNA molecules and may be used throughout the specification and Examples. Names given to duplexes indicate the length of the oligomers and the presence or absence of overhangs.

Chemical Modifications of Nucleic Acid Molecules

In certain aspects and embodiments, nucleic acid molecules (e.g., siNA molecules) as provided herein include one or more modifications (or chemical modifications). In certain embodiments, such modifications include any changes to a nucleic acid molecule or polynucleotide that would make the molecule different than a standard ribonucleotide or RNA molecule (i.e., that includes standard adenine, cytosine, uracil, or guanine moieties); which may be referred to as an "unmodified" ribonucleotide or unmodified ribonucleic acid. Traditional DNA bases and polynucleotides having a 2'-deoxy sugar represented by adenine, cytosine, thymine, or guanine moieties may be referred to as an "unmodified deoxyribonucleotide" or "unmodified deoxyribonucleic acid"; accordingly, the term "unmodified nucleotide" or "unmodified nucleic acid" as used herein refers to an "unmodified ribonucleotide" or "unmodified ribonucleic acid" unless there is a clear indication to the contrary. Such modifications can be in the nucleotide sugar, nucleotide base, nucleotide phosphate group and/or the phosphate backbone of a polynucleotide.

In certain embodiments modifications as disclosed herein may be used to increase RNAi activity of a molecule and/or to increase the in vivo exonuclease and or endonuclease stability of the molecules, particularly the stability in serum, and/or to increase bioavailability of the molecules. Non-limiting examples of modifications include without limitation internucleotide or internucleoside linkages; nucleobase modifications and sugar modifications.

Modified nucleotides include those having a Northern conformation including locked nucleic acid (LNA) nucleotides (e.g., 2'-O, 4'-C-methylene-(D-ribofuranosyl) nucleotides); 2'-methoxyethoxy (MOE) nucleotides; 2'-methyl-thio-ethyl, 2'-deoxy-2'-fluoro nucleotides, 2'-deoxy-2'-chloro nucleotides, 2'-azido nucleotides, and 2'-O-methyl nucleotides. Locked nucleic acids, or LNA's are described, for example, in Elman et al., 2005; Kurreck et al., 2002; Crinelli et al., 2002; Braasch and Corey, 2001; Bondensgaard et al., 2000; Wahlestedt et al., 2000; and International Patent Publication Nos. WO 00/47599, WO 99/14226, and WO 98/39352 and WO 2004/083430. In one embodiment, an LNA is incorporated at the 5' terminus of the sense strand.

Chemical modifications also include unlocked nucleic acids, or UNAs, which are non-nucleotide, acyclic analogues, in which the C2'-C3' bond of the sugar is not present (although UNAs are not truly nucleotides, they are expressly included in the scope of "modified" nucleotides or nucleic acids or unconventional moieties as contemplated herein). In particular embodiments, nucleic acid molecules with an overhang may be modified to have UNAs at the overhang positions (i.e., 2 nucleotide overhand). In other embodiments, UNAs are included at the 3'- or 5'-ends. A UNA may be located anywhere along a nucleic acid strand, i.e. at position 7. Nucleic acid molecules may contain one or more than UNA. Exemplary UNAs are disclosed in Nucleic Acids Symposium Series No. 52 p. 133-134 (2008). In some embodiments, a nucleic acid molecule as described herein that has a 3'-overhang include one or two UNAs in the 3' overhang. In some embodiments a nucleic acid molecule (e.g., a siNA molecule) as described herein includes a UNA (for example one UNA) in the antisense strand; for example in position 6 or position 7 of the antisense strand. Chemical modifications also include non-pairing nucleotide analogs, for example as disclosed herein. Chemical modifications further include unconventional moieties as disclosed herein.

Chemical modifications to the sugar include six membered "six membered ring nucleotide analogs." Examples of six-membered ring nucleotide analogs are disclosed in Allart, et al (Nucleosides & Nucleotides, 1998, 17:1523-1526,; and Perez-Perez, et al., 1996, Bioorg. and Medicinal Chem Letters 6:1457-1460) Oligonucleotides including 6-membered ring nucleotide analogs including hexitol and altritol nucleotide monomers are disclosed in International patent application publication No. WO 2006/047842.

Chemical modifications also include "mirror" nucleotides which have a reversed chirality as compared to normal naturally occurring nucleotide; that is a mirror nucleotide may be an "L-nucleotide" analogue of naturally occurring D-nucleotide (see U.S. Pat. No. 6,602,858). Mirror nucleotides may further include at least one sugar or base modification and/or a backbone modification, for example, as described heron, such as a phosphorothioate or phosphonate moiety. U.S. Pat. No. 6,602,858 discloses nucleic acid catalysts including at least one L-nucleotide substitution. Mirror nucleotides include for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

In some embodiments, modified ribonucleotides include modified deoxyribonucleotides, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate.

Modifications may be present in one or more strands of a nucleic acid molecule disclosed herein, e.g., in the sense strand, the antisense strand, or both strands. In certain embodiments, the antisense strand may include modifications and the sense strand my only include unmodified RNA.

Nucleobases

Nucleobases of the nucleic acid disclosed herein may include unmodified ribonucleotides (purines and pyrimidines) such as adenine, guanine, cytosine, uridine. The nucleobases in one or both strands can be modified with natural and synthetic nucleobases such as, thymine, xanthine, hypoxanthine, inosine, 2-aminoadenine, 6-methyl and other alkyl derivatives of adenine and guanine, any "universal base" nucleotides; 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine, deazapurines, heterocyclic substituted analogs of purines and pyrimidines, e.g., aminoethoxy phenoxazine, derivatives of purines and pyrimidines (e.g., 1-alkyl-, 1-alkenyl-, heteroaromatic- and 1-alkynyl derivatives) and tautomers thereof, 8-oxo-$N^6$-methyladenine, 7-diazaxanthine, 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

Sugar Moieties

Sugar moieties in nucleic acid disclosed herein may include 2'-hydroxyl-pentofuranosyl sugar moiety without any modification. Alternatively, sugar moieties can be modified such as, 2'-deoxy-pentofuranosyl sugar moiety, D-ribose, hexose, modification at the 2' position of the pentofuranosyl sugar moiety such as 2'-O-alkyl (including 2'-O-methyl and 2'-O-ethyl), i.e., 2'-alkoxy, 2'-amino, 2'-O-allyl, 2'-S-alkyl, 2'-halogen (including 2'-fluoro, chloro, and bromo), 2'-methoxyethoxy, 2'-O-methoxyethyl, 2'-O-2-methoxyethyl, 2'-allyloxy (—OCH$_2$CH═CH$_2$), 2'-propargyl, 2'-propyl, ethynyl, ethenyl, propenyl, CF, cyano, imidazole, carboxylate, thioate, $C_1$ to $C_{10}$ lower alkyl, substituted lower alkyl, alkaryl or aralkyl, OCF$_3$, OCN, O—, S—, or N-alkyl; O—, S, or N-alkenyl; SOCH$_3$; SO$_2$CH$_3$; ONO$_2$; NO$_2$, N$_3$; heterozycloalkyl; heterozycloalkaryl; aminoalkylamino; polyalkylamino or substituted silyl.

Alkyl group includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls may have from 3-8 carbon atoms in their ring structure, and more preferably have 5 or 6 carbons in the ring structure. The term $C_1$-$C_6$ includes alkyl groups containing 1 to 6 carbon atoms. The alkyl group can be substituted alkyl group such as alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Alkoxy group includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

In some embodiments, the pentafuronosyl ring may be replaced with acyclic derivatives lacking the C2'-C3'-bond of the pentafuronosyl ring. For example, acyclonucleotides may substitute a 2-hydroxyethoxymethyl group for-the 2'-deoxyribofuranosyl sugar normally present in dNMPs.

Halogens include fluorine, bromine, chlorine, iodine.

Backbone

The nucleoside subunits of the nucleic acid disclosed herein may be covalently linked to each other by phosphodiester bonds. The phosphodiester bond may be optionally substituted with other linkages. For example, phosphorothioate, thiophosphate-D-ribose entities, triester, thioate, 2'-5' bridged backbone (may also be referred to as 5'-2'), PACE, 3'-(or -5')deoxy-3'-(or -5')thio-phosphorothioate, phosphorodithioate, phosphoroselenates, 3'-(or -5')deoxy phosphinates, borano phosphates, 3'-(or -5')deoxy-3'-(or 5'-)amino phosphoramidates, hydrogen phosphonates, phosphonates, borano phosphate esters, phosphoramidates, alkyl or aryl phosphonates and phosphotriester modifications, and non-phosphorus containing linkages for example, carbonate, carbamate, silyl, sulfur, sulfonate, sulfonamide, formacetal, thioformacetal, oxime, methyleneimino, methylenemethylimino, methylenehydrazo, methylenedimethylhydrazo and methyleneoxymethylimino linkages.

Nucleic acid molecules disclosed herein may include a peptide nucleic acid (PNA) backbone. The PNA backbone is includes repeating N-(2-aminoethyl)-glycine units linked by peptide bonds. The various bases such as purine, pyrimidine, natural and synthetic bases are linked to the backbone by methylene carbonyl bonds.

Terminal Phosphates

Modifications can be made at terminal phosphate groups. Non-limiting examples of different stabilization chemistries can be used, e.g., to stabilize the 3'-end of nucleic acid sequences, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide.

Nucleic acid molecules disclosed herein (e.g., siNA, siRNA molecules) may be blunt-ended on both sides, have overhangs on both sides or a combination of blunt and overhang ends. Overhangs may occur on either the 5'- or 3'-end of the sense or antisense strand.

5'- and/or 3'-ends of double stranded nucleic acid molecules (e.g., siNA) may be blunt ended or have an overhang. The 5'-end may be blunt ended and the 3'-end has an overhang in either the sense strand or the antisense strand. In other embodiments, the 3'-end may be blunt ended and the 5'-end has an overhang in either the sense strand or the antisense strand. In yet other embodiments, both the 5'- and 3'-end are blunt ended or both the 5'- and 3'-ends have overhangs.

The 5'- and/or 3'-end of one or both strands of the nucleic acid may include a free hydroxyl group and/or a phosphate group. The 5'- and/or 3'-end of any nucleic acid molecule strand may be modified to include a chemical modification. Such modification may stabilize nucleic acid molecules, e.g., the 3'-end may have increased stability due to the presence of the nucleic acid molecule modification.

Nucleic acid molecules (e.g., siNA, siRNA molecules) disclosed herein may include modified nucleotides as a percentage of the total number of nucleotides present in the nucleic acid molecule. As such, a nucleic acid molecule may include about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given nucleic acid molecule will depend on the total number of nucleotides present in the nucleic acid. If the nucleic acid molecule is single stranded, the percent modification can be based upon the total number of nucleotides present in the single stranded nucleic acid molecule. Likewise, if the nucleic acid molecule is double stranded, the percent modification can be based upon the total number of nucleotides present in the sense strand, antisense strand, or both the sense and antisense strands.

A chemically-modified short interfering nucleic acid (siNA) molecule may include an antisense region, wherein any (e.g., one or more or all) pyrimidine nucleotides present in the antisense region are 2'-O-Methoxy or 2'-deoxy-2'-fluoro pyrimidine nucleotides.

Modification Patterns and Alternating Modifications of Nucleic acid Compounds

Nucleic acid molecules (e.g., siNA molecules) provided herein may have patterns of modified and unmodified nucleic acids. A pattern of modification of the nucleotides in a contiguous stretch of nucleotides may be a modification contained within a single nucleotide or group of nucleotides that are covalently linked to each other via standard phosphodiester bonds or, at least partially, through phosphorothioate bonds. Accordingly, a "pattern" as contemplated herein, does not necessarily need to involve repeating units, although it may. Examples of modification patterns that may be used in conjunction with the nucleic acid molecules (e.g., siNA molecules) provided herein include those disclosed in Giese, U.S. Pat. No. 7,452,987. For example, nucleic acid molecules (e.g., siNA molecules) provided herein include those having modification patterns such as, similar to, or the same as, the patterns shown diagrammatically in U.S. Pat. No. 7,452,987.

In some double stranded nucleic acid molecules include a 2'-O-methyl (2'-OMethoxy; 2'-OCH3) modified nucleotide and a non-modified nucleotide, preferably a nucleotide which is not 2'-O-methyl modified, are incorporated on both strands in an alternating fashion, resulting in a pattern of alternating 2'-O-methyl modified nucleotides and ribonucleotides that are either unmodified or at least do not include a 2'-O-methyl modification. In certain embodiments, the same sequence of 2'-O-methyl modification and non-modification exists on the second strand; in other embodiments the alternating 2'-O-methyl modified nucleotides are only present in the sense strand and are not present in the antisense strand; and in yet other embodiments the alternating 2'-O-methyl modified nucleotides are only present in the sense strand and are not present in the antisense strand. In certain embodiments, there is a phase shift between the two strands such that the 2'-O-methyl modified nucleotide on the first strand base pairs with a non-modified nucleotide(s) on the second strand and vice versa.

Exemplary Modification Locations and Patterns of Nucleic Acid Compounds

While exemplary patterns are provided in more detail below, all permutations of patterns with of all possible characteristics of the nucleic acid molecules disclosed herein and those known in the art are contemplated (e.g., characteristics include, but are not limited to, length of sense strand, length of antisense strand, length of duplex region, length of hangover, whether one or both ends of a double stranded nucleic acid molecule is blunt or has an overhang, location of modified nucleic acid, number of modified nucleic acids, types of modifications, whether a double overhang nucleic acid molecule has the same or different number of nucleotides on the overhang of each side, whether a one or more than one type of modification is used in a nucleic acid molecule, and number of contiguous modified/unmodified nucleotides). With respect to all detailed examples provided below, while the duplex region is shown to be 19 nucleotides, the nucleic acid molecules provided herein can have a duplex region ranging from 1 to 49 nucleotides in length as each strand of a duplex region can independently be 17-49 nucleotides in length Exemplary patterns are provided herein.

The siRNA molecules of the present invention may be delivered to the target tissue by direct application of the naked molecules prepared with a carrier or a diluent.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

However, in some embodiments the siRNA molecules of the invention are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Particular siRNA molecules used herein include:
RHOA_4:
The unmodified sequence of the molecule is: Sense 5'>3': GCCACTTAATGTATGTTAC and Antisense 5'>3': GTAACATACATTAAGTGGC. The chemically modified compound is as follows:

```
Sense:
5' rG; mC; rC; mA; rC; mU; rU; mA; rA; mU; rG; mU;

rA; mU; rG; mU; rU; mA; rC

AntiSense:
5' mG; rU; mA; rA; mC; rA; mU; rA; mC; rA; mU; rU;

mA; rA; mG; rU; mG; rG; mC
```

TLR4_4:
The unmodified sequence of the molecule is: Sense 5'>3': GAGTTCAGGTTAACATATA Antisense 5'>3': TATATGTTAACCTGAACTC. The chemically modified compound is as follows:

```
Sense:
5' rG; mA; rG; mU; rU; mC; rA; mG; rG; mU; rU; mA;

rA; mC; rA; mU; rA; mU; rA

AntiSense:
5' mU; rA; mU; rA; mU; rG; mU; rU; mA; rA; mC;

rC; mU; rG; mA; rA; mC; rU; mC
``` wherein "r" preceding a ribonucleotide A, C, G or U denotes an unmodified ribonucleotide and "m" denotes a 2'-OCH3 modified ribonucleotide.

Additional siRNAs directed towards relevant target genes are disclosed in PCT patent application publication No. WO2008/050329 and WO2009/044392, assigned to an assignee of the present invention, which are hereby incorporated by reference in their entirety.

Indications
Spinal Cord Injury (SCI)

In one embodiment the injury to the CNS is Spinal Cord Injury (SCI) or myelopathy. SCI or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases that can affect the spinal cord include polio, spina bifida, tumors, Amyotrophic Lateral Sclerosis (ALS), Multiple Sclerosis (MS) syringomyelia, transverse myelitis and Friedreich's ataxia.

In various embodiments, the compounds and methods disclosed herein are used for treating or preventing the damage caused by spinal-cord injury especially spinal cord trauma caused by motor vehicle accidents, falls, sports injuries, industrial accidents, gunshot wounds, spinal cord trauma caused by spine weakening (such as from rheumatoid arthritis or osteoporosis) or if the spinal canal protecting the spinal cord has become too narrow (spinal stenosis) due to the normal aging process, direct damage that occur when the spinal cord is pulled, pressed sideways, or compressed, damage to the spinal-cord following bleeding, fluid accumulation, and swelling inside the spinal cord or outside the spinal cord (but within the spinal canal). The otic pharmaceutical compositions of the invention are also used for treating or preventing the damage caused by spinal-cord injury due to disease such as polio or spina bifida. Other indications include hyperalgesia and allodynia.

Allodynia

Allodynia is "other pain", defined as pain from stimuli that are not normally painful. The pain may occur other than in the area stimulated.

Allodynia and Spinal Cord Injury (SCI)

Chronic pain is one of the more frequent and troublesome sequelae of SCI, often interfering with the effective rehabilitation of the patient. In addition to the chronic pain syndromes seen in the non-SCI population, e.g., migraine and postherpetic neuralgia, patients with SCI may also suffer from pain syndromes unique to SCI. The reported prevalence of chronic SCI pain varies between 25% and 94%, with almost one-third of these patients experiencing severe pain (Bonica J J. Introduction: semantic, epidemiologic, and educational issues. In: Casey K L, ed. Pain and central nervous system disease: the central pain syndromes. New York: Raven Press, 1991:13-29; Siddall P J, Taylor D A, McClelland J M, Rutkowski S B, Cousins M J. Pain report and the relationship of pain to physical factors in the first six months following spinal cord injury. Pain 1999;81:187-97; Gerhart K A, Johnson R L, Whiteneck G G. Health and psychosocial issues of individuals with incomplete and resolving spinal cord injuries. Paraplegia 1992;30:282-7). Several studies have reported the prevalence of the various types of SCI pain. Musculoskeletal pain was the most common type experienced at 6 mo after injury (40%) (Siddall P J, Taylor D A, McClelland J M, Rutkowski S B, Cousins M J. Pain report and the relationship of pain to physical factors in the first six months following spinal cord injury. Pain 1999;81:187-97) and at 5 yr after SCI (59%) (Siddall P J, McClelland J M, Rutkowski S B, Cousins M J. A longitudinal study of the prevalence and characteristics of pain in the first 5 years following spinal cord injury. Pain 2003;103:249-57). An increase in the prevalence of at-level and below-level neuropathic pain has likewise been observed more than 5 yr after SCI. Variables that influence the development of SCI pain remain unclear. Factors such as the level of the injury, completeness of the injury, cause of injury, and psychosocial factors have been considered (Siddall P J, Yezierski R P, Loeser J D Taxonomy and epidemiology of spinal cord injury pain. In: Yezierski R P, Burchiel K J, eds. Spinal cord injury pain: assessment, mechanisms, management. Progress in Pain Research and Management. Vol. 23 Seattle: IASP Press, 2002:9-24). Musculoskeletal pain was more common in patients with thoracic level injuries and was reported to be more prevalent in those who had surgical intervention 2 wk after SCI (Sved P, Siddall P J, McClelland J M, Cousins M J. Relationship between surgery and pain following spinal cord injury. Spinal Cord 1997;35:526-30). Neuropathic pain that was associated with allodynia was observed to be more common in patients with incomplete spinal cord lesions, in cervical than thoracic cord injuries, and in central cord syndrome (Siddall P J, Taylor D A, McClelland J M, Rutkowski S B, Cousins M J. Pain report and the relationship of pain to physical factors in the first six months following spinal cord injury. Pain 1999;81:187-97).

Post-SCI Pain Types

In addition to the four major types of SCI pain under Tier 2, there are other recognized pain conditions, most of which are under Tier 3 in the International Association for the Study of Pain Taxonomy (Siddall P J, Yezierski R P, Loeser J D. Pain following spinal cord injury: clinical features, prevalence, and taxonomy. International Association for the Study of Pain Newsletter 2000;3:3-7). These need to be clinically identified so that appropriate treatment may be instituted.

Musculoskeletal Pain

Mechanical instability of the spine: This type of pain is brought about by disruption of ligaments/joints or fractures of bone, resulting in instability of the spine. It occurs early after injury and is located in the region of the spine close to the site of SCI. It is related to position, worsened by activity and decreased by rest. Diagnosis is aided by radiographs, computerized tomography or MRI to identify the nature and site of pathology.

Muscle spasm pain: Spasticity is defined as a motor disorder characterized by a velocity-dependent increase in the tonic stretch reflexes (muscle tone) with exaggerated tendon reflexes, resulting from hyperexcitability of the stretch reflex. An imbalance in any of the numerous excitatory and inhibitory modulatory synaptic influences on the α motor neuron and muscle results in hyperactivity of the stretch reflex arc. This pain type usually occurs late after SCI, and is often seen in people with incomplete SCI.

At-Level Neuropathic Pain

Segmental deafferentation/Girdle or Border or transitional zone pain: This is a variation of at-level neuropathic pain that occurs within a band of two to four segments above or below the level of SCI. It often occurs on the border of normal sensation and anesthetic skin.

Syringomyelia: Pain due to a syrinx (i.e., an abnormal cyst in the spinal cord) often occurs with a delayed onset, a mean of 6 yr. The damage to the central part of the spinal cord with cervical injuries results in the central cord syndrome characterized by pain and weakness of the arms and relatively strong but spastic leg function. The pain of syringomyelia is sometimes described as a constant burning pain with allodynia.

Below-Level Neuropathic Pain

Central dysaesthesia syndrome/central pain/deafferentation pain: pain diffusely located caudal to the level of SCI, i.e., over the entire body from the shoulders to the feet, typical of below-level neuropathic pain. The pain may be associated with hyperalgesia and may gradually worsen over time. It occurs with spontaneous and/or evoked episodes, and is often worsened by infections, sudden noise, and jarring movements.

Pathophysiology and Mechanisms of SCI Pain

Pain associated with SCI is a consequence of both injury characterized by pathological changes from mechanical trauma and vascular compromise of the cord parenchyma. It is influenced by the nature of the lesion, the neurological structures damaged, and the secondary pathophysiological changes of the surviving tissue. There are at least three proposed basic mechanisms underlying SCI pain: increased neuronal hyperexcitability, reduced inhibition, and neuronal reorganization or plasticity.

Increased Neuronal Hyperexcitability

An initial consequence of SCI after traumatic or ischemic SCI is the brief but dramatic increase of excitatory amino acids, which triggers an injury cascade of secondary pathological changes. The major components of this spinal "central injury cascade" include anatomical, neurochemical, excitotoxic, and inflammatory events that collectively interact to increase the responsiveness of the neurons at the level of injury, resulting in the generation of the clinical symptoms of allodynia and hyperalgesia (Yezierski R P. Pathophysiology and animal models of spinal cord injury pain. In: Yezierski R P, Burchiel K J, eds. Spinal cord injury pain: assessment, mechanisms, management. Progress in pain research and management. Vol. 23. Seattle: IASP Press, 2002:117-36).

Existing Treatment Options

Pharmacological Treatment

The first-line medications include systemic lidocaine, gabapentin, and pregabalin. Second-line medications include tricyclic antidepressants, alone or in combination with anti-epileptic drugs. Third-line medications include ketamine, opioids, selective serotonin reuptake inhibitors, other antiepileptic drugs, intrathecal morphine with clonidine, and intrathecal baclofen.

Patients with localized pain symptoms may respond to topical lidocaine therapy. In diffuse and complex syndromes, initial drug therapy with gabapentin or nortriptyline is commenced at the lowest dose and then titrated gradually to desired analgesic effect with the least adverse effects. Incomplete or partial response to a drug after an adequate trial may be augmented by the addition of another drug with a different mechanism of action.

Neuroaugmentative Treatment

Neuroaugmentative treatment options for SCI pain include transcutaneous electric nerve stimulation, spinal cord stimulation, and deep brain stimulation, all of which have little evidence of efficacy.

Surgical Treatment

Of the many types of SCI pain, only a few can be successfully ameliorated with surgery. These include spinal fusion for stabilization of the spine, surgical decompression of nerve root compression, and drainage and shunting for syrinx, which may require subsequent detethering of the spinal cord. Other surgical treatments, including cordotomy, cordectomy, myelotomy, and dorsal root entry zone lesion (particularly for at-level neuropathic pain), have limited evidence of efficacy.

Spinal Rehabilitation

Rehabilitation therapy is one of the principal components of treatment to restore functional independence and improve the quality of life of patients with SCI. Yet there is very limited evidence demonstrating the efficacy of various rehabilitative treatments. Physical treatment includes exercise and hydrotherapy, postural reeducation, pressure relief, use of physical aids, such as crutches, orthotics and wheelchairs, and other physical modalities. Unfortunately, physical therapy does not help reduce neuropathic SCI pain.

Methods of Treatment

In one aspect the present invention provides a method of treating a disease, a disorder or an injury of the CNS in a subject in need thereof, which comprises administering directly to the subject's spinal cord at least one oligonucleotide compound directed to a target gene associated with the disease, the disorder or the injury of the CNS, via intraparenchymal delivery or lumbar puncture in an amount and over a period of time effective to treat the subject. Particular diseases, disorders and injuries are disclosed herein and include neuropathy, including diabetes associated neuropathy, hyperalgesia and allodynia.

Examples of target genes are disclosed herein. RhoA and TLR4 are particular target genes useful in carrying out the invention.

The treatment of any of neuropathy, including diabetes associated neuropathy, hyperalgesia and allodynia may require long term care and pain management modalities. The goal of pain management is to provide symptom relief and improve an individual's level of functioning in daily activities.

In another aspect, the present invention provides a method of attenuating expression of a target gene in a subject suffering from a disease, a disorder or an injury of the CNS, which comprises administering directly to the subject's spinal cord at least one oligonucleotide compound directed to a target gene associated with the disease, the disorder or the injury of the CNS, via intraparenchymal delivery or lumbar puncture in an amount and over a period of time effective to attenuate expression of the target gene. In some embodiments the methods further include at least one pharmacological agent, the disorder or the injury of the CNS, via intraparenchymal delivery or lumbar puncture in an amount and over a period of time effective to attenuate expression of the target gene.

In some embodiments the pharmacological agent is selected from a non-steroidal anti-inflammatory drug (NSAID), a steroidal anti-inflammatory drug, anti-inflammatory agent, an antibiotic, an anti-viral agent, a free radical scavenger, an anti-cancer agent and a chemotherapeutic agent.

In some embodiments the disease disorder or injury of the CNS is associated with expression of a gene selected from a nocireceptor, APP, MAPT, SOD1, BACE1, CASP3, TGM2, NFE2L3, TARDBP, ADRB1, CAMK2A, CBLN1, CDK5R1, GABRA1, MAPK10, NOS1, NPTX2, NRGN, NTS, PDCD2, PDE4D, PENK, SYT1, TTR, FUS, LRDD, CYBA, ATF3, ATF6, CASP2, CASP1, CASP7, CASP8, CASP9, HRK, C1QBP, BNIP3, MAPK8, MAPK14, Rac1, GSK3B, P2RX7, TRPM2, PARG, CD38, STEAP4, BMP2, GJA1, TYROBP, CTGF, ANXA2, RHOA, DUOX1, RTP801, RTP801L, NOX4, NOX1, NOX2 (gp91pho, CYBB), NOX5, DUOX2, NOXO1, NOXO2 (p47phox, NCF1), NOXA1, NOXA2 (p67phox, NCF2), p53 (TP53), HTRA2, KEAP1, SHC1, ZNHIT1, LGALS3, HI95, SOX9, ASPP1, ASPP2, CTSD, CAPNS1, FAS and FASLG, NOGO and NOGO-R; TLR1, TLR2, TLR3, TLR4, TLR6, TLR7, TLR8, TLR9, IL1bR, MYD88, TICAM, TIRAP, HSP47. Table A, hereinbelow, provides the gene identifier numbers (GI) and accession numbers for mRNA associated with each target gene.

| No. | Target gene | gi and accession numbers and full name |
|---|---|---|
| 1 | APP | > GI|41406053|ref|NM_000484.2| *Homo sapiens* amyloid beta (A4) precursor protein (APP), transcript variant 1, mRNA<br>>GI|41406054|ref|NM_201413.1| *Homo sapiens* amyloid beta (A4) precursor protein (APP), transcript variant 2, mRNA<br>> GI|41406056|ref|NM_201414.1| *Homo sapiens* amyloid beta (A4) precursor protein (APP), transcript variant 3, mRNA<br>>GI|228008402|ref|NM_001136129.2| *Homo sapiens* amyloid beta (A4) precursor protein (APP), transcript variant 5, mRNA<br>>GI|228008401|ref|NM_001136130.2| *Homo sapiens* amyloid beta (A4) precursor protein (APP), transcript variant 6, mRNA |
| 2 | MAPT | >GI|189409155|ref|NM_016835.3| *Homo sapiens* microtubule-associated protein tau (MAPT), transcript variant 1, mRNA<br>>GI|189409158|ref|NM_005910.4| (MAPT), transcript variant 2, mRNA<br>>GI|189409156|ref|NM_016834.3| (MAPT), transcript variant 3, mRNA<br>>GI|189409157|ref|NM_016841.3|, (MAPT), transcript variant 4, mRNA<br>>GI|294862254|ref|NM_001123067.3|, (MAPT), transcript variant 5, mRNA<br>>GI|294862257|ref|NM_001123066.3| (MAPT), transcript variant 6, mRNA |
| 3 | SOD1 | >GI|48762945|ref|NM_000454.4| *Homo sapiens* superoxide dismutase 1, soluble (SOD1), mRNA |
| 4 | BACE1 | >GI|46255011|ref|NM_012104.3| *Homo sapiens* beta-site APP-cleaving enzyme 1 (BACE1), transcript variant a, mRNA<br>>GI|46255013|ref|NM_138972.2| transcript variant b, mRNA<br>>GI|46255012|ref|NM_138971.2| transcript variant c, mRNA<br>>GI|46255014|ref|NM_138973.2| transcript variant d, mRNA |
| 5 | CASP3 | >GI|73622122|ref|NM_032991.2| *Homo sapiens* caspase 3, apoptosis-related cysteine peptidase (CASP3), transcript variant beta, mRNA<br>>GI|73622121|ref|NM_004346.3|, transcript variant alpha, mRNA |
| 6 | TGM2 | > GI|39777596|ref|NM_004613.2| *Homo sapiens* transglutaminase 2 (C polypeptide, protein-glutamine-gamma-glutamyltransferase) (TGM2), transcript variant 1, mRNA<br>>GI|39777598|ref|NM_198951.1| transcript variant 2, mRNA |
| 7 | NFE2L3 | >GI|225735556|ref|NM_004289.6| *Homo sapiens* nuclear factor (erythroid-derived 2)-like 3 (NFE2L3), mRNA |
| 8 | TARDBP | >GI|42741653|ref|NM_007375.3| *Homo sapiens* TAR DNA binding protein (TARDBP), mRNA |
| 9 | ADRB1 | >GI|110349783|ref|NM_000684.2| *Homo sapiens* adrenergic, beta-1-, receptor (ADRB1), mRNA |

| No. | Target gene | gi and accession numbers and full name |
|---|---|---|
| 10 | CAMK2A | >GI|212549564|ref|NM_015981.3| *Homo sapiens* calcium/calmodulin-dependent protein kinase II alpha (CAMK2A), transcript variant 1, mRNA<br>>GI|212549565|ref|NM_171825.2| (CAMK2A), transcript variant 2, mRNA |
| 11 | CBLN1 | >GI|4757921|ref|NM_004352.1| *Homo sapiens* cerebellin 1 precursor (CBLN1), mRNA |
| 12 | CDK5R1 | >GI|34304373|ref|NM_003885.2| *Homo sapiens* cyclin-dependent kinase 5, regulatory subunit 1 (p35) (CDK5R1), mRNA |
| 13 | GABRA1 | >GI|189083722|ref|NM_000806.5| *Homo sapiens* gamma-aminobutyric acid (GABA) A receptor, alpha 1 (GABRA1), transcript variant 1, mRNA<br>>GI|189083723|ref|NM_001127643.1| (GABRA1), transcript variant 2, mRNA<br>>GI|189083725|ref|NM_001127644.1| (GABRA1), transcript variant 3, mRNA<br>>GI|189083727|ref|NM_001127645.1| (GABRA1), transcript variant 4, mRNA<br>>GI|189083729|ref|NM_001127646.1| (GABRA1), transcript variant 5, mRNA<br>>GI|189083731|ref|NM_001127647.1 (GABRA1), transcript variant 6, mRNA<br>>GI|189083733|ref|NM_001127648.1| (GABRA1), transcript variant 7, mRNA |
| 14 | MAPK10 | >GI|257467587|ref|NM_002753.3| transcript variant 1, mRNA<br>>GI|257467594|ref|NM_138982.2| (MAPK10), transcript variant 2, mRNA<br>>GI|257467592|ref|NM_138980.2| (MAPK10), transcript variant 3, mRNA<br>>GI|257467593|ref|NM_138981.2| (MAPK10), transcript variant 4, mRNA |
| 15 | NOS1 | >GI|194239671|ref|NM_000620.2| *Homo sapiens* nitric oxide synthase 1 (neuronal) (NOS1), mRNA |
| 16 | NPTX2 | >GI|223671935|ref|NM_002523.2| *Homo sapiens* neuronal pentraxin II (NPTX2), mRNA |
| 17 | NRGN | >GI|187131237|ref|NM_006176.2| *Homo sapiens* neurogranin (protein kinase C substrate, RC3) (NRGN), transcript variant 1, mRNA<br>>GI|187131238|ref|NM_001126181.1| (NRGN), transcript variant 2, mRNA |
| 18 | NTS | >GI|31563516|ref|NM_006183.3| *Homo sapiens* neurotensin (NTS), mRNA |
| 19 | PDCD2 | >GI|21735591|ref|NM_002598.2| *Homo sapiens* programmed cell death 2 (PDCD2), transcript variant 1, mRNA<br>>GI|21735593|ref|NM_144781.1| (PDCD2), transcript variant 2, mRNA |
| 20 | PDE4D | >GI|157277987|ref|NM_001104631.1| *Homo sapiens* phosphodiesterase 4D, cAMP-specific (phosphodiesterase E3 dunce homolog, *Drosophila*) (PDE4D), transcript variant 1, mRNA<br>>GI|157277986|ref|NM_006203.4| (PDE4D), transcript variant 2, mRNA<br>>GI|259906419|ref|NM_001165899.1| (PDE4D), transcript variant 3, mRNA |
| 21 | PENK | >GI|208879445|ref|NM_001135690.1| *Homo sapiens* proenkephalin (PENK), transcript variant 1, mRNA<br>>GI|208879444|ref|NM_006211.3| (PENK), transcript variant 2, mRNA |
| 22 | SYT1 | >GI|209447071|ref|NM_005639.2| *Homo sapiens* synaptotagmin I (SYT1), transcript variant 1, mRNA<br>>GI|209447069|ref|NM_001135805.1| (SYT1), transcript variant 2, mRNA<br>>GI|209447072|ref|NM_001135806.1| (SYT1), transcript variant 3, mRNA |
| 23 | TTR | >GI|221136767|ref|NM_000371.3| *Homo sapiens* transthyretin (TTR), mRNA |
| 24 | FUS | >GI|270265814|ref|NM_004960.3| *Homo sapiens* fused in sarcoma (FUS), transcript variant 1, mRNA<br>>GI|270265815|ref|NR_028388.2| (FUS), transcript variant 2, non-coding RNA<br>>GI|283135200|ref|NM_001170634.1| (FUS), transcript variant 3, mRNA<br>>GI|283135172|ref|NM_001170937.1 (FUS), transcript variant 4, mRNA |
| 25 | LRDD | >GI|61742783|ref|NM_145886.2| *Homo sapiens* leucine-rich repeats and death domain containing (LRDD), transcript variant 1, mRNA<br>>GI|61742781|ref|NM_018494.3| (LRDD), transcript variant 2, mRNA<br>>GI|61742785|ref|NM_145887.2| (LRDD), transcript variant 3, mRNA |
| 26 | CYBA | >GI|68509913|ref|NM_000101.2| *Homo sapiens* cytochrome b-245, alpha polypeptide (CYBA), mRNA |
| 27 | ATF3 | >GI|719025341|ref|NM_001674.2| *Homo sapiens* activating transcription factor 3 (ATF3), transcript variant 1, mRNA<br>>GI|95102484|ref|NM_001030287.2| (ATF3), transcript variant 3, mRNA<br>>GI|95102482|ref|NM_001040619.1| (ATF3), transcript variant 4, mRNA |
| 28 | CASP2 | >GI|39995058|ref|NM_032982.2| *Homo sapiens* caspase 2, apoptosis-related cysteine peptidase (neural precursor cell expressed, developmentally down-regulated 2) (CASP2), transcript variant 1, mRNA<br>>GI|39995060|ref|NM_032983.2| (CASP2), transcript variant 3, mRNA |
| 29 | HRK | >GI|4504492|ref|NM_003806.1| *Homo sapiens* harakiri, BCL2 interacting protein (contains only BH3 domain) (HRK), mRNA |
| 30 | C1QBP | >GI|28872801|ref|NM_001212.3| *Homo sapiens* complement component 1, q subcomponent binding protein (C1QBP), nuclear gene encoding mitochondrial protein, mRNA |
| 31 | BNIP3 | >GI|7669480|ref|NM_004052.2| *Homo sapiens* BCL2/adenovirus E1B 19 kDa interacting protein 3 (BNIP3), nuclear gene encoding mitochondrial protein, mRNA |
| 32 | MAPK8 | >GI|20986522|ref|NM_139049.1| *Homo sapiens* mitogen-activated protein kinase 8 (MAPK8), transcript variant 1, mRNA<br>>GI|20986493|ref|NM_002750.2| (MAPK8), transcript variant 2, mRNA<br>>>GI|20986518|ref|NM_139046.1| (MAPK8), transcript variant 3, mRNA<br>>GI|20986520|ref|NM_139047.1| (MAPK8), transcript variant 4, mRNA |
| 33 | MAPK14 | >GI|194578902|ref|NM_001315.2| *Homo sapiens* mitogen-activated protein kinase 14 (MAPK14), transcript variant 1, mRNA |

-continued

| No. | Target gene | gi and accession numbers and full name |
|---|---|---|
| | | >GI|194578900|ref|NM_139012.2| (MAPK14), transcript variant 2, mRNA |
| | | >GI|194578904|ref|NM_139013.2| (MAPK14), transcript variant 3, mRNA |
| | | >GI|194578901|ref|NM_139014.2| (MAPK14), transcript variant 4, mRNA |
| 34 | Rac1 | >GI|156071503|ref|NM_006908.4| *Homo sapiens* ras-related C3 botulinum toxin substrate 1 (rho family, small GUP binding protein Rac1) (RAC1), transcript variant Rac1, mRNA |
| | | >GI|156071511|ref|NM_018890.3| (RAC1), transcript variant Rac1b, mRNA |
| 35 | GSK3B | >GI|225903415|ref|NM_002093.3| *Homo sapiens* glycogen synthase kinase 3 beta (GSK3B), transcript variant 1, mRNA |
| | | >GI|225903436|ref|NM_001146156.1| (GSK3B), transcript variant 2, mRNA |
| 36 | P2RX7 | >GI|34335273|ref|NM_002562.4| *Homo sapiens* purinergic receptor P2X, ligand-gated ion channel, 7 (P2RX7), mRNA |
| 37 | TRPM2 | >GI|67906812|ref|NM_003307.3| *Homo sapiens* transient receptor potential cation channel, subfamily M, member 2 (TRPM2), transcript variant L, mRNA |
| 38 | PARG | >GI|70610135|ref|NM_003631.2| *Homo sapiens* poly (ADP-ribose) glycohydrolase (PARG), mRNA |
| 39 | CD38 | >GI|38454325|ref|NM_001775.2| *Homo sapiens* CD38 molecule (CD38), mRNA |
| 40 | STEAP4 | >GI|100815814|ref|NM_024636.2| *Homo sapiens* STEAP family member 4 (STEAP4), mRNA |
| 41 | BMP2 | >GI|80861484|ref|NM_001200.2| *Homo sapiens* bone morphogenetic protein 2 (BMP2), mRNA |
| 42 | GJA1 | >GI|122939163|ref|NM_000165.3| *Homo sapiens* gap junction protein, alpha 1, 43 kDa (GJA1), mRNA |
| 43 | TYROBP | >GI|291045269|ref|NM_003332.3| *Homo sapiens* TYRO protein tyrosine kinase binding protein (TYROBP), transcript variant 1, mRNA |
| | | >GI|291045270|ref|NM_198125.2 (TYROBP), transcript variant 2, mRNA |
| | | >GI|291045271|ref|NM_001173514.1| (TYROBP), transcript variant 3, mRNA |
| | | >GI|291045273|ref|NM_001173515.1| (TYROBP), transcript variant 4, mRNA |
| | | >GI|291045275|ref|NR_033390.1| (TYROBP), transcript variant 5, non-coding RNA |
| 44 | CTGF | >GI|98986335|ref|NM_001901.2| *Homo sapiens* connective tissue growth factor (CTGF), mRNA |
| 45 | ANXA2 | GI|216547999|ref|NM_001002858.2| (ANXA2), transcript variant 1, mRNA |
| | | >GI|50845385|ref|NM_001002857.1| (ANXA2), transcript variant 2, mRNA |
| | | >GI|50845389|ref|NM_004039.2| (ANXA2), transcript variant 3, mRNA |
| | | >GI|216547993|ref|NM_001136015.2| (ANXA2), transcript variant 4, mRNA |
| 46 | RHOA | >gi:50593005/NM_001664.2 *Homo sapiens* ras homolog gene family, member A (RHOA), mRNA. |
| 47 | DUOX1 | <SEQ_ID_NO: X>GI|28872749|ref|NM_017434.3| *Homo sapiens* dual oxidase 1 (DUOX1), transcript variant 1, mRNA |
| | | <SEQ_ID_NO: X>GI|28872750|ref|NM_175940.1| (DUOX1), transcript variant 2, mRNA |
| 48 | RTP801 (DDIT4) | GI|56676369|ref|NM_019058.2| *Homo sapiens* DNA-damage-inducible transcript 4 (DDIT4), mRNA |
| 49 | RTP801L (DDIT4L) | GI|307691170|ref|NM_145244.3| *Homo sapiens* DNA-damage-inducible transcript 4-like (DDIT4L), mRNA |
| 50 | NOX4 | >GI|219842344|ref|NM_016931.3| *Homo sapiens* NADPH oxidase 4 (NOX4), transcript variant 1, mRNA |
| | | >GI|219842345|ref|NM_001143836.1| (NOX4), transcript variant 2, mRNA |
| | | >GI|219842347|ref|NM_001143837.1| (NOX4), transcript variant 3, mRNA |
| 51 | NOX1 | >GI|148536872|ref|NM_007052.4| *Homo sapiens* NADPH oxidase 1 (NOX1), transcript variant NOH-1L, mRNA |
| | | >GI|148536874|ref|NM_013955.2|, transcript variant NOH-1Lv, mRNA |
| 52 | NOX2 (gp91pho, CYBB) | >GI|6996020|ref|NM_000397.2| *Homo sapiens* cytochrome b-245, beta polypeptide (chronic granulomatous disease) (CYBB), mRNA |
| 53 | NOX5 | >GI|20127623|ref|NM_024505.2| *Homo sapiens* NADPH oxidase, EF-hand calcium binding domain 5 (NOX5), mRNA |
| 54 | DUOX2 | >GI|132566531|ref|NM_014080.4| *Homo sapiens* dual oxidase 2 (DUOX2), mRNA |
| 55 | NOXO1 | >GI|34222190|ref|NM_144603.2| *Homo sapiens* NADPH oxidase organizer 1 (NOXO1), transcript variant a, mRNA |
| | | >GI|41281827|ref|NM_172168.1| transcript variant c, mRNA |
| | | >GI|41281810|ref|NM_172167.1| transcript variant b, mRNA |
| 56 | NOXO2 (p47phox, NCF1) | >GI|115298671|ref|NM_000265.4| *Homo sapiens* neutrophil cytosolic factor 1 (NCF1), mRNA |
| 57 | NOXA1 | >GI|41393186|ref|NM_006647.1| *Homo sapiens* NADPH oxidase activator 1 (NOXA1), mRNA |
| 58 | NOXA2 (p67phox, NCF2) | >GI|189083740|ref|NM_000433.3| *Homo sapiens* neutrophil cytosolic factor 2 (NCF2), transcript variant 1, mRNA |
| | | >GI|189083741|ref|NM_001127651.1| (NCF2), transcript variant 2, mRNA |
| 59 | p53 (TP53) | >GI|187830767|ref|NM_000546.4| *Homo sapiens* tumor protein p53 (TP53), transcript variant 1, mRNA |
| | | >GI|187830776|ref|NM_001126112.1| (TP53), transcript variant 2, mRNA |
| | | >GI|187830854|ref|NM_001126114.1| (TP53), transcript variant 3, mRNA |

-continued

| No. | Target gene | gi and accession numbers and full name |
|---|---|---|
| | | >GI|187830822|ref|NM_001126113.1| (TP53), transcript variant 4, mRNA |
| | | >GI|187830893|ref|NM_001126115.1| (TP53), transcript variant 5, mRNA |
| | | >GI|187830900|ref|NM_001126116.1| (TP53), transcript variant 6, mRNA |
| | | >GI|187830908|ref|NM_001126117.1| (TP53), transcript variant 7, mRNA |
| 60 | HTRA2 | >GI|73747817|ref|NM_013247.4| *Homo sapiens* HtrA serine peptidase 2 (HTRA2), nuclear gene encoding mitochondrial protein, transcript variant 1, mRNA |
| | | >GI|73747818|ref|NM_145074.2| transcript variant 2, mRNA |
| 61 | KEAP1 | >GI|45269144|ref|NM_203500.1| *Homo sapiens* kelch-like ECH-associated protein 1 (KEAP1), transcript variant 1, mRNA |
| | | >GI|45269143|ref|NM_012289.3| (SHC1), transcript variant 2, mRNA |
| | | >GI|194239663|ref|NM_001130040.1| (SHC1), transcript variant 3, mRNA |
| | | >GI|194239667|ref|NM_001130041.1| (SHC1), transcript variant 4, mRNA |
| 62 | SHC1 | >GI|52693920|ref|NM_183001.3| *Homo sapiens* SHC (Src homology 2 domain containing) transforming protein 1 (SHC1), transcript variant 1, mRNA |
| | | >GI|34147725|ref|NM_003029.3| transcript variant 2, mRNA |
| 63 | ZNHIT1 | >GI|37594439|ref|NM_006349.2| *Homo sapiens* zinc finger, HIT type 1 (ZNHIT1), mRNA |
| 64 | LGALS3 | >GI|115430222|ref|NM_002306.2| *Homo sapiens* lectin, galactoside-binding, soluble, 3 (LGALS3), transcript variant 1, mRNA |
| | | >GI|115430224|ref|NR_003225.1| (LGALS3), variant 2, transcribed RNA |
| | | >GI|294345474|ref|NM_001177388.1| (LGALS3), transcript variant 3, mRNA |
| 65 | HI95 (SESN2) | >GI|32454742|ref|NM_031459.3| *Homo sapiens* sestrin 2 (SESN2), mRNA |
| 66 | SOX9 | >GI|37704387|ref|NM_000346.2| *Homo sapiens* SRY (sex determining region Y)-box 9 (campomelic dysplasia, autosomal sex-reversal) (SOX9), mRNA |
| 67 | ASPP1 (PPP1R13B) | >GI|121114286|ref|NM_015316.2| *Homo sapiens* protein phosphatase 1, regulatory (inhibitor) subunit 13B (PPP1R13B), mRNA |
| 68 | CTSD | >GI|23110949|ref|NM_001909.3| *Homo sapiens* cathepsin D (CTSD), mRNA |
| 69 | CAPNS1 | >GI|51999152|ref|NM_001749.2| *Homo sapiens* calpain, small subunit 1 (CAPNS1), transcript variant 1, mRNA |
| | | >GI|51999150|ref|NM_001003962.1| transcript variant 2, mRNA |
| 70 | FAS | >GI|23510419|ref|NM_000043.3| *Homo sapiens* Fas (TNF receptor superfamily, member 6) (FAS), transcript variant 1, mRNA |
| | | >GI|23510420|ref|NM_152871.1| transcript variant 2, mRNA |
| | | >GI|23510422|ref|NM_152872.1| transcript variant 3, mRNA |
| | | >GI|23510424|ref|NM_152873.1| transcript variant 4, mRNA |
| | | >GI|23510428|ref|NM_152875.1| transcript variant 5, mRNA |
| | | >GI|23510430|ref|NM_152876.1| transcript variant 6, mRNA |
| | | >GI|23510433|ref|NM_152877.1| transcript variant 7, mRNA |
| | | >GI|23510426|ref|NM_152874.1| transcript variant 8, mRNA |
| 71 | FASLG | >GI|4557328|ref|NM_000639.1| *Homo sapiens* Fas ligand (TNF superfamily, member 6) (FASLG), mRNA |
| 72 | CAPN1 | >GI|12408655|ref|NM_005186.2| *Homo sapiens* calpain 1, (mu/I) large subunit (CAPN1), mRNA |
| 73 | FADD | >>GI|215820647|ref|NM_003824.3| *Homo sapiens* Fas (TNFRSF6)-associated via death domain (FADD), mRNA |
| 74 | CASP1 | > GI|73622114ref|NM_033292.2| *Homo sapiens* caspase 1, apoptosis-related cysteine peptidase (interleukin 1, beta, convertase) (CASP1), transcript variant alpha, mRNA |
| | | > GI|73622112|ref|NM_001223.3| transcript variant beta, mRNA |
| | | > GI|73622118|ref|NM_033293.2| transcript variant gamma, mRNA |
| | | > GI|73622111|ref|NM_033294.2 transcript variant delta, mRNA |
| | | > GI|73622117|ref|NM_033295.2| transcript variant epsilon, mRNA |
| 75 | CASP7 | > GI|73623014 |ref|NM_033340.2 | *Homo sapiens* caspase 7, apoptosis-related cysteine peptidase (CASP7), transcript variant beta, mRNA |
| | | SEQ ID NO: 123 > GI|73623016 ref|NM_033339.3 transcript variant gamma, mRNA |
| 76 | CASP8 | > GI|122056470|ref|NM_001228.4| *Homo sapiens* caspase 8, apoptosis-related cysteine peptidase (CASP8), transcript variant A, mRNA |
| | | > GI|122056471|ref|NM_033356.3| transcript variant C, mRNA |
| 77 | CASP9 | > GI|14790123|ref|NM_001229.2| *Homo sapiens* caspase 9, apoptosis-related cysteine peptidase (CASP9), transcript variant alpha, mRNA |
| | | > GI|14790127|ref|NM_032996.1| transcript variant beta, mRNA |
| 78 | ASPP2 (TP53BP2) | >GI|112799848|ref|NM_001031685.2| *Homo sapiens* tumor protein p53 binding protein, 2 (TP53BP2), transcript variant 1, mRNA |
| | | >GI|112799845|ref|NM_005426.2| transcript variant 2, mRNA |
| 79 | RTN4 (NogoA) | > GI|47519458|ref|NM_020532.4| *Homo sapiens* reticulon 4 (RTN4), transcript variant 1, mRNA |
| | | > GI|47519507|ref|NM_153828.2| (RTN4), transcript variant 2, mRNA |
| | | > GI|47519538|ref|NM_007008.2| (RTN4), transcript variant 3, mRNA |
| | | > GI|47519489|ref|NM_207520.1| (RTN4), transcript variant 4, mRNA |
| | | > GI|47519561|ref|NM_207521.1| (RTN4), transcript variant 5, mRNA |
| 80 | RTN4R (NGR) | > GI|47519383|ref|NM_023004.5| *Homo sapiens* reticulon 4 receptor (RTN4R), mRNA |
| 81 | TLR1 | > GI| 41350336|ref| NM_003263| *Homo sapiens* toll-like receptor 1 (TLR1), mRNA |

| No. | Target gene | gi and accession numbers and full name |
|---|---|---|
| 82 | TLR2 | >GI|68160956|ref|NM_003264.3| *Homo sapiens* Toll-like receptor 2 (TLR2), mRNA |
| 83 | TLR4 | > GI|207028620|ref|NM_138554.3 | *Homo sapiens* Toll-like receptor 4 (TLR4), mRNA, transcript variant 1<br>>GI|207028451|ref|NR_024168.1||(TLR4), transcript variant 3 (non-coding)<br>>GI|207028550|ref|NR_024169.1| |(TLR4), transcript variant 4 (non-coding) |
| 84 | TLR3 | >GI|19718735|ref| NM_003265.2| *Homo sapiens* toll-like receptor 3 (TLR3), mRNA |
| 85 | TLR6 | >GI| 262527233|ref| NM_006068.3| *Homo sapiens* toll-like receptor 6 (TLR6), mRNA |
| 86 | TLR7 | > GI| 67944638|ref| NM_016562.3| *Homo sapiens* toll-like receptor 7 (TLR7), mRNA |
| 87 | TLR8 | >GI| 257196253|ref| NM_138636.4| *Homo sapiens* toll-like receptor 8 (TLR8), mRNA |
| 88 | TLR9 | >GI| 20302169|ref| NM_017442.2| *Homo sapiens* toll-like receptor 9 (TLR9), transcript variant A, mRNA |
| 89 | IL1R | >GI| 27894331|ref| NM_000877.2| *Homo sapiens* interleukin 1 receptor, type I (IL1R1), mRNA |
| 90 | MYD88 | >GI|197276653|ref|NM_002468.4| *Homo sapiens* myeloid differentiation primary response gene (88) (MYD88), mRNA |
| 91 | TICAM1 | >GI|197209874|ref|NM_182919.2| *Homo sapiens* Toll-like receptor adaptor molecule 1 (TICAM1), mRNA |
| 92 | TIRAP | >GI|89111121|ref|NM_001039661.1| *Homo sapiens* toll-interleukin 1 receptor (TIR) domain containing adaptor protein (TIRAP), transcript variant 3, mRNA<br>>GI|89111123|ref|NM_148910.2| transcript variant 2, mRNA |
| 93 | SERPINH1 (HSP47) | >GI|32454740|ref|NM_001235.2|*Homo sapiens* serpin peptidase inhibitor, clade H (heat shock protein 47), member 1, (collagen binding protein 1) (SERPINH1), mRNA |

A specific mRNA sequence is associated with each GI and accession number. The description of the various aspects and embodiments is provided with reference to exemplary target genes. However, the various aspects and embodiments are also directed to related target genes, such as homolog genes and transcript variants, and polymorphisms (e.g., single nucleotide polymorphism, (SNPs)) associated with certain target genes.

In some embodiments of the invention, inhibition of any one of the following target genes, TGM2, NFE2L3, TARDBP, ADRB1, CAMK2A, CBLN1, CDK5R1, GABRA1, MAPK10, NOS1, NPTX2, NRGN, NTS, PDCD2, PDE4D, PENK, SYT1, TTR, FUS, LRDD, CYBA, ATF3, ATF6, CASP2, CASP1, CASP7, CASP8, CASP9, HRK, C1QBP, BNIP3, MAPK8, MAPK14, Rac1, GSK3B, P2RX7, TRPM2, PARG, CD38, STEAP4, BMP2, GJA1, TYROBP, CTGF, ANXA2, RHOA, DUOX1, RTP801, RTP801L, NOX4, NOX1, NOX2 (gp91pho, CYBB), NOX5, DUOX2, NOXO1, NOXO2 (p47phox, NCF1), NOXA1, NOXA2 (p67phox, NCF2), p53 (TP53), HTRA2, KEAP1, SHC1, ZNHIT1, LGALS3, HI95, SOX9, ASPP1, ASPP2, CTSD, CAPNS1, FAS and FASLG, NOGO and NOGO-R; TLR1, TLR2, TLR3, TLR4, TLR6, TLR7, TLR8, TLR9, IL1bR, MYD88, TICAM, TIRAP, HSP47 is useful in alleviating, preventing or treating neuropathic pain.

In some embodiments the target gene is selected from TGM2, MAPK10, PDE4D, CYBA, C1QBP, MAPK8, MAPK14, Rac1, GSK3B, P2RX7, TRPM2, PARG, CD38, STEAP4, BMP2, GJA1, TYROBP, CTGF, ANXA2, RHOA, DUOX1, NOX4, NOX1, NOX2 (gp91pho, CYBB), NOX5, DUOX2, NOXO1, NOXO2 (p47phox, NCF1), NOXA1, NOXA2 (p67phox, NCF2, KEAP1, SHC1, LGALS3, SOX9, NOGO and NOGO-R; TLR1, TLR2, TLR3, TLR4, TLR6, TLR7, TLR8, TLR9, IL1bR, MYD88, TICAM, TIRAP, or HSP47.

In some preferred embodiments the target gene is selected from MAPK10, PDE4D, CYBA, C1QBP, MAPK8, MAPK14, P2RX7, CD38, STEAP4, TYROBP, ANXA2, RHOA, DUOX1, NOX4, NOX1, NOX2 (gp91pho, CYBB), NOX5, DUOX2, NOXO1, NOXO2 (p47phox, NCF1), NOXA1, NOXA2 (p67phox, NCF2, KEAP1, SHC1, LGALS3, SOX9, NOGO, NOGO-R, TLR1, TLR2, TLR3, TLR4, TLR6, TLR7, TLR8, TLR9, IL1bR, MYD88, TICAM, TIRAP, or HSP47.

In some preferred embodiments the target gene is selected from RhoA, TLR4, LGALS and P2RX7.

In preferred embodiments the therapeutic oligonucleotide is a double stranded RNA (dsRNA) compound. In some embodiments the dsRNA is a siRNA compound, preferably a chemically modified siRNA according to the disclosure provided herein. In preferred embodiments the subject being treated is a warm-blooded animal and, in particular a mammal, and preferably a human. Sequences useful in generating siRNA compounds are identified using design rules for selecting siRNA, and may be identified using an algorithm, available online for example, on the worldwide web.

"Treating a subject" refers to administering to the subject a therapeutic substance effective to alleviate symptoms associated with a disease or condition, to delay the onset of the disease, to slow the progress of the disease, to lessen the severity or cure the disease, or to prevent the disease from occurring. "Treatment" refers to both therapeutic treatment and prophylactic or preventative measures, wherein the object is to prevent a disorder, to slow the progress of a disease or to reduce the symptoms of a disorder. Those in need of treatment include those already experiencing the disease or condition, those at risk of or prone to having the disease or condition, and those in which the disease or condition is to be prevented. The compositions of the invention are administered before, during or subsequent to the onset of the disease or condition.

Additionally, the invention provides a method of down-regulating the expression of a target gene by at least 30%, at least 40%, at least 50% as compared to a control, comprising contacting a target gene mRNA with one or more of the chemically modified siRNA compound of the pharmaceutical compositions of the present invention.

In some embodiments the method comprises administering to a subject a therapeutic oligonucleotide, for example an siRNA once, twice, three times, or four times daily. In some embodiments a therapeutic oligonucleotide is administered continuously over a period of 1 day to 14 days. In other embodiments a therapeutic oligonucleotide is administered once by lumbar injection, within 48 hours of CNS or PNS injury, preferably within 40 hours, 32 hours, or within 24 hours of injury. In other embodiments a therapeutic oligonucleotide is administered once by lumbar injection, within 48 hours of CNS or PNS injury, preferably within 40 hours, 32 hours, or within 24 hours of injury and then administered once every two weeks, or once every month. Exemplary durations of treatment include at least about 3 days, from 1 day to 1 month, from 1 day to about two weeks, from two weeks to 1 month, up to about 6 months, up to about 12 months or even longer. In an embodiment of the treatment method, the administration is over a duration of time effective to result in elimination or reduction of pain.

The attending physician will decide use of the therapeutic compounds and compositions within the scope of sound medical judgment.

The specific dose level and administration modality necessary to achieve a positive therapeutic response in treatment of pain, such as preventing, diminishing, alleviating or eliminating pain in a subject depends upon a variety of factors including the scope and severity of the disorder or injury; the composition used; certain information about the patient including age, sex, body weight, general health; the time of administration, route of administration, and rate of excretion of the specific compound employed; the duration of the treatment; drugs used in combination with the specific compound employed; and factors well-known in the medical arts. The total daily dose of the compounds administered to a subject, for example a human subject, ranges from about 0.10 ug/kg body weight to about 25 mg/kg body weight; or from about 0.10 ug/kg body weight to about 10 mg/kg body weight, or from about 1.0 ug/kg body weight to about 10 mg/kg body weight, or from about 10.0 ug/kg body weight to about 10 mg/kg body weight. ("ug/kg" refers to microgram therapeutic agent per kilogram body weight).

In one aspect a kit is provided for treating spinal cord injury, the kit comprising any one of the compositions of the invention in an effective amount to treat spinal cord injury. In one aspect a kit is provided for treating or preventing allodynia, the kit comprising any one of the compositions of the invention in an effective amount to treat or prevent allodynia. In one embodiment, the kit is used with a drug delivery pump. In one embodiment, the kit is used with a syringe for intrathecal or intraspinal delivery.

Delivery to the Spinal Cord

Delivery of a drug into the intradural or intrathecal space is aimed at delivering the drug to a specific target within the spinal cord, and in concentrations within the spinal cord that cannot be achieved with systemic delivery and using a method that is less invasive than for example an implanted drug delivery system or surgery. The drug may also be restricted to its spinal delivery site, thereby avoiding dose-limiting side effects or toxicities. Chemical agents delivered to the intradural or intrathecal space have been shown previously to enter the plasma and achieve significant systemic concentrations differing from drug to drug. Addition of liposomes or other formulations may greatly increase the systemic concentration of drugs delivered to the spinal cord. (Spinal Drug Delivery, Elsevier, May 1999, T. L. Yaksh Ed.).

The siRNAs of the present invention are preferably naked i.e. unformulated and thus when administered intraparenchymally or intrathecally are readily taken up by the cells of the spinal cord.

Intraparenchymal Delivery

The parenchyma is the nervous tissue of the spinal cord, which is bathed in the cerebrospinal fluid and surrounded by the dura matter within the vertebral bones. In intraparenchymal delivery, drugs are injected directly or via a catheter across the dura matter into the nervous tissue. The drugs may be injected in bolus form or delivered continuously.

Intrathecal Delivery

The spinal intrathecal space is the space surrounding the spinal cord in the spinal canal. In intrathecal delivery, the drug is injected directly into the cerebrospinal fluid.

Differences between intraparenchymal delivery and intrathecal delivery include:

Only small volumes can be injected into the parenchyma while the intrathecal space is quite large at the lumbar enlargement, which allows much larger volumes to be injected.

Intraparenchymal delivery requires a laminectomy whereas and intrathecal delivery can be performed at the lumbar enlargement by injection between the lumbar vertebrae without disrupting them.

The present application provides two methods of delivery of siRNAs into the injured spinal cord and shows uptake of these agents into many different types of cells in and around the injury site. Moreover, injection of the siRNA into the injured spinal cord improved walking behavior using both methods and reduced pain sensitivity in at least one method. These results have therapeutic implications for mammalian subjects including human and animal patients and provide multiple delivery methods for improved function in spinal cord injury or disease patients. A combination of these methods may be even more beneficial. In addition, the lack of observed non-specific side effects indicates that combination of different siRNAs directed against different targets is feasible as a combination therapy against multiple targets simultaneously.

Numerous publications and patent documents, including both published applications and issued patents, are cited throughout the specification in order to describe the state of the art to which this invention pertains. Each of these citations is incorporated herein by reference as though set forth in full.

The invention is further defined by reference to the examples describing in detail the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

General Methods in Molecular Biology

Standard molecular biology techniques known in the art and not specifically described were generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683, 202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry can be used for detection of cells containing specific DNA and mRNA sequences (Testoni et al., 1996, Blood 87:3822.) Methods of performing RT-PCR are also well known in the art.

Oligonucleotide Sequences

Oligonucleotide sequences useful in generating dsRNA compounds including siRNA compounds are identified using design rules for selecting siRNA, and may be identified using an algorithm, available online for example, on the worldwide web. In a non-limiting example, the following website provides a list of available free online siRNA services: http://www.rnaiweb.com/RNAi/RNAi_Web_Resources/RNAi_Tools_Software/Online_si RNA Design Tools/index.html. Additional oligonucleotide sequences useful in generating dsRNA, in particular siRNA, may be selected from sequences disclosed in PCT patent publications WO 2008/050329, WO 2008/152636, and WO 2009/044392, assigned to an applicant of the present invention and hereby incorporated by reference in their entirety.

The Sequence Listing filed electronically herewith is hereby incorporated by reference in its entirety (File Name: 210_PCT1_ST25.txt; Date Created: Nov. 8, 2010; File Size: 26.00 Kb.) siRNA synthesis, modifications, activity and nuclease stability All siRNA molecules used in this study were stabilized by alternating 2'O-methylation. Specifically 2'O-methyl groups were present in all odd nucleotides of the antisense strands and in all even nucleotides of the sense strands (BioSpring, Frankfurt Germany) Cy3.5-labeled siRNA used for imaging studies had sequence 5'-GUGCCAACCUGAUGCAGCU-3' (SEQ ID NO:9, sense strand) siRNA against GFP (siGFP) was as previously described (Hamar et al., 2004). Active siRNA against RhoA (siRhoA) used in the in vivo studies had the sequence 5'- GCCACUUAAUGUAUGUUAC-3' (SEQ ID NO: 5; sense strand). Active siRNA against TLR4 (siTLR4) used in the in vivo studies had the sequence 5' GAGUUCAGGUUAACAUAUA 3' (SEQ ID NO:7, sense strand). The knockdown efficacy of siRhoA and siTLR4 were tested in human HeLa and rat REF52 cells by transfection of siRNA using Lipofectamine™2000 (Invitrogen, Calif.) according to the manufacturer's instructions. Target gene knockdown was determined by quantitative real-time—PCR (q-RT-PCR).

Example 1

Cellular Localization of siRNAs in Rat Spinal Cord Following Spinal Cord Injury and Intraparenchymal Delivery To develop siRNA therapies in spinal cord injury (SCI), the cells which incorporated labeled siRNA were identified. siRNAs conjugated with Cy3 as well as a specific sequence conjugated with Cy3.5 (REDD14/Cy3.5) demonstrated incorporation into similar cell populations including motor- neurons, macrophages, white matter axons, as well as neurons in the dorsal root and endothelial cells as shown in FIGS. 1A-1F. Thus, the siRNA is taken up by many of the cells where RhoA action has been implicated in SCI including neurons, astrocytes, microglia/macrophages and endothelial cells (D'Alessandri et al., 1995; Dubreuil et al., 2003. J Cell Biol 162(2): 233-43; Erschbamer et al., 2005. J Comp Neurol 484(2): 224-33; Yune et al., 2007. J Neurosci. 2007 Jul. 18;27 (29):7751-61; Fu et al., 2007; Pixley et al., 2005. J Cell Sci. 2005 May 1;118(Pt 9):1873-83.; Schreibelt et al., 2007. FASEB J. 2007 November;21(13):3666-76.; Schwab et al., 2004. Science 295(5557): 1029-31).

Figure 2B:
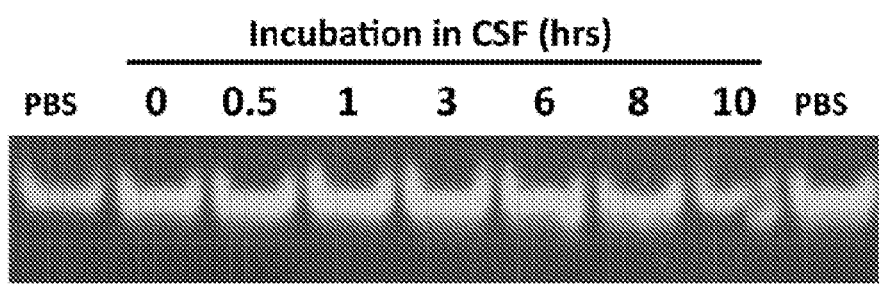
Figure 3A:
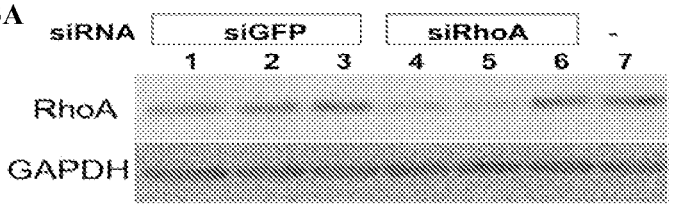
FIGS. 3A-3C. Effects of siRNA treatments on RhoA protein and functional recovery after SCI. Three (3) µg of siRhoA or siGFP were injected into the parenchymal tissue in 3 sites and then the cords were contused using the 12.5 weight drop in the rat MASCIS model for SCI. At one week following SCI and treatment, siRhoA treated rats showed reduced immunoblotting with antibodies against RhoA; immunoblot of GAPDH in the same lanes confirmed equal protein loadings (FIG. 3A). Therapeutic effects of a 3 ug intraspinal injection of siRhoA compared to siGFP controls were tested using the 12.5 and 25 mm weight drops. siRhoA treated rats showed significant (p-value=0.0098) locomotor BBB improvement compared to siGFP controls in the 12.5 mm contusion injury (FIG. 3B) when analyzed by ANOVA post-hoc repeated measures (n=6). A similar trend in locomotor improvement was observed with the more severe 25 mm contusion injury (FIG. 3C) but the differences observed were not statistically significant (n=6).
Figure 3B:
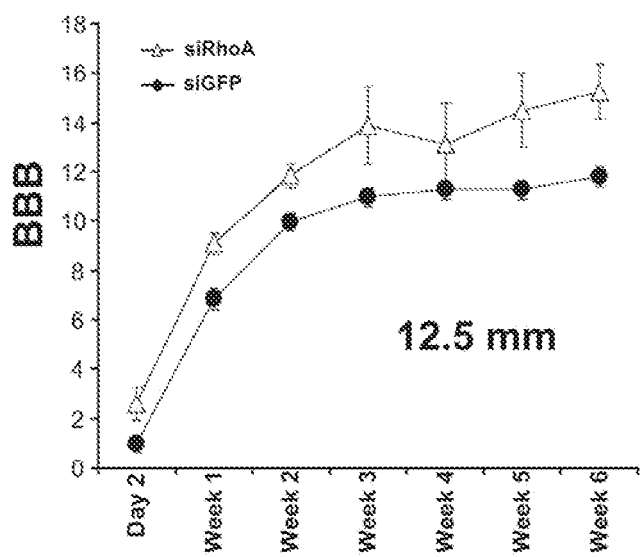

FIG. 2 shows siRNA compounds designed and verified for their knockdown of RhoA that were assessed using cells in vitro. The validated RHOA_4 compound was then used for its anticipated neuroprotective, anti-inflammatory and neuroregenerative abilities in vivo as shown in FIG. 3A. Locomotor BBB analysis was followed for 6 weeks and significant locomotor improvement following SCI and intraspinal injections of siRhoA were observed compared to siGFP as a control as shown in FIG. 3B. The effect indicating improvement of BBB walking scores was observed at the earliest times tested. Without wishing to be bound to theory this may suggest that the siRNA effect is due to protective mechanisms in addition to promoting regeneration, which may require longer times for axons to grow.

Figure 4:
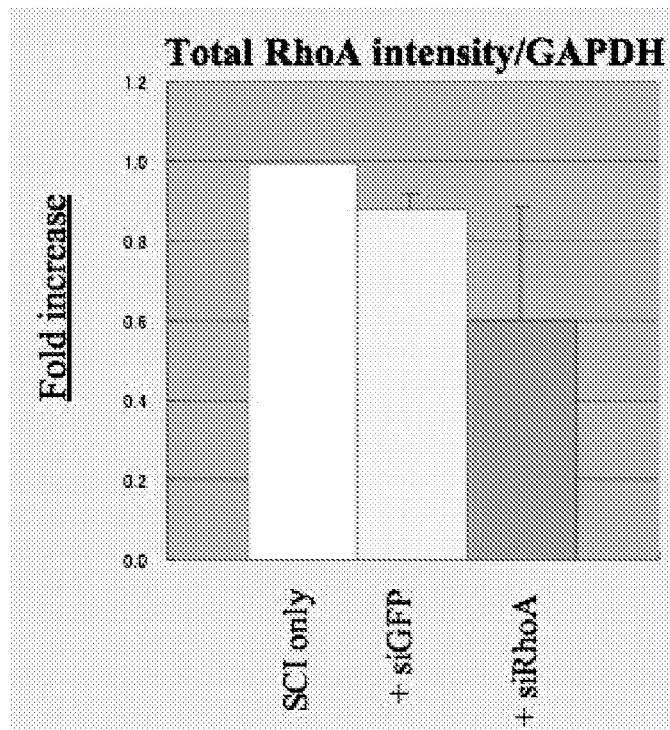
FIG. 4. Effects of siRNA treatments on RhoA protein measured by immunoblotting in the central 5 mm SCI site. Immediately after contusion using the 12.5 weight drop in the MASCIS model for SCI, 3 µg of siRhoA or siGFP were injected into the parenchymal tissue (1 µl intraspinal injections of 1 µg/µl in 3 sites as in FIG. 3. At one week following SCI and treatment, siRhoA treated rats show reduced average intensities after imunoblotting with antibodies against RhoA protein when normalized to intensities of GAPDH in the same lanes.
Figure 5:
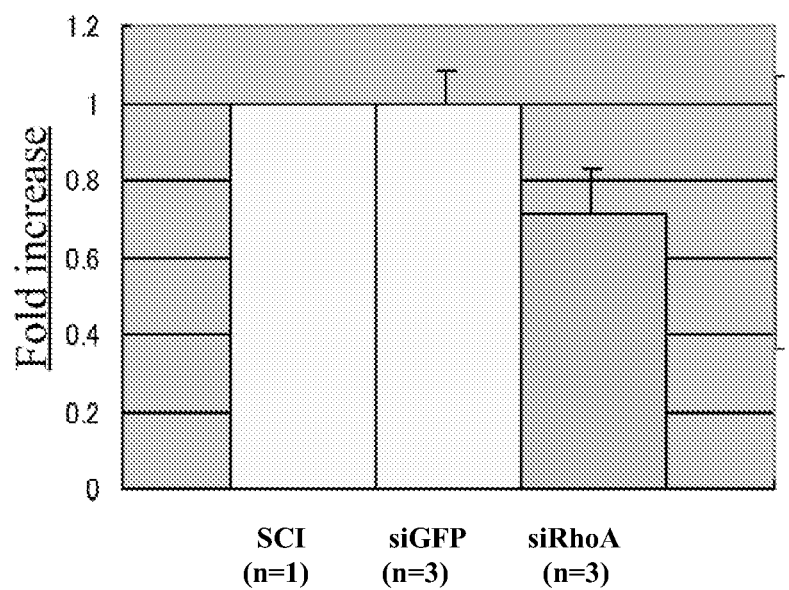
FIG. 5. Effects siRNA treatments on RhoA protein measured by ELISA in the central 5 mm SCI site. Immediately after contusion using the 12.5 weight drop in the MASCIS model for SCI, 3 µg of siRhoA or siGFP were injected into the parenchymal tissue (1 µl intraspinal injections of 1 µg/µl in 3 sites. At one week following SCI and treatment, siRhoA treated rats show reduced average intensities after ELISA when normalized to the average signals in rats treated with SCI only. Lower levels of RhoA protein were detected after RhoA siRNA treatment by comparison to the GFP siRNA control.

To analyze the ability of the siRNA to alter RhoA protein levels, proteins were extracted from 5 mm segments of spinal cord tissues and measured relative levels of RhoA protein after immunblotting. The levels of RhoA proteins were lower in the injected contusion sites that were treated with siRhoA by comparison to GFP controls as shown in FIG. 4, indicating inhibition of RhoA protein induction one week after contusion. Analysis by enzyme linked immunoassays confirmed lower levels of RhoA immunnoreactivity in the siRhoA treated samples (FIG. 5).

To compare intraparenchymal with intrathecal delivery, the Cy3.5 labeled siRNA (REDD14/Cy3.5) was applied using bolus administration to the lumbar enlargement one day after contusion. Results in FIGS. 6A-6G show widespread dye incorporation into the spinal cord at the injury center as well as in adjacent rostral and caudal regions but not at distant cervical sites. The siRNA penetrated into the white matter as well as the gray matter. Thus, intrathecal delivery in the lumbar region yielded preferential uptake of siRNA in and around the injury site in the thoracic region of the spinal cord.

Figure 7A:
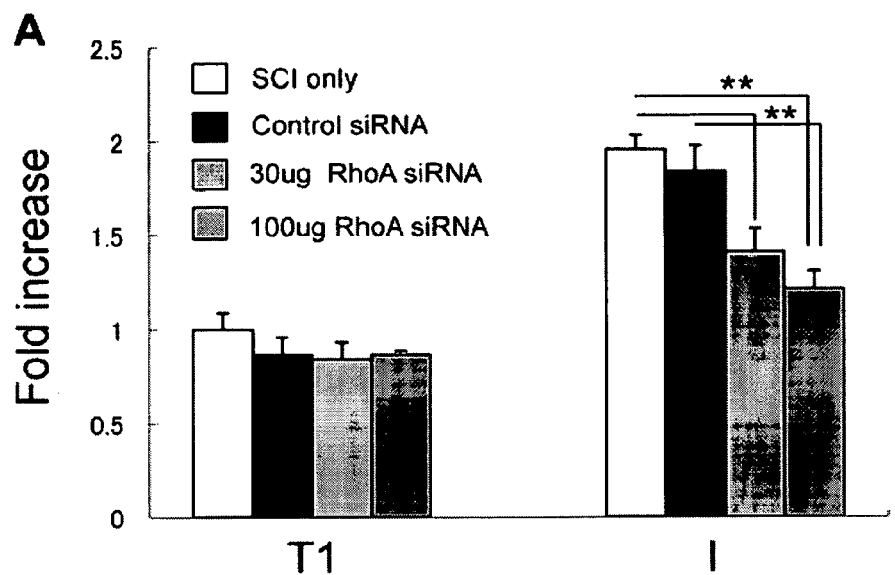
FIGS. 7A-7B Inhibition of RhoA mRNA 3 days after siRNA injection via lumbar puncture. Rats were injured with the MASCIS Impactor using a 12.5 mm weight drop (Hasegawa et al., 2005) and injected one day later via lumbar puncture with siRNAs.
Figure 7B:
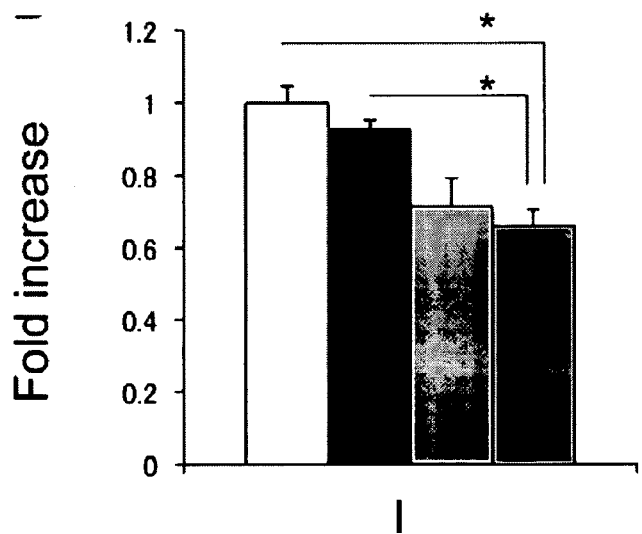

The ability of the siRNA to inhibit SCI-induced increase in RhoA mRNA was measured by Quantitative RT PCR. One day after contusion siRNA was injected via lumbar puncture and three days later spinal cord tissues were analyzed for relative levels of RhoA mRNA. Results in FIGS. 7A and 7B show that siRhoA treatment reduced average intensities when 30 and 100 μg were injected. "T1" refers to level T1 of the spine, and "I" refers to the Injury site.

Figure 8:
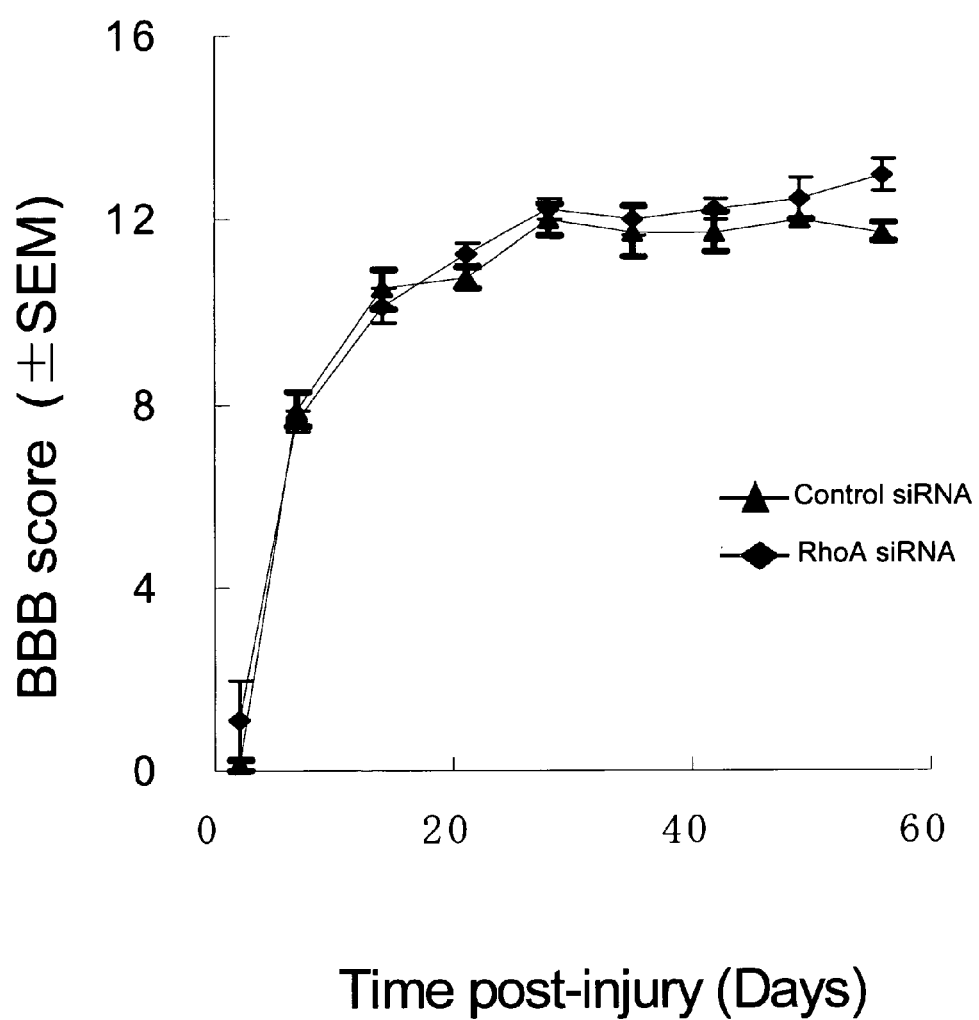
FIG. 8. Functional Recovery of Rat Hindlimb Walking (BBB) following lumbar puncture (L3/4) injection. After 12.5 mm contusion injury contusion in MASCIS model for SCI, siRhoA treatment showed improvement by comparison to siGFP controls at 8 weeks (diamond vs. triangle).
Figure 9A:
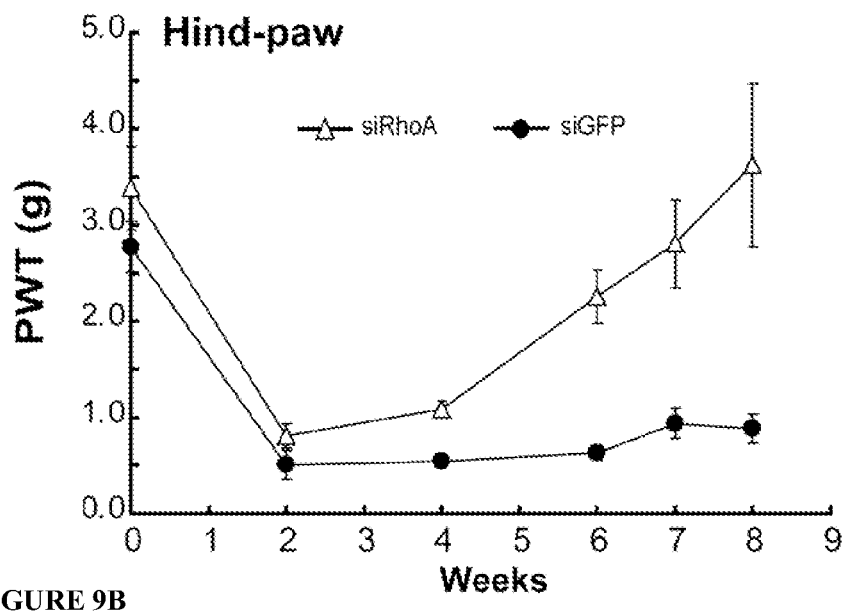
FIGS. 9A-9B. Effects on allodynia of lumbar administration of siRhoA after SCI.
Figure 9B:
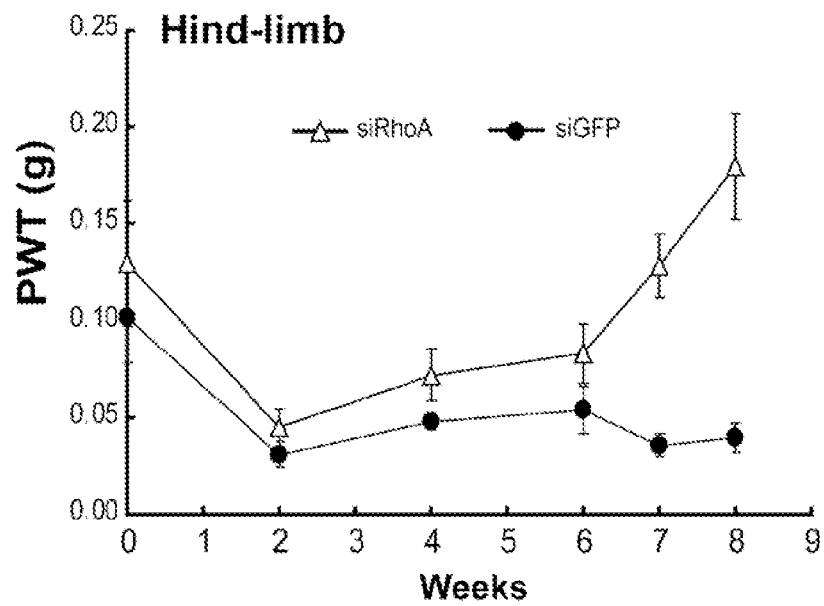
Figure 10:
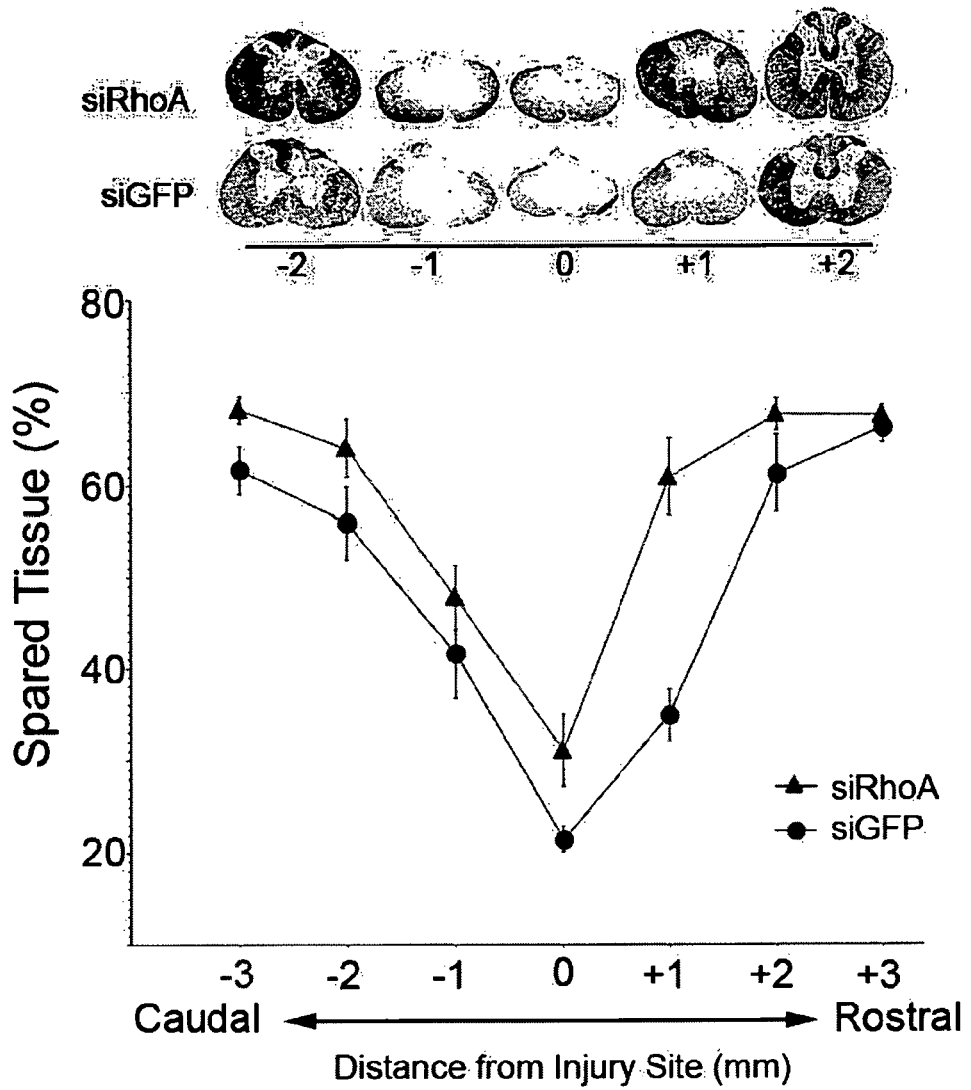
FIG. 10. Measurement of tissue sparing in the spinal cord after SCI and treatment with siRNA. Eight weeks after 12.5 mm contusion with MASCIS impactor and injection of siRNAs, cross sections from indicated regions of the spinal cord were stained with LFB and the fraction of the total area with superthreshold staining was calculated. The tissues were pooled from two 8-week experiments including 4 of the rats used for testing in FIG. 9. Compared to controls with siGFP (n=8) administered at 24 hours after SCI, the siRhoA group (n=8) showed higher areas of LFB staining; ANOVA, p=0.0006.
Figure 11A:
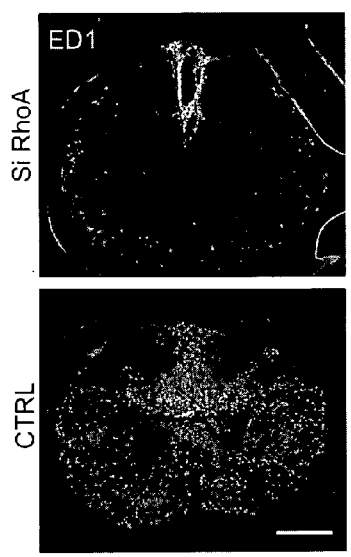
FIGS. 11A-11D. Effects of lumbar administration of siRhoA after SCI on activated macrophages and the dorsal CST. Immunostaining for ED1 (FIGS. 11A, 11B) and PKCγ (FIGS. 11C, 11D) were performed on the sections from the same rats analyzed in FIGS. 9 and 10. ED1 staining, which recognizes activated macrophages and microglia was most robust around the contusion site, was reduced with the siRhoA treatment by comparison to siGFP; sections shown are at 2 mm rostral to the contusion epicenter (+2). Quantitation of ED1-positive areas after thresholding shows that the average area was significantly (ANOVA, p=0.018) lower with siRhoA than with siGFP in the injury epicenter extending until 2 mm rostral. After double immunostaining for PKCγ staining with ED1, areas corresponding to the dorsal CST were outlined and enlarged. After thresholding, the PKCγ areas were measured and the averages are shown (FIG. 11D). The results show significant (p=0.028) preservation of the PKCγ signal with siRhoA group (n=8) by comparison to the siGFP (n=8) over several mm in the regions rostral to the injury epicenter. The sections 8 mm rostral (+8) from the injury site express normal levels of PKCγ immunostaining in regions corresponding to the dorsal CST. There did not appear to be differences in PKCγ immunostaining in lamina II. Scale bars=500 µm.
Figure 11B:
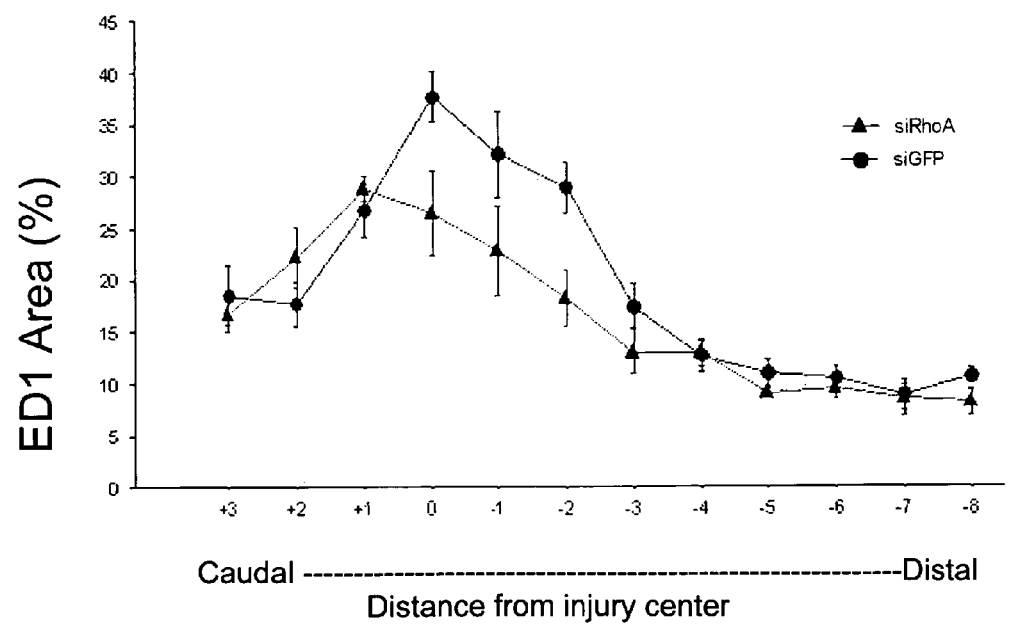
Figure 11C:
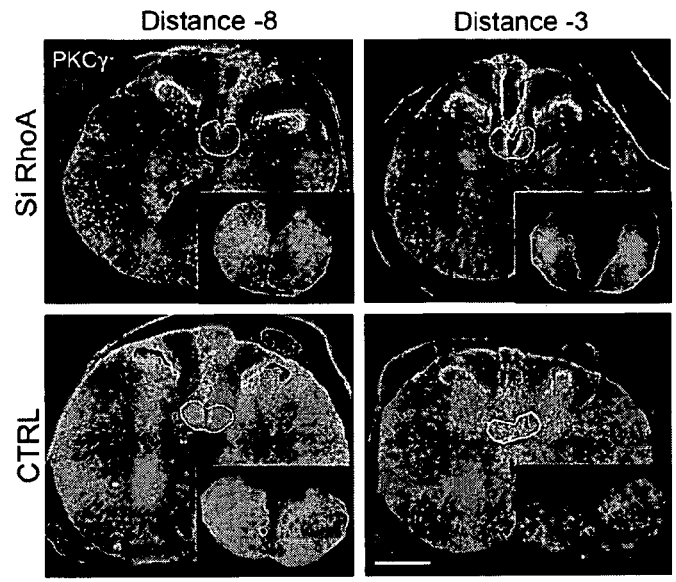
Figure 11D:
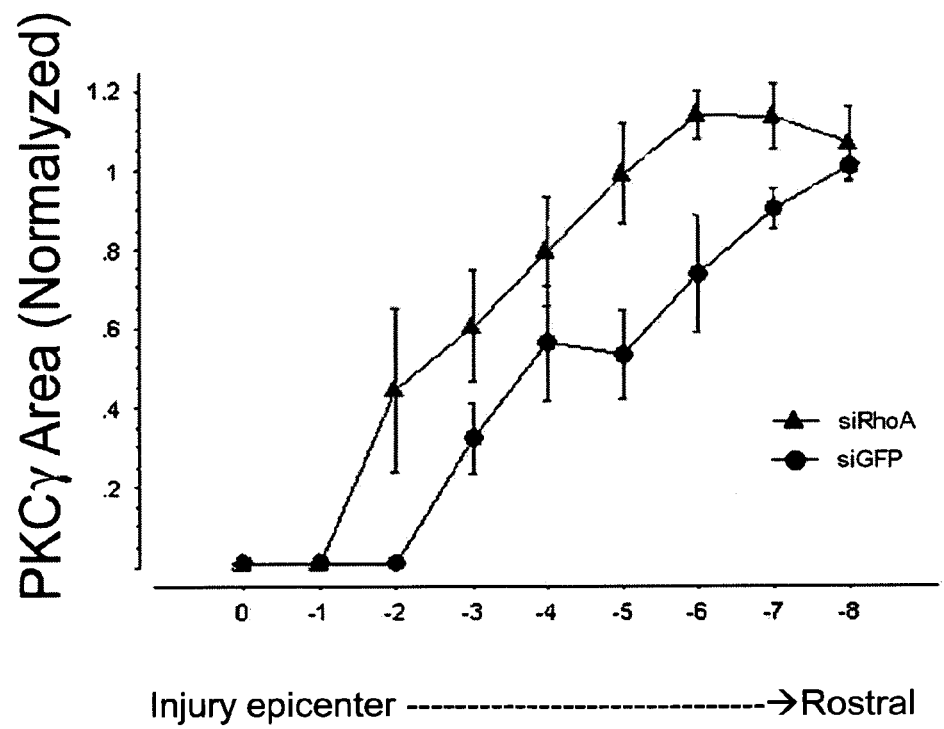

The therapeutic effects of lumbar puncture injection of siRhoA compared to siGFP controls administered one day after contusion injury was measured using BBB scoring. Observations during the first 4 weeks did not show differences in BBB scores but from week 5-8 the siRhoA treatment yielded higher scores that the GFP controls with the maximal difference observed at 8 weeks as shown in FIG. 8. Moreover, in the paw-pressure test with von Frey filaments, rats treated with siRhoA had reduced pain sensitivities by comparison to siGFP controls (FIGS. 9A and 9B). After sacrifice of these rats, white matter sparing measured by fast blue staining was greater with the siRhoA treatment that in the GFP controls (FIG. 10).

Cellular Localization of siRNAs following Intraparenchymal Delivery and SCI

RhoA mRNA expression rises gradually to peak levels at ~1 week following contusion, suggesting that this period represents a window of opportunity to introduce specific siRNAs to inhibit RhoA protein expression (Sung et al., 2003 Brain Res 959(1): 29-38; Conrad et al., 2005 J Comp Neurol 487(2): 166-75; Erschbamer et al., 2005 J Comp Neurol 484 (2): 224-33). To define what types of cells can incorporate siRNA, rat spinal cords at T9-10 by laminectomy were exposed, injected Cy3.5-labeled nuclease-stabilized siRNA and then contused the spinal cord using the MASCIS Impactor with a 12.5 mm weight drop. Confocal microscopic analysis of spinal cords fixed after different survival times revealed widespread Cy3.5 fluorescence with labeling of certain morphologically distinguishable cells including motor neurons, macrophages, white matter axons and endothelial cells (FIG. 1A-1E). Labeling in the large cell bodies of motor neurons and endothelial cells was found at all times up to 2 weeks but label in axonal profiles in the white matter was only detected up to day 3 (FIG. 1F). Six weeks after 1 µg of siRNA was injected into the spinal cord at least some siRNA was still present insofar as ~8 µg was detected in a 0.5 cm segment by Stem-and-Loop qPCR. The fluorescence and biochemical results suggest the siRNA can survive in the contused spinal cord from days to weeks after injection. The results indicate that, when present at the time of contusive injury, the siRNA can be taken up by many of the cells in which RhoA action has been implicated in SCI including neurons, microglia, macrophages and endothelial cells.

Uptake of siRNA in the Spinal Cord Injury Site after Delayed Lumbar Injection

Figure 6A:
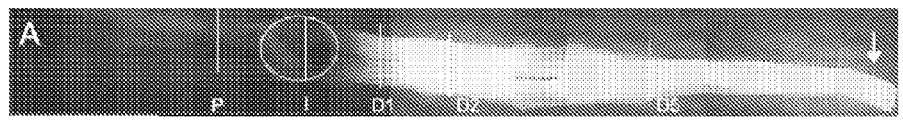
Figure 6A:
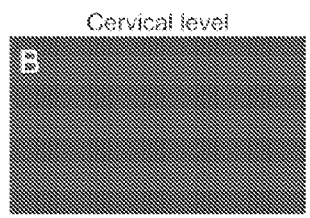
Figure 6A:
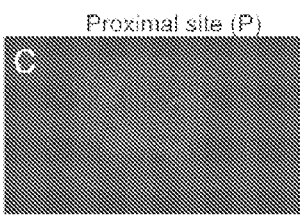
Figure 6A:
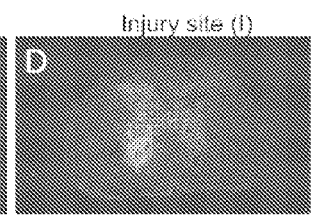
Figure 6A:
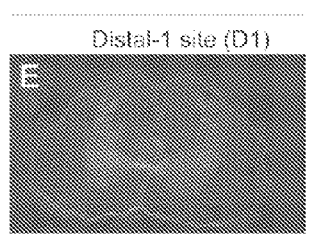
Figure 6A:
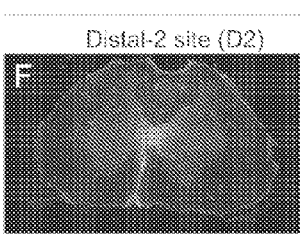
Figure 6A:
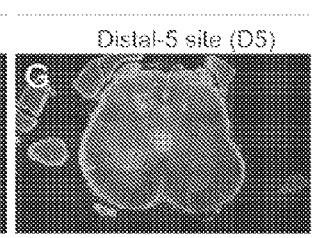

The results described herein indicate that siRNA present in the spinal cord at the time of injury can be taken up into multiple cells, reduce the SCI-induced upregulation of RhoA and has long lasting effects to promote functional recovery. Other routes of administration that could allow more flexibility (including administration at different time points) were examined. Introduction of Cy3.5-labeled siRNAs intranasally (Thorne et al., 2004) yielded some uptake into the brain and spinal cord. Introduction of siRNAs into the CSF was also done intrathecally. A total of 30 µg of Cy3.5-labeled siRNA in a 40 µl volume were injected into the lumbar enlargement at different times (e.g. 24 h) after a 12.5 mm contusion and analyzed the distribution of the fluorescence 24 h later in the freshly dissected spinal cords. Whole mount imaging of the spinal cord revealed widespread Cy3.5 labeling in the spinal cord in the vicinity of the injection site and extending rostrally to the injury site but only weakly beyond it (FIG. 6A). After fixation and cyrosectioning, it was observed that the siRNA penetrated into the white matter and was most robust in the gray matter particularly in the injury site (FIG. 6D). Weaker parenchymal signals were observed in more distal regions but not proximal to the injury site. Comparable fluorescence in the parenchyma was also observed in rats injected 3 days rather than 1 day after contusion. A higher dose of Cy3.5-labeled siRNA (100 µg) did not yield more robust fluorescence in the injury site but a three-fold lower dose (10 µg) yielded much lower signals. The results indicate that at 24 h after delivery at 1 day after SCI, most of the label appeared to be surrounding the spinal cord, with some in the parenchyma and along the central canal. The robust uptake in the spinal cord parenchyma particularly near the injury site may result from increased penetration of Cy3.5-labeled siRNA in regions of injured tissue. When rats injected 24 h after contusion were allowed to survive for 3 days rather than 1 day after injection, fluorescence was found to extend in the parenchyma proximal to the injury site for ~1 cm. The spread in the parenchyma suggests that uptake may continue for several days due to diffusion as well as to circulation in the cerebrospinal fluid. Thus, intrathecal delivery in the lumbar region one day after SCI yielded preferential uptake of siRNA in and around the injury site in the thoracic region compared to the rest of the spinal cord.

Example 2

Further Experimental Results Demonstrating that siRNA Inhibition of RhoA Promotes Functional Recovery from SCI and Prevents Allodynia Material and Methods Animals and spinal cord injury: The experiments were performed using 125 Sprague-Dawley female rats (10-11 weeks old) (Taconic, Germantown, N.Y.). For SCI surgery, rats were anesthetized with 2% isoflurane (IsoFlo, Abbott Lab, North Chicago, Ill.) and the spinal cord was exposed by laminectomy at T9-10 and then contused by dropping a 10.0 g rod on the exposed T11 cord from a height of 12.5 or 25 mm, as described (Constantini and Young, 1994; Hasegawa et al., 2005). Following the contusion and injections when performed, muscles and skin were closed separately. Cefazolin (25 mg/kg) was administered to all rats.

siRNA injection: Injections at the injury site were performed within 30 minutes prior to injury; 1 µg in 1 µl of siRNA was injected at each of three points including the injury epicenter, and 2 mm rostral and caudal to the epicenter (3 µl total) (Hasegawa et al., 2005). Each injection was conducted slowly during a period of ~10 min at a depth of ~1 mm using a sterile 5-µl Hamilton syringe. For lumbar puncture, anesthetized rats were placed on an operating surface that flexed their backs and raised the lumbar region. A ~1 cm longitudinal incision was made over the L3-5 spinal processes, and the skin was retracted. A 30-gauge needle was advanced into the spinal canal at L3-4 or L4-5 to administer 40 µl into the intrathecal space using a 100 µl Hamilton syringe. Proper placement of the needle in the lumbar intrathecal space was indicated by a feeling of "give" at the time of entry and a tail flick (Lepore et al., 2005). To determine whether this method reverses cerebrospinal fluid (CSF) flow up to the region of the injury site, 40 µl of Evans Blue dye were injected in the lumbar enlargement and the appearance of the dye in exposed T9-10 spinally laminectomized rats within seconds after injection confirmed flow across the injury site.

Total cellular RNA preparation and Q-RT-PCR: To isolate RNAs, animals were injected with 100 mg/kg pentobarbital and then perfused with cold PBS. Spinal columns were quickly removed and frozen on dry ice powder. A 5-mm spinal cord segment centered at injury (I) epicenter was dissected along with adjacent 5-mm proximal and distal segments as well as a segment at thoracic level 1 (T1) (Chang et al., 2009). In some experiments the I segments were bisected at the midline yielding two pieces of tissue representing the same region of the spinal cord and separate extractions for RNA and protein enabled comparison of results from the paired tissues. For RNA, tissues were homogenized with a polytron homogenizer (Kinematica Inc.) and RNA was prepared following the Qiagen RNeasy Plus Mini protocol (Qiagen, Valencia, Calif.). RNA was quantitated using a Nanodrop spectrophotometer (Thermo Scientific Inc.) and 1 µg of total RNA was used for first-strand cDNA with SuperScript II reverse transcriptase (Invitrogen, Carlsbad, Calif.) primed by random hexamers. PCR reactions were performed on 40 ng of cDNA using 1 mM of primers and SYBR Green master mix (Applied Biosystems, Foster City, Calif.) in 20 μl reactions using Applied Biosystems 7500 Fast machine. The expression value of each gene was normalized to the amount of GAPDH cDNA to calculate the relative amount of RNA present in each sample.

RhoA protein detection and quantitation by ELISA: Spinal cord segments (5 mm) were homogenized using a Teflon pestle in 150 ul of RIPA buffer (Sigma R0278) containing 3 ul of 50× complete protease inhibitor cocktail (Roche). Protein concentrations were determined using the Micro BCA Protein Assay Kit (Pierce) according to the manufactures recommended 96-well plate protocol. RhoA protein was detected by immunoblotting with anti-RhoA monoclonal antibody ARH03 (Cytoskeleton Inc.) using 20 μg loads of protein. To avoid problems in normalizing across different immunoblots when many samples were analyzed, ELISA that is more sensitive and can accommodate more samples per plate was used. ELISA 96-well plates (Nunc MaxiSorp) were coated with 100 ul of carbonatebicarbonate buffer containing proteins at 80 μg/ml or diluted RhoA as a standard (Cytoskeleton Inc.) incubated overnight at 4° C., and the next day, RhoA was detected using anti-RhoA monoclonal antibody ARH03 according to the manufacturers suggested protocol in the Express Elisa Kit (GenScript). Colorimetric intensities at 450 nm were measured in a Biotek microplate reader and the results were analyzed with Gen5 software (Biotek) to determine concentrations of RhoA in each experimental sample from the standard curve for RhoA.

Tissue processing and staining: Anesthetized animals were perfused intracardially with saline solution followed by 4% paraformaldehyde. Spinal cords were removed with injury epicenter marked and post-fixed 4-5 h in the same fixative, cryoprotected, embedded for frozen sectioning and cut at 20 μm on a cryostat (Hacker-Bright). Cy3.5 labeled siRNA was detected in freshly isolated spinal cord with a Zeiss Stemi SV11 microscope to determine gross distributions. Spinal cords were then fixed in 4% paraformaldehyde and cryosectioned. LFB staining and other procedures were performed as described (Hasegawa et al., 2005). For immunostaining, sections were blocked with 10% normal goat serum/0.3% Triton X-100 in PBS for 2 h at and incubated overnight at 4° C. with primary antibodies. Staining with rabbit protein kinase C-γ (PKCγ) (1:200) and mouse ED1 (1:300) (Serotec, Raleigh, N.C.) were performed on the same sections following antigen retrieval with proteinase K (Dako) for 4 min at 25° C. Sections were washed with PBS and incubated with secondary anti-rabbit Alexa 488 or anti-mouse Alexa 568 at 1:400 for 1 h at room temperature. After washing, sections were mounted with Aqua-Mount (Lerner Lab). Images were captured using a Zeiss 510 confocal laser scanning microscope (LSM) or a Zeiss Automated Cell scan System for Axiovert 200 M on groups of sections that were stained at the same time. Staining with Serotonin rabbit 5-HT (1:1000) (ImmunoStar) was performed using the same procedure without antigen retrieval and with anti rabbit Alexa 568 (1:200) as secondary antibody.

Quantitation for histology: Quantitation of LFB staining was used to analyze tissue sparing. All coronal sections for the analysis were stained for LFB at the same time to ensure uniform color development and then scanned with a Film Scanner LS-8000 ED (Nikon, Japan) at 4000 dpi resolution. The color images were converted to gray scale and individual sections were outlined in Photoshop, and NIH Image J was used to obtain the total area pixels for each section. A constant threshold was used to obtain super-threshold pixels of LFB staining and the resulting areas were measured. Spared tissue is defined as the super-threshold area divided by the total area outlined in each section. Images from each spinal cord were measured at 1 mm intervals over 10 mm of the spinal cord centered on the injury epicenter. In nearly all cases the position with minimal spared tissue corresponded to the designated injury epicenter and when it did not it was redefined as the 0 location. Averages of spared tissue were then calculated and plotted as a function of location (FIG. 11). For ED1 staining, 11 coronal sections at 1 mm intervals were chosen from each animal for quantitation. Tiled images encompassing entire coronal sections at each location were taken with a 20× objective lens (N.A.=0.75) on an Axiovert 200M fluorescence microscope (Zeiss) and analyzed with Zeiss LSM histogram software. A constant threshold was applied to all sections and the super-threshold area for each was divided by the total area outlined to obtain the percent ED1+. The CST is located at the midline above the central canal and PKCγ staining in this region was outlined (see FIG. 12C) and extracted for quantitation. Sections 8 mm rostral from the injury site appeared normal and expressed comparable levels of PKCγ both in regions corresponding to lamina II and the dorsal CST. Therefore, the average of all the super-threshold areas at 8 mm rostral to the injury was used for normalization of the other sections. Super-threshold areas of each CST extracted region were obtained after excluding areas of autofluorescence due to macrophages (see inserts FIG. 12C) and then normalized. All quantitative analyses were performed by investigators blinded to the treatment groups.

Behavioral analyses: Locomotor recovery was assessed weekly using the 21-point BBB score (Basso et al., 1996. J. Neurotrauma 12: 1-21; Basso et al., 1996. Exp Neurol 139(2): 244-56; Hasegawa et al., 2005. Exp Neurol 193: 394-410) by BBB scoring teams that were unaware of experimental treatments (Hasegawa et al., 2005. Exp Neurol 193: 394-410). For allodynia, hindpaw withdrawal thresholds were determined using a series of von Frey filaments (Stoelting, Ill.) with calibrated bending forces ranging from 0.6 to 18 g (Dixon, 1980. Annu Rev Pharmacol Toxicol 20: 441-62; Hains and Waxman, 2006. J Neurosci 26(16): 4308-17). Rats were placed individually in wire mesh-bottom cages, and allowed to acclimate for 30 min before von Frey filaments were applied to the central region of the plantar surface of ventral hindpaws in ascending order of force. Testing was performed only when the rat was stationary and standing on all four paws. A withdrawal response was considered valid only if the hindpaw lifted completely from the mesh-bottom. When a withdrawal response was established for a given animal, a von Frey filament with the next lower force was used to retest, until no response occurred. A trial consisted of applying von Frey filaments five times to each hindpaw. The hindpaw withdrawal threshold was defined as the lowest force that caused at least three withdrawals out of five consecutive applications. Thresholds were determined first for the left hindpaw and then for the right hindpaw of the same rat after 5 min and average thresholds were calculated (Dixon, 1980 Ann Rev Pharmacol Toxicol 20:441-462; Hains and Waxman, 2006 J Neurosci 26:4308-4317). The lateral hindpaw test also used von Frey filaments to probe lateral hindpaw withdrawal and thresholds were calculated as above.

Figure 3C:
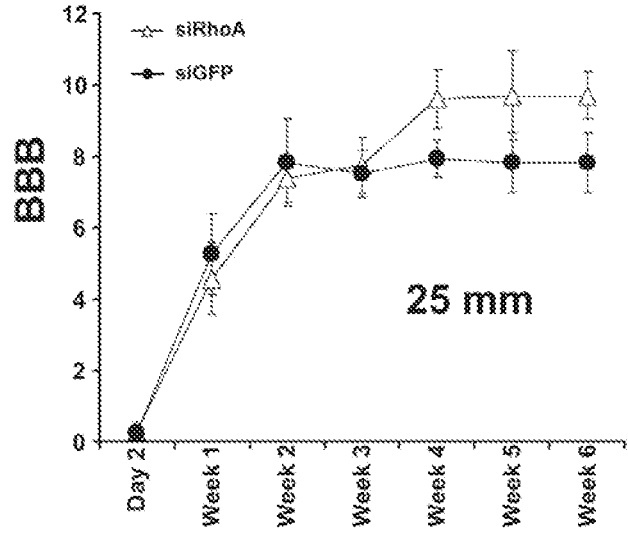

Results siRhoA Inhibits Induction of RhoA Protein after SCI and Promotes Recovery of Hindlimb Walking A panel of siRNAs designed to target rat RhoA sequences were tested for knockdown of RhoA mRNA by qPCR. The most potent siRNA reduced RhoA mRNA levels by >80% at 5 nM in rat REF52 cells and it was even more effective in knocking down RhoA expression in human HeLa cells (FIG. 2A). The siRNA showed no evidence of degradation after incubation at 37° C. for 10 h in rat cerebrospinal fluid suggesting that it should be stable in vivo for at least hours and perhaps for days (FIG. 2B). To analyze the ability of this siRNA to alter RhoA protein levels after SCI, siRhoA or siGFP as a negative control were injected into the vicinity of the injury site 30 minutes prior to contusion. After one week, 5 mm segments of spinal cord tissues were extracted with RIPA buffer and equivalent amounts of protein were resolved on SDS gels and immunblotted with antibodies to RhoA. The highest levels of RhoA immunoreactivity were detected in the 5 mm segments centered on the injury site in rats injected with siGFP or in uninjected spinal cords. Lower levels of RhoA immunoreactivity were observed in most injured spinal cords injected with siRhoA (FIG. 3A). The results indicate that delivery of siRhoA to the spinal cord at the time of injury reduced upregulation of RhoA protein at one week. To test whether knockdown of RhoA after SCI affects functional recovery, a similar experiment with locomotor BBB analysis for 6 weeks following intraspinal injections of siRhoA or siGFP as a control was carried out. Following a 12.5 contusion at thoracic levels T9-10, siGFP injected animals showed a typical pattern of recovery in BBB scores reaching a plateau of ~12 (Basso et al., 1996), whereas the group injected with siRhoA reached a higher plateau of ~15 (FIG. 3B). The improvement of BBB walking scores appeared at the earliest times tested, suggesting that the siRhoA effect may involve protective mechanisms. Another two groups of rats were injected with the same doses of siRNAs and tested for recovery after a more severe 25 mm MASCIS contusion. The average BBB score in the siGFP treated group plateaued at ~8 somewhat lower than expected. Without wishing to be bound to theory, the injections prior to the more severe contusion may exacerbate the injury. The average BBB score of the siRhoA treated group was higher but the differences were not statistically significant (FIG. 3C). The results suggest that siRhoA injection into the spinal cord just prior to injury improves recovery significantly after a 12.5 mm contusion and showed a beneficial trend with the more severe 25 mm contusion.

Inhibition of SCI-induced RhoA Expression 3 Days after Lumbar Injection of siRNA A dose of 30 μg of Cy3.5-labeled siRNA was the minimal dose that yielded robust uptake into the injury site following lumbar injection, and this dose was tested for knockdown activity. The ability of siRNAs to inhibit levels of RhoA mRNA and protein after SCI was measured by quantitative RT-PCR and ELISA, respectively. One day after contusion, siRNAs were injected via lumbar puncture and three days later 5 mm segments centered on SCI sites were dissected and then bisected along the midline. RNA extracted from one half of the bisected tissues was analyzed by RT-PCR for RhoA. The relative levels of RhoA mRNA in the T9-10 injury site at 4 days after 12.5 mm contusion were 1.96+/−0.08 times the levels found in the first thoracic segment (T1) in the SCI only group (FIG. 7A). Lumbar injection of 30 μg of siRhoA reduced the SCI-induced RhoA mRNA to 1.41+/−0.12 times T1 levels but injection of control siGFP did not inhibit the relative levels of RhoA mRNA significantly (FIG. 7A). A higher dose of 100 μg siRhoA inhibited RhoA mRNA significantly to 1.2+/−0.10 times T1 levels (FIG. 7A). Relative levels of RhoA protein were measured by ELISA of protein extracts prepared from the same rats analyzed above using the second half of the SCI samples obtained after bisecting the spinal cords. The 100 μg dose of siRhoA inhibited the relative levels of RhoA protein significantly to 0.65+/−0.04 by comparison to control injuries injected with siGFP (0.96+/−0.06) or without injection (1.00+/−0.04), and the 30 μg dose showed a similar trend reducing the relative levels to 0.71+/−0.08 (FIG. 7B). The results indicate that lumbar injection of siRhoA one day after SCI reduced RhoA mRNA and protein levels after 3 days using siRNA doses that exhibited robust uptake in the injured spinal cord.

Lumbar Injection of siRhoA Prevented Allodynia in SCI Rats

The therapeutic effects of lumbar puncture injection of 100 μg doses of siRhoA compared to siGFP controls administered one day after 12.5 mm MASCIS contusion injury were measured using weekly BBB scoring. In a first experiment using 4 rats per group there was no significant difference in the BBB scores but there was a slight trend towards improvement with the siRhoA. Tactile hypersensitivity with a hindpaw-pressure test using von Frey filaments (Hams and Waxman, 2006. J Neurosci 26(16): 4308-17) was measured and found to be decreased at 6-8 weeks in the siRhoA group. A second experiment using larger groups of 7 rats per treatment was also performed, and significant differences between siRhoA and siGFP in allodynia but not in locomotion were found. Uninjured rats were relatively insensitive with a pressure withdrawal threshold (PWT) of ~3 g, whereas spinally contused rats exhibited increased sensitivity (<1 g) by 2 weeks that persisted throughout the remaining survival period until week 8 (FIG. 9A). No evidence of increased sensitivity with siRhoA treatment by comparison to siGFP controls was observed. Rather, rats treated with siRhoA had reduced tactile sensitivities by week 6 that continued to improve to pre-injury levels by week 8 (FIG. 9A). A similar time course of increased sensitivity after SCI was also observed with a lateral paw test (FIG. 9B) that is not complicated by the reflex reaction that can occur with the glabrous paw test. In both tests, the thresholds for withdrawal at 8 weeks were significantly higher after injection of 100 μg of siRhoA than with control siGFP treatment. The combined results indicate that siRhoA inhibits allodynia that typically develops after contusive SCI. Provided herein is a method of preventing allodynia in a subject comprising administering to the subject by lumbar injection a siRNA compound directed to a target gene associated with allodynia in an amount and over a period of time effective to prevent allodynia in the subject.

siRhoA Treatment Promoted White Matter Sparing

White matter sparing was observed in a SCI study with an inhibitor of RhoA function (Lord-Fontaine et al., 2008. J Neurotrauma 25(11): 1309-22). To analyze the effect of siRNA injection on white matter preservation in the groups of contused rats described above, the tissues after the 8-week survival period were perfusion fixed and coronal spinal cord sections were stained with LFB. In nearly all spinal cords, the preserved white matter was at a minimum at the center of the injury site with increasing LFB staining in more rostral and caudal regions (FIG. 10). Measurement of the percent white matter spared at 1 mm intervals rostral and caudal from the center of the injury site yielded higher average values with the siRhoA than with the control siGFP treatment at the center of the injury site and in surrounding regions. Preservation was most robust with the siRhoA treatment 1 mm rostral to the injury site (FIG. 10). The results indicate that reducing RhoA levels improves white matter sparing after spinal cord contusion. In one embodiment provided is a method to promote sparing of white matter in a subject having a spinal cord injury comprising administering to the subject by lumbar injection a siRNA compound directed to a target gene in an amount and over a period of time effective to spare white matter in the subject.

siRhoA Treatment Decreased ED1 Staining

The loss of myelin following spinal cord injury has been attributed at least in part to robust and prolonged actions of activated macrophages (Blight, 1992; Kigerl et al., 2009). Immunostaining with ED1 on the same groups of rats analyzed above for myelin sparing suggested that there were fewer activated macrophages in the siRhoA treated rats than in the controls (FIG. 12A). Measurement of the ED1-positive areas in the control siGFP treated groups showed a peak at the injury epicenter with decreasing signals in rostral and caudal regions as described previously at 6 weeks after spinal cord injury (Fleming et al., 2009. J Neurosurg Spine 11(5): 575-87). Lower levels of ED1-positive areas were detected in the siRhoA treated groups in the injury site as well as in rostral but not in caudal spinal cord regions (FIG. 12B). The region in which siRhoA treatment was most effective in reducing levels of ED1-positive cells (0 to +2 mm) corresponds to the region where white matter sparing was most robust (FIG. 10). The results indicate that treatment with siRNA against RhoA reduced levels of activated macrophages after 8 weeks at the injury site and in rostral regions where oligodendrocyte death and myelin loss occur.

siRhoA Treatment Increased PKCγ Fibers

After spinal cord contusion many fiber tracts are damaged and surviving axons retract away from the extended injury site. The corticospinal tract (CST) located in dorsal-medial spinal cord can be identified by PKCγ staining (Bradbury et al., 2002. Nature. 2002 Apr. 11;416(6881):636-40), and it is particularly sensitive to SCI and shows minimal regeneration into the injury site after contusion (Demediuk et al., 1990; Hill et al., 2001; Steward et al., 2003). With control siRNA treatment after contusion the PKCγ+ CST was relatively intact at 8 mm rostral to the injury site but staining diminished dramatically at 3 mm rostral (FIG. 12C). Quantitative analysis in coronal sections showed complete loss of PKCγ staining in the siGFP treated group at 2 mm rostral to the injury site with increasing staining progressively in more rostral regions up to 8 mm from the injury site (FIG. 12D). In contrast, rats treated with siRhoA had significantly more staining for PKCγ than the control siRNA at 2 mm rostral to the injury site and at each location more rostral up to +8 mm where they did not differ significantly (FIG. 12D). The results suggest that inhibition of RhoA induction after SCI yielded more CST fibers.

siRhoA Treatment Promoted Serotonergic Fiber Growth

In previous studies, increased staining for the raphe tract has been associated with reduced allodynia (Ramer et al., 2004. J Neurosci. 2004. 24(48):10796-805.) and more recently serotonin function has been confirmed (Wei et al. 2010. J Neurosci. 30(25):8624-36.). Therefore the extent of serotonergic fiber staining caudal to the contusion site was measured. Even at low magnification (FIG. 12), there were obvious differences between siGFP controls and siRhoA injected spinal cords with more intense staining in the latter. Quantitative analysis of serotonin+ fiber immunostaining performed on higher magnification confocal images in eight regions to detect fibers at 12 mm caudal to the contusion site showed significantly longer lengths in siRhoA treated rats by comparison to siGFP controls (FIG. 12). These results indicate a significant improvement in serotonergic fiber growth with the siRhoA treatment following SCI in the rat.

Example 3 siRhoA and siTLR4 can Prevent and Treat Allodynia

Therapeutic activity of siRNA directed to RhoA mRNA (SEQ ID NO:1) or TLR4 mRNA (SEQ ID NO:2) in the Spinal Nerve Ligation Model (Chung) in rats The Chung (Kim and Chung, 1992. Pain. 1992 September; 50(3):355-63.) rat model duplicates the symptoms of human patients with causalgia, or burning pain due to injury of a peripheral nerve. The Chung procedure produces a long-lasting hyperalgesia to noxious heat and mechanical allodynia of the affected foot. Rats with spinal nerve ligation (SNL) are useful for identifying active dsRNA compounds for use in alleviating neuropathic pain.

Alleviation Of Neuropathic Pain in Chung Model Rats

The surgical procedure previously described by Kim and Chung, 1992, was performed on male Sprague-Dawley rats weighing 190 to 2100 grams to induce an allodynic state. Animals were acclimated for at least 5 days. During acclimation and throughout the entire study duration, animals were housed within a limited access rodent facility and kept in groups with a maximum of 5 rats per cage. Animals are provided ad libitum with a commercial rodent diet and have free access to drinking water. Automatically controlled environmental conditions were monitored daily. Animals were given a unique animal identification tail mark.

During the acclimation period, animals will be randomly assigned to experimental groups. Each dosing group will be kept in separate cages to avoid cross-contamination which can occur through consumption of fecal matter. 2-3 animals will be housed per cage. A total of 108 rats were divided into 9 test groups, according to Table B, hereinbelow. Briefly, the rats were anesthetized with ketamine/xylazine sodium and subsequently, the left L-5 and L-6 spinal nerves were isolated adjacent to the vertebral column and ligated. The muscle is sutured and the skin closed with a clamp. Seven days day postoperative recovery period, the animals were tested for inclusion into the study. Pain is detected when one or more of the criteria below are met:

Licking of the operated paw, accompanied by gentle biting or pulling nails with the mouth; lifting the operated leg in the air; bearing weight on the side contralateral to the nerve injury; deformities of the hind paw and abnormal walking; weakness of the left hind paw. The animal has to be able to move it leg to ensure that L4 is intact.

Alzet pump: Animals from groups 1M, 5M, 7M and 9M were implanted subcutaneously with osmotic pumps on the day of surgery. A polyethylene tubing was implanted in the intrathecal space of the spinal cord, ending at level L4 and a cannula was connected to the pump. Pumping rate was 0.5 ul/hr (±0.1 ul/hr).

Figure 13A:
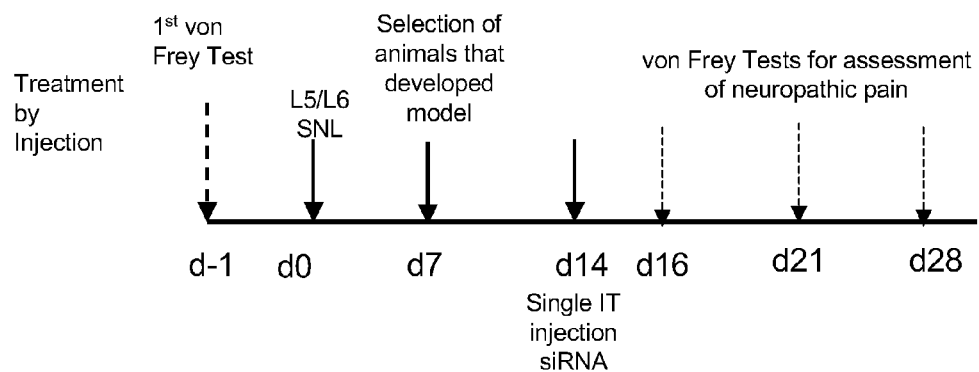
FIGS. 13A-13B. Schemes of the experiments performed to show effect of siRhoA or siTLR4 in treating (FIG. 13A) or preventing (FIG. 13B). SCI-induced allodynia. Results shown in FIGS. 14A-14B.
Figure 13B:
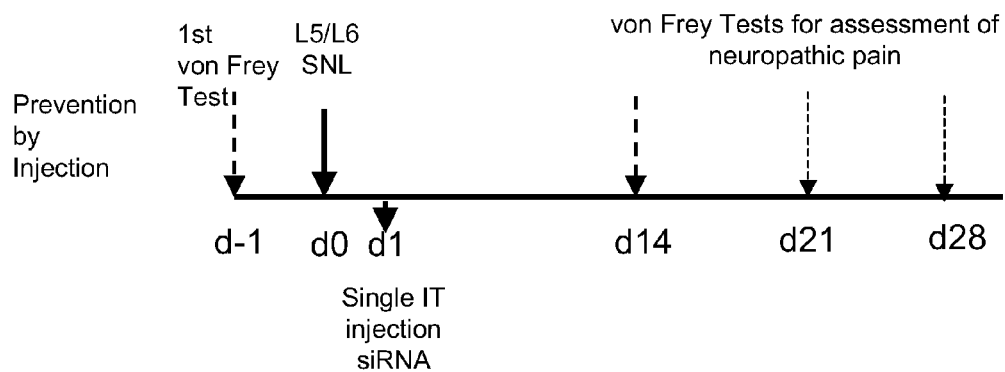

Lumbar injections: Animals from groups 2M, 4M, 6M and 8M were given bolus lumber injections as follows: An intrathecal tube was inserted into the animals IT space at L4-L5 level and the test agents were dosed slowly. Diagrams of the schedules used in the method are provided in FIGS. 13A and 13B. FIG. 13A reproduces treatment of allodynia since animals were administered the test siRNA at day 14 (d14) after SNL. FIG. 13B reproduces prevention of allodynia since animals were administered the test siRNA at day 1 (d1) after SNL.

TABLE B

| Group # | Group Size | Test Item | Route (IT = intrathecal) | Dose active agent (mg/kg) | Volume (ml/kg) | Dosing Regime | Testing regime |
| --- | --- | --- | --- | --- | --- | --- | --- |
| 1M | N = 12 | vehicle 1 (saline) | IT Pump | 0 | 12 ul/day** | from day 0 continuously to day 28 | On study days −1, 14, 21, and 28 |

TABLE B-continued

| Group # | Group Size | Test Item | Route (IT = intrathecal) | Dose active agent (mg/kg) | Volume (ml/kg) | Dosing Regime | Testing regime |
|---|---|---|---|---|---|---|---|
| 2M | N = 12 | vehicle 2 (saline) | IT single lumbar injection | 0 | 40 ul bolus injection (slowly) | Once on day 1, 24 hours after surgery | On study days −1, 14, 16, 21, and 28 |
| 3M | N = 12 | positive control (gabapentin) | IP | 150 mg/kg | 5 ml/kg | Once daily, 2 hours prior to testing on study days 14, 21 and 28 | On study days −1, 14, 21, and 28 |
| 4M | N = 12 | siRhoA (siRNA1) | IT single lumbar injection | 100 ug | 40 ul bolus injection (slowly) | Once on day 1, 24 hours after surgery | On study days −1, 14, 21, and 28 |
| 5M | N = 12 | siRhoA | IT Pump | 20 ug/day (total 280 ug) | 12 ul/day** | from day 0 continuously to day 14* | On study days −1, 14, 21, and 28 |
| 6M | N = 12 | siRhoA | IT single lumbar injection | 100 ug | 40 ul bolus injection (slowly) | once on day 14, post VF testing | On study days −1, 14, 16, 21, and 28 |
| 7M | N = 12 | siRhoA | IT Pump | 20 ug/day (total 280 ug) | 12 ul/day** | from day 14 continuously to day 28* | On study days −1, 14, 21, and 28 |
| 8M | N = 12 | siTLR4 (siRNA2) | IT single lumbar injection | 100 ug | 40 ul bolus injection (slowly) | Once on day 1, 24 hours after surgery | On study days −1, 14, 21, and 28 |
| 9M | N = 12 | siTLR4 | IT Pump | 30 ug/day (total 420 ug) | 12 ul/day** | from day 0 continuously to day 14* | On study days −1, 14, 21, and 28 |

*animal given saline via intrathecal pump implantation on days when not injected with test agent
**pumping rate is 0.5 ul/hr (±0.1 ul/hr) for 14 days The allodynic response to tactile stimulation was assessed using the von Frey apparatus (Touch test). To assess the 50% mechanical threshold for paw withdrawal, a von Frey hair was applied to the hind foot avoiding the foot pad. Each of the von Frey hairs, which are calibrated to bend at increasing log forces, were pressed perpendicularly to the foot with sufficient force to cause slight bending for a duration of approximately six to eight seconds. A positive response was noted if the foot was sharply withdrawn.

Figure 14A:
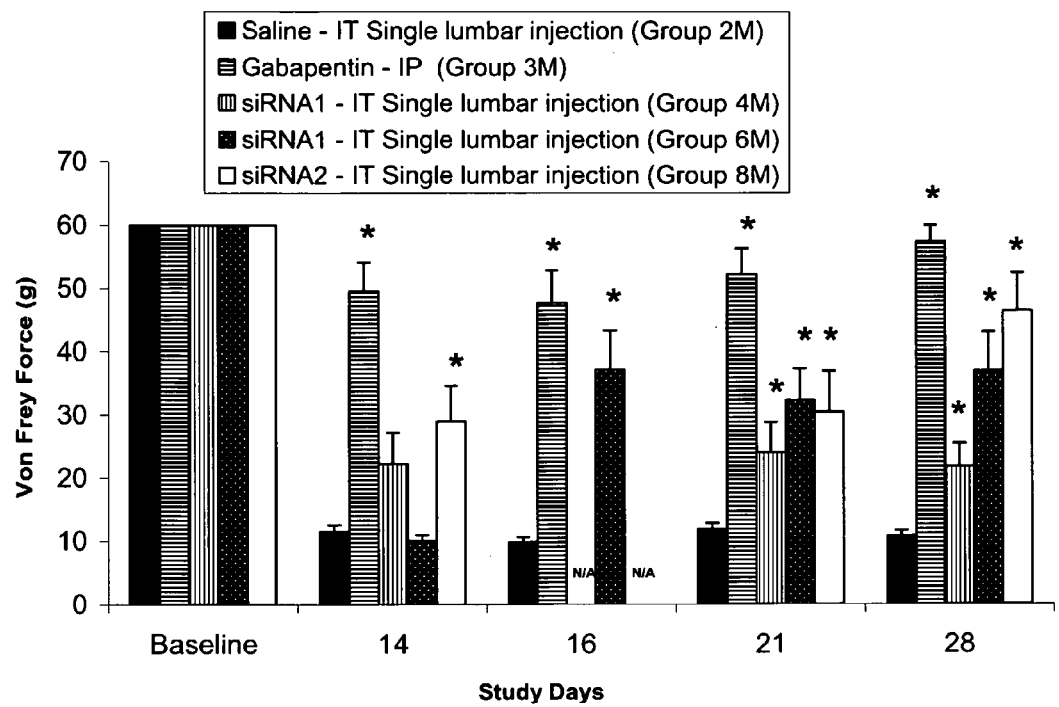
FIGS. 14A-14B. Effects of administration of siRhoA and siTLR4 after SCI on allodynia. (A) (B) One day after 12 5 mm MASCIS contusion siRNAs were injected in lumbar spinal cords and measurements were made of pressure withdrawal threshold (PWT) with von Frye filaments on the glabrous surface of the hindpaw.

FIG. 14A shows results from animal in groups 1M, 3M, 5M, 7M and 9M, i.e. from animals receiving siRhoA (5M and 7M) or siTLR4 (9M) from an implanted minipump continuously from day 0 to day 14 (5M and 9M) or from day 14 to day 28 (7M) compared to animals receiving saline (1M) or gabapentin (3M). A positive effect was obtained in animals treated with siRhoA and siTLR4. The data showed efficacy as early as 14 days post SNL and continued through day 28. Both siRhoA and siTLR4 are effective in treating allodynia.

Figure 14B:
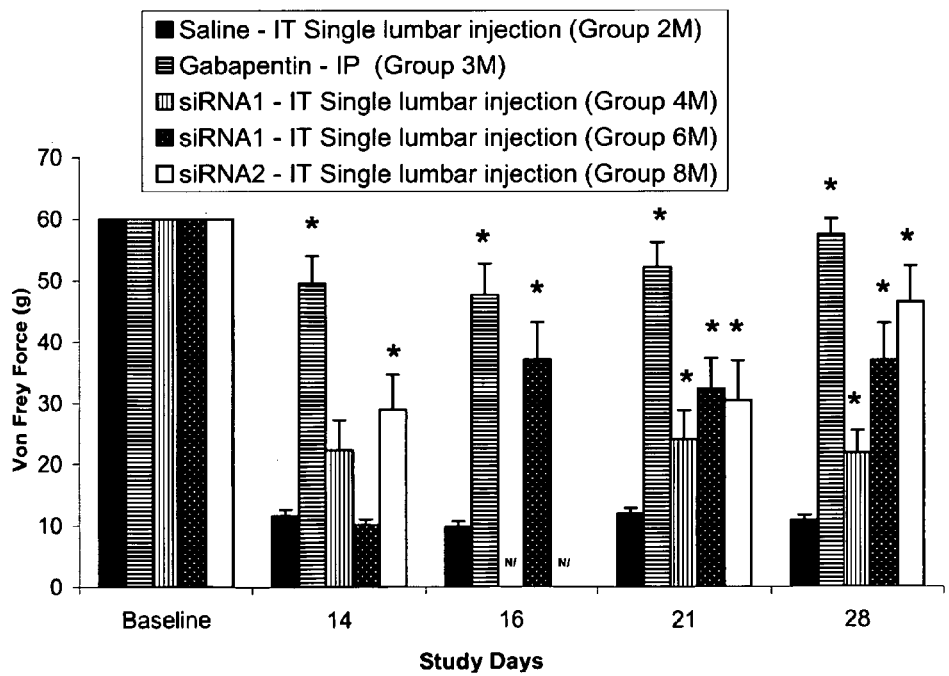

FIG. 14B shows results from animals in groups 2M, 4M, 6M, and 8M, i.e. from animals that received a single lumbar injection of siRhoA (4M) or siTLR4 (8M) one day after SNL and before signs of allodynia appeared or 14 days post SNL (siRhoA, 6M). The data indicate that both siRhoA and siTLR4 are effective in treating and preventing allodynia. The recorded pain levels at 28 days post single lumbar injection show that both siTLR4 and siRhoA were effective in reducing sensitivity to pain.

Table C shows the experimental set up to evaluate the antinociceptive and analgesic activity of siRhoA and siTLR4 in the spinal nerve ligation (SNL) model for neuropathic pain in rats. In all groups the siRNA is administered to the rats via a single bolus lumbar injection. Groups 4M and 5M are designed to further assess siTLR4 in preventing allodynia as compared to control siRNA. Groups 6M and 7M are designed to further assess siRhoA in treating allodynia as compared to control siRNA.

The experiments described above and presented in Tables B and C are useful for testing the effect of double stranded RNA compounds to any one of the target genes set forth in Table A in the treatment or prevention of neuropathic pain.

TABLE C

| Group # | Group Size | Test Item | Administration Route | Dose (mg/kg) | Volume (ml/kg) | Dosing Regime | Testing Regime |
|---|---|---|---|---|---|---|---|
| 1M | N = 5 | Vehicle 1 | IT Single Lumbar injection | 0 | 40 μl bolus injection (slowly) | Once on day 1, 24 hours after surgery | On study day −1, 14, 16, 21 and 28 |
| 2M | N = 5 | Vehicle 2 | IT Single Lumbar injection | 0 | 40 μl bolus injection (slowly) | Once on day 14, post Von Frey testing | On study days −1, 14, 16, 21 and 28 |
| 3M | N = 10 | Positive Control (Gabapentin) | IP | 150 mg/kg | 3 ml/kg | Once daily, 2 hours prior to testing on study days 14, 16, 21 and 28 | On study days −1, 14, 16, 21 and 28 |

TABLE C-continued

| Group # | Group Size | Test Item | Administration Route | Dose (mg/kg) | Volume (ml/kg) | Dosing Regime | Testing Regime |
|---|---|---|---|---|---|---|---|
| 4M | N = 10 | siRNA2 | IT Single Lumbar injection | 100 µg | 40 µl bolus injection (slowly) | Once on day 1, 24 hours after surgery | On study days −1, 14, 16, 21 and 28 |
| 5M | N = 10 | Control siRNA 2 | IT Single Lumbar injection | 100 µg | 40 µl bolus injection (slowly) | Once on day 1, 24 hours after surgery | On study days −1, 14, 16, 21 and 28 |
| 6M | N = 10 | siRNA1 | IT Single Lumbar injection | 100 µg | 40 µl bolus injection (slowly) | Once on day 14, post Von Frey testing | On study days −1, 14, 16, 21 and 28 |
| 7M | N = 10 | Control siRNA 1 | IT Single Lumbar injection | 100 µg | 40 µl bolus injection (slowly) | Once on day 14, post Von Frey testing | On study days −1, 14, 16, 21 and 28 |

Although the present invention has been described in detail, it should be understood that various changes, substitutions and alterations can be made hereto without departing from the spirit and scope of the invention as defined by the appended claims.

---

The invention claimed is:

1. A method of treating neuropathic pain associated with a disease, a disorder or an injury in a subject, comprising administering to the subject a double-stranded RNA compound directed to a RhoA target gene, in an amount effective to treat neuropathic pain in the subject, wherein the double stranded RNA compound is administered to the subject one day or more post-onset of the disease or disorder, or post-injury.

2. The method of claim 1, wherein the double-stranded RNA compound is administered intrathecally.

3. The method of claim 1, wherein the neuropathic pain is associated with spinal cord injury or with peripheral nervous system injury.

4. The method of claim 3, wherein the neuropathic pain is associated with spinal cord injury.

5. The method of claim 1, wherein the spinal cord injury comprises nerve trauma or ischemic injury.

6. The method of claim 1, wherein the neuropathic pain comprises allodynia.

7. The method of claim 1, wherein the double-stranded RNA is chemically modified siRNA.

8. The method of claim 1, wherein the subject is a human.

9. The method of claim 1, wherein the double-stranded RNA is administered to the subject up to 14 days post injury.

10. The method of claim 9, wherein the double-stranded RNA is administered to the subject up to 48 hours post injury.

11. The method of claim 1, wherein the neuropathic pain is associated with a condition selected from the group consisting of traumatic nerve injury, post-ischemia, fibromyalgia, reflex sympathetic dystrophy, complex regional pain syndrome, sciatica, phantom limb pain, diabetic neuropathy, and cancer chemotherapy-induced neuropathic pain.

12. The method of claim 1, wherein the neuropathic pain is caused by a malignant tumor, stroke, postherpetic neuralgia, neuropathy with monoclonal protein, vasculitic neuropathy, neuropathy associated with Guillain-Barre syndrome, neuropathy associated with Fabry's disease, an inflammatory condition, an autoimmune disorder including multiple sclerosis, a toxin, a drug, a hereditary abnormality, a mastectomy, or an amputation.

13. The method of claim 1, wherein the method further comprises administering to the subject a pharmacological agent selected from the group consisting of a non-steroidal anti-inflammatory drug (NSAID), a steroidal anti-inflammatory drug, anti-inflammatory agent, an antibiotic, an anti-viral agent, a free radical scavenger, an anti-cancer agent and a chemotherapeutic agent or any combination thereof, for simultaneous, concurrent, separate or sequential use in treating the subject.

14. The method of claim 1, wherein the double-stranded RNA compound is administered intraspinally.

* * * * *

SEQUENCE LISTING

<160> NUMBER OF SEQ ID NOS: 10

<210> SEQ ID NO 1
<211> LENGTH: 1926
<212> TYPE: RNA
<213> ORGANISM: Homo_sapiens

<400> SEQUENCE: 1

```
guggaugagc ugugagugcg cgcgcgugcg cggggccgcg accugugccg gcucgagccc      60
gcugggcacu cggaggcgcg cacgucguuc cccgcccucc cgccgccgcc cgcccucgcu     120
cucucgcgcu acccucccgc cgcccgcggu ccuccgucgg uucucucguu agaccacggu     180
cuggucuuca gcuacccgcc uucgucuccg aguuugcgac ucgcggaccg gcgucccgg      240 cgcgaagagg cuggacucgg auucguugcc ugagcaaugg cugccauccg gaagaaacug     300
gugauuguug gugauggagc cuguggaaag acaugcuugc ucauagucuu cagcaaggac     360
caguucccag agguguaugu gcccacagug uuugagaacu augguggcaga uaucgaggug     420 gauggaaagc agguagaguu ggcuuugugg gacacagcug ggcaggaaga uuaugaucgc     480
cugaggcccc ucuccuaccc agauaccgau guuauacuga uguguuuuuc caucgacagc     540
ccugauaguu uagaaaacau cccagaaaag uggaccccag aagucaagca uuucugcccc     600
aacgugccca ucauccuggu ugggaauaag aaggaucuuc ggaaugauga gcacacaagg     660
cgggagcuag ccaagaugaa gcaggagccg gugaaaccag aagaaggcag agauauggca     720
aacaggauug gcgcuuuugg guacauggag uguucagcaa agaccaaaga uggagugaga     780
gagguuuuug aaauggcuac gagagcugcu cugcaagcua gacgugggaa gaaaaaaucu     840
gggugccuug ucuugugaaa ccuugcugca agcacagccc uuaugcgguu aauuuugaag     900
ugcuguuuau uaaucuuagu guaugauuac uggccuuuuu cauuuaucua uaauuuaccu     960
aagauuacaa aucagaaguc aucuugcuac caguauuuag aagccaacua ugauuauuaa    1020
cgauguccaa cccgcucugc ccaccagggu ccuuuugaca cugcucuaac agccccuccuc   1080 ugcacuccca ccugacacac caggcgcuaa uucaaggaau uucuuaacuu cuugcuucuu    1140
```

```
ucuagaaaga gaaacaguug guaacuuuug ugaauuaggc uguaacuacu uuauaacuaa    1200
caugaccugc cuauuaucug ucagcugcaa gguacucugg ugagucacca cuucagggcu    1260
uuacuccgua acagauuuug uuggcauagc ucuggggugg gcaguuuuuu gaaaaugggc    1320
ucaaccagaa aagcccaagu ucaugcagcu guggcagagu uacaguucug gguuucaug     1380 uuaguuaccu uauaguuacu guguaauuag ugccacuuaa uguauguuac caaaaauaaa    1440
uauaucuacc ccagacuaga guaguauuu uuuguauaau uggauuuccu aauacuguca     1500
uccucaaaga aaguguauug guuuuuuaaa aaagaaagug uauuuggaaa uaaagucaga    1560
uggaaaauuc auuuuuuaaa uucccguuuu gucacuuuuu cugauaaaag auggccauau    1620
uaccccuuuu cggccccaug uaucucagua ccccauggag cugggcuaag uaaauaggaa    1680
uugguuucac gccugaggca auuagacacu uggaagaug gcauaaccug ucucaccugg     1740
acuuaagcau cuggcucuaa uucacagugc ucuuucucc ucacuguauc cagguucccu     1800
cccagaggag ccaccaguuc ucaugggugg cacucagucu cucuucucuc cagcugacua    1860
aacuuuuuuu cuguaccagu uaauuuuucc aacuacuaau agaauaaagg caguuuucua    1920
aaaaaa                                                              1926

<210> SEQ ID NO 2
<211> LENGTH: 5667
<212> TYPE: RNA
<213> ORGANISM: Homo_sapiens

<400> SEQUENCE: 2
cucuugcugu uucuuuagcc acuggucugc aggcguuuuc uucuucuaac uuccucuccu      60
gugacaaaag agauaacuau uagagaaaca aaaguccaga augcuaaggu ugccgcuuuc     120
acuuccucuc acccuuuagc ccagaacugc uuugaauaca ccaauugcug uggggcggcu     180
cgaggaagag aagacaccag ugccucagaa acugcucggu cagacggug a uagcgagcca    240 cgcauucaca gggccacugc ugcucacaga agcagugagg augaugccag gaugaugucu     300
gccucgcgcc uggcugggac ucugaucccc gccauggccu uccucuccug cgugagacca     360
gaaagcuggg agcccugcgu ggaggugguu ccuaauauua cuuaucaaug cauggagcug     420
aauuucuaca aauccccga caaccucccc uucucaacca gaaccuugga ccugagcuuu     480
aauccccuga ggcauuuagg cagcuauagc uucuucaguu ucccagaacu gcaggugcug     540 gauuuauucca ggugugaaau ccagacaauu gaagauggg cauaucagag ccuaagccac     600
cucucuaccu uauauugac aggaaacccc auccagaguu uagcccuggg agccuuuucu      660
ggacuaucaa guuuacagaa gcugguggcu guggagacaa aucagcauc ucuagagaac      720 uuccccauug acaucucaa aacuuugaaa gaacuuaaug uggcucacaa ucuuauccaa      780
ucuuucaaau uaccugagua uuuuucuaau cugaccaauc uagagcacuu ggaccuuucc     840
agcaacaaga uucaaaguau uuauugcaca gacuugcggg uucuacauca aaugccccua    900
cucaaucucu cuuuagaccu guccugaac ccuugaacu uuauccaacc agguugcauuu     960 aagaaauua ggcuucauaa gcugacuuua agaauaauu uugauaguuu aaauguaaug     1020
aaaacuugua uucaaggucu ggcugguuua gaagccauc guugguucu gggagaauu      1080 agaaaugaag gaaacuugga aaguuugac aaaucugcuc uagagggccu gugcaauuug    1140
accauugaag aauuccgauu agcauacuua gacuacuacc ucgaugauau uauugacuua    1200 uuuaauguu ugcaaaugu uucuucauuu cccuggugua guguacuau gaaaggua      1260 aaagacuuuu cuuauaauuu cggauggcaa cauuuagaau uaguuaacug uaaauuugga     1320
```

```
caguuuccca cauugaaacu caaaucucuc aaaaggcuua cuuucacuuc aacaaaggu    1380 gggaaugcuu uuucagaagu ugaucuacca agccuugagu ucuagaucu caguagaaau    1440 ggcuugaguu ucaaagguug cuguucucaa agugauuuug ggacaaccag ccuaaaguau   1500
uuagaucuga gcuucaaugg uguuauuacc augagucaa acuucuuggg cuuagaacaa    1560
cuagaacauc uggauuucca gcauccaau uugaaacaaa ugagugaguu ucaguauuc    1620 cuaucacuca gaaaccucau uuaccuugac auuucacaua cucacaccag aguugcuuuc   1680
aauggcaucu ucaauggcuu guccagucuc gaagucuuga aaauggcugg caauucuuuc   1740
caggaaaacu uccuuccaga uaucuucaca gagcugagaa acuugaccuu ccuggaccuc   1800
ucucaguguc aacuggagca guugucucca acagcauuua acucacucuc cagucuucag   1860
guacuaaaua ugagccacaa caacuucuuu ucauuggaua cguuuccuua uaaguguacg   1920
aacucccucc agguucuuga uuacagucuc aaucacauaa ugacuuccaa aaaacaggaa   1980
cuacagcauu uuccaaguag ucuagcuuuc uuaaaucuua ucagaauga cuuugcuugu    2040 acuugugaac accagaguuu ccugcaaugg aucaaggacc agaggcagcu cuugguggaa   2100
guugaacgaa uggaaugugc aacaccuuca gauaagcagg gcaugccugu gcugaguuug   2160
aauaucaccu gucagaugaa uaagaccauc auuggugugu cggccucag ugugcuugua    2220 guaucuguug uagcaguucu ggucuauaag uucuauuuuc accgaugcu ucuugcuggc    2280 ugcauaaagu augguagagg ugaaaacauc uaugaugccu uguuaucua cucaagccag    2340 gaugaggacu ggguaaggaa ugagcuagua aagaauuuag aagaaggggu gccuccauuu   2400
cagcucugcc uucacuacag agacuuuauu cccggugugg ccauugcugc caacaucauc    2460
caugaagguu uccauaaaag ccgaaaggug auuguugugg ugcccagca cuucauccag    2520 agccgcuggu guaucuuuga auaugagauu gcucagaccu ggcaguuucu gagcagucgu   2580
gcugguauca ucuucauugu ccugcagaag guggagaaga cccgcucag gcagcaggug    2640 gagcuguacc gccuucucag caggaacacu uaccuggagu gggaggacag uguccugggg   2700
cggcacaucu ucuggagacg acucagaaaa gcccugcugg augguaaauc augggaaucca   2760 gaaggaacag ugggacagg augcaauugg caggaagcaa caucuaucug aagaggaaaa   2820
auaaaaaccu ccugaggcau ucuugccca gcugggucca acacuguuc aguuaauaag     2880 uauuaaaugc ugccacaugu caggccuuau gcuaagggug aguaauucca uggugcacua   2940
gauaugcagg gcugcuaauc ucaaggagcu uccagugcag agggaauaaa ugcuagacua   3000
aaauacagag ucuccaggu gggcauuuca accaacucag ucaaggaacc caugacaaag    3060
aaagucauuu caacucuuac cucaucaagu ugaauaaaga cagagaaaac agaaagagac   3120
auuguucuuu uccugagucu uuugaaugga aauuguauua uguuauagcc aucauaaaac   3180
cauuuuggua guuugacug aacgggugu ucacuuuuc cuuuugauu gaauacaauu      3240 uaaauucuac uugaugacug cagucgucaa ggggcuccug augcaagaug cccuuccau    3300 uuuaagucug ucuccuuaca gagguuaaag ucuaguggcu aauuccaag gaaaccugau    3360 uaacacaugc ucacaaccau ccggucauu cucgagcaug uucuauuuuu aacuaauca    3420 ccccugauau auuuuauuu uuauauaucc aguuucauu uuuuacguc uugccuauaa    3480 gcuaauauca uaaauaaggu uguuaagac gugcuucaaa uaccauauu aaccacuauu    3540 uuucaaggaa guauggaaaa guacacucug ucacuuuguc acucgauguc auuccaaagu   3600
uauugccuac uaaguaauga cugucaugaa agcagcauug aaauaauug uuuaaagggg   3660
```

```
gcacucuuuu aaacgggaag aaaauuuccg cuuccugguc uuaucaugga caauuugggc      3720
uagaggcagg aaggaagugg gaugaccuca ggaggucacc uuuucuugau uccagaaaca      3780
uaugggcuga uaaacccggg gugacccucau gaaaugaguu gcagcagaag uuuauuuuuu    3840
ucagaacaag ugauguuuga uggaccucug aaucucuuua gggagacaca gauggcuggg    3900
aucccucccc uguacccuuc ucacugccag agaacuacg ugugaaggua uucaaggcag      3960
ggaguauaca uugcuguuuc cuguugggca augcuccuug accacauuuu gggaagagug    4020
gauguuauca uugagaaaac aaugugucug gaauuaaugg gguucuuaua agaagguuc     4080
ccagaaaaga auguucaucc agccuccuca gaaacagaac auucaagaaa aggacaauca    4140
ggaugucauc agggaaauga aaauaaaaac cacaaugaga uaucaccuua uaccagguag    4200
aauggcuacu auaaaaaaau gaagugucau caaggauaua gagaaauugg aacccuucuu    4260
cacugcugga gggaauggaa aaugguguag ccguuaugaa aaacaguacg gagguuucuc   4320
aaaaauuaaa aauagaacug cuauaugauc cagcaaucuc acuucuguau auauacccaa    4380
aauaauugaa aucagaauuu caagaaaaua uuuacacucc caugucauu uggcacucu     4440
ucacaaucac uguuuccaaa guuauggaaa caaccccaaau uccauugaa aaauaaaugg    4500
acaagaaaaa ugugcauaua cguacaaugg gauauuauuc agccuaaaaa aagggggaau   4560
ccuguuauuu augacaacau gaauaaaccc ggaggccauu augcuaugua aaaugagcaa   4620
guaacagaaa gacaaauacu gccugauuuc auuuauauga gguucuaaaa uagucaaacu   4680
cauagaagca gagaauagaa caguggcuuc uagggaaaag gaggaaggga gaaaugagga    4740
aauagggagu ugucuaaauug guauaaaaauu uagauaugca agaugaauua gcucuaaaga  4800
ucagcuguau agcagaguuc guauaaugaa caauacugua uuaugcacuu aacauuugu     4860
uaagaggggua ccucucaugu uaagugucu uaccauauac auauacacaa ggaagcuuuu   4920
ggaggugaug gauauauuua uuaccuugau uguggugaug guuugacagg uaugugacua   4980
ugucuaaacu caucaaauug uauacauuaa auauaugcag uuuuauaaua ucaauuaugu   5040
cugaaugaag cuauaaaaaa gaaagacaa caaaauucag uugucaaaac uggaaauaug     5100
accacaguca gaaguguuug uuacugagug uuucagagug uguuuggguu gagcaggucu    5160
agggugauug aacaucccug ggugugucc caugucucau guacuaguga aaguagaugu     5220
gugcauuugu gcacauaucc cuauguaucc cuaucagggc ugugguauu ugaaagugug    5280
uguguccgca ugaucauauc uguauagaag agagugugau uauauuucu gaagaauaca    5340
uccauuugaa auggaugucu auggcuguuu gagaugaguu cucuacucuu ugcuuguac   5400
aguagucucc ccuuauccu uaugcuuggu ggauacguuc uuagaccca aguggaucuc   5460
ugagaccgca gauggauacca aaccucauau augcaauauu uuuccuaua cauaaauacc  5520
uaagauaaag uucaucuucu gaauuaggca caguaagaga uuaacaauaa cuaacaauaa   5580
aauugaauag uuauaauaau auauuguaau aaaaguuaug ugaaugugau cucuuucuuu   5640
cucucucuca aaaaaaaaaa aaaaaaa                                         5667
```

<210> SEQ ID NO 3
<211> LENGTH: 5787
<212> TYPE: RNA
<213> ORGANISM: Artificial Sequence
<220> FEATURE:
<223> OTHER INFORMATION: Chemically synthesized

<400> SEQUENCE: 3

```
cucuugcugu uucuuuagcc acuggucugc aggcguuuuc uucuucuaac uuccucuccu      60
```

```
gugacaaaag agauaacuau uagagaaaca aaaguccaga augcuaaggu ugccgcuuuc      120
acuuccucuc acccuuuagc ccagaacugc uuugaauaca ccaauugcug uggggcggcu      180
cgaggaagag aagacaccag ugccucagaa acugcucggu cagacgguga uagcgagcca      240
cgcauucaca gggccacugc ugcucacaga agcagugagg augaugccag gaugaugucu      300
gccucgcgcc uggcugggac ucugauccca gccauggccu uccucuccug cgugagacca      360
gaaagcuggg agcccugcgu ggagacuugg cccuaaacca cacagaagag cuggcaugaa      420
acccagagcu ucagacuccg gagccucagc ccuucacccc gauuccauu gcuucuugcu       480 aaaugcugcc guuuaucac ggaggugguu ccuaauauua cuuaucaaug cauggagcug       540
aauuucuaca aaucccccga caaccucccc uucucaacca agaaccugga ccugagcuuu      600 aaucccuga ggcauuuagg cagcuauagc uucuucaguu cccagaacu gcaggugcug        660 gauuuaucca ggugugaaau ccagacaauu gaagauggg cauucagag ccuaagccac        720 cucucuaccu uaauauugac aggaaacccc auccagaguu uagcccuggg agccuuuucu      780
ggacuaucaa guuuacagaa gcugguggcu guggagacaa aucagcauc ucuagagaac      840 ucccccauug acaucucaa aacuuugaaa gaacuuaaug uggcucacaa ucuuauccaa      900
ucuuucaaau uaccugagua uuuuucuaau cugaccaauc uagagcacuu ggaccuuucc     960
agcaacaaga uucaaaguau uuauugcaca gacuugcggg uucuacauca aaugcccua      1020 cucaaucucu cuuuagaccu gucccugaac ccaugaacu uuaccaacc aggugcauuu      1080 aaagaaauua ggcuucauaa gcugacuuua agaaauaauu uugauaguuu aaauguaaug     1140
aaaacuugua uucaaggucu ggcugguuua gaaguccauc guuggguucu gggagaauuu     1200
agaaaugaag gaaacuugga aaaguuugac aaaucugcuc uagagggccu gugcaauuug     1260
accauugaag aauuccgauu agcauacuua gacuacuacc ucgaugauau uauugacuua     1320
uuuaauuguu ugacaaaugu uucuucauuu ucccuggug gugugacuau ugaagggua      1380 aaagacuuuu cuuauaauuu cggauggcaa cauuuagaau uaguuaacug uaaauuugga     1440
caguuuccca cauugaaacu caaaucucuc aaaaggcuua cuuucacuuc caacaaaggu     1500
gggaaugcuu uuucagaagu ugaucuacca agccuugagu uucagaucu caguagaaau     1560 ggcuugaguu ucaaagguug cuguucucaa agugauuuug gacaaccag ccuaaaguau     1620 uuagaucuga gcuucaaugg uguuauuacc augaguucaa acuucuuggg cuuagaacaa     1680
cuagaacauc uggauuucca gcauuccaau uugaaacaaa ugagugaguu ucaguauuc      1740 cuaucacuca gaaaccucau uuaccuugac auuucucaua cucacaccag aguugcuuuc     1800
aauggcaucu ucaauggcuu guccagucuc gaagucuuga aaauggcugg caauucuuuc     1860
caggaaaacu uccuuccaga uaucuucaca gagcugagaa acuugaccuu ccuggaccuc     1920
ucucaguguc aacuggagca guugucucca acagcauuua acucacucuc cagucuucag     1980
guacuaaaua ugagccacaa caacuucuuu ucauuggaua cguuuccuua uaagugucug     2040
aacucccucc agguucuuga uuacagucuc aaucacauaa ugacuuccaa aaaacaggaa     2100
cuacagcauu uuccaaguag ucuagcuuuc uuaaaucuua cucagaauga cuuugcuugu     2160
acuugugaac accagaguuu ccugcaaugg aucaaggacc agaggcagcu cuggguggaa     2220
guugaacgaa uggaaugugc aacaccuuca gauaagcagg gcaugccugu gcugaguuug     2280
aauaucaccu gucagaugaa uaagaccauc auuggugugu cgguccucag ugugcuugua     2340
guaucuguug uagcaguucu ggucuauaag uucuauuuuc accugaugcu ucuugcuggc     2400
```

-continued

| | | | | | |
|---|---|---|---|---|---|
| ugcauaaagu | auggu agagg | ugaaaacauc | uaugaugccu | uuguuaucua | cucaagccag | 2460 |
| gaugaggacu | ggguaaggaa | ugagcuaguu | aagaauuuag | aagaaggggu | gccuccauuu | 2520 |
| cagcucugcc | uucacuacag | agacuuuauu | cccggugugg | ccauugcugc | caacaucauc | 2580 |
| caugaagguu | uccauaaaag | ccgaaaggug | auuguugugu | ugucccagca | cuucauccag | 2640 |
| agccgcuggu | guaucuuuga | auaugagauu | gcucagaccu | ggcaguuucu | gagcagucgu | 2700 |
| gcugguauca | ucuucauugu | ccugcagaag | guggagaaga | cccugcucag | gcagcaggug | 2760 |
| gagcuguacc | gccuucucag | caggaacacu | uaccuggagu | gggaggacag | uguccugggg | 2820 |
| cggcacaucu | ucuggagacg | acucagaaaa | gcccugcugg | augguaaauc | auggaaucca | 2880 |
| gaaggaacag | ugggu acagg | augcaauugg | caggaagcaa | caucuaucug | aagaggaaaa | 2940 |
| auaaaaaccu | ccugaggcau | uucuugccca | gcugggucca | acacuuguuc | aguuaauaag | 3000 |
| uauuaaaugc | ugccacaugu | caggccuuau | gcuaagggug | aguaauucca | uggugcacua | 3060 |
| gauaugcagg | gcugcuaauc | ucaaggagcu | uccagugcag | agggaauaaa | ugcuagcua | 3120 |
| aaauacagag | ucuccaggu | gggcauuuca | accaacucag | ucaaggaacc | caugacaaag | 3180 |
| aaagucauuu | caacucuuac | cucaucaagu | ugaauaaaga | cagagaaaac | agaaagagac | 3240 |
| auuguucuuu | uccugagucu | uuugaaugga | aauuguauua | uguuauagcc | aucauaaaac | 3300 |
| cauuuuggua | guuugacug | aacggguugu | ucacuuuuuc | cuuuuugauu | gaaucaauu | 3360 |
| uaaauucuac | uugaugacug | cagucgucaa | ggggcuccug | augcaagaug | ccccuuccau | 3420 |
| uuuaagucug | ucuccuuaca | gagguuaaag | ucuaguggcu | aauuccuaag | gaaaccugau | 3480 |
| uaacacaugc | ucacaaccau | ccuggucauu | ucgagcaug | uucuauuuuu | uaacuaauca | 3540 |
| ccccugauau | auuuuuauuu | uuauauaucc | aguuucauu | uuuuuacguc | uugccuauaa | 3600 |
| gcuaauauca | uaaauaaggu | uguuuaagac | gugcuucaaa | uaccauauu | aaccacuauu | 3660 |
| uuucaaggaa | guauggaaaa | guacacucug | ucacuuuguc | acucgaguguc | auccaaagu | 3720 |
| uauugccuac | uaaguaauga | cugucaugaa | agcagcauug | aaauaauuug | uuuaaagggg | 3780 |
| gcacucuuuu | aaacgggaag | aaaauuuccg | cuuccugguc | uuaucaugga | caauuugggc | 3840 |
| uagaggcagg | aaggaagugg | gaugaccuca | ggagguccac | uuuucuugau | uccagaaaca | 3900 |
| uaugggcuga | uaaacccggg | gugaccucau | gaaaugaguu | gcagcagaag | uuuauuuuuu | 3960 |
| ucagaacaag | ugauguuuga | uggaccucug | aaucucuuua | gggagacaca | gauggcuggg | 4020 |
| aucccucccc | uguacccuuc | ucacugccag | gagaacuacg | ugugaaggua | uucaaggcag | 4080 |
| ggaguauaca | uugcuguuuc | cuguugggca | augcuccuug | accacauuuu | gggaagagug | 4140 |
| gauguuauca | uugagaaaac | aauguguucug | gaauuaaugg | gguucuuaua | aagaagguuc | 4200 |
| ccagaaaaga | auguucaucc | agccuccuca | gaaacagaac | auucaagaaa | aggcaaauca | 4260 |
| ggaugucauc | agggaaauga | aaauaaaaac | cacaaugaga | uaucaccuua | uaccagguag | 4320 |
| aauggcuacu | auaaaaaaau | gaagugucau | caaggauaua | gagaaauugg | aacccuucuu | 4380 |
| cacugcugga | gggaauggaa | aaugguguag | ccguuaugaa | aaacaguacg | gagguuucuc | 4440 |
| aaaaauuaaa | aauagaacug | cuauaugauc | cagcaaucuc | acuucuguau | auauacccaa | 4500 |
| aauaauugaa | aucagaauuu | caagaaaaua | uuuacacucc | caugucauu | ugggcacucu | 4560 |
| ucacaaucac | uguuccaaa | guuauggaaa | caacccaaau | uccauugaa | aaauaaaugg | 4620 |
| acaaagaaaa | ugugcauaua | cguacaaugg | gauauuauuc | agccuaaaaa | aaggggaau | 4680 |
| ccuguuauuu | augacaacau | gaauaaaccc | ggaggcauu | augcuaugua | aaaugagcaa | 4740 |
| guaacagaaa | gacaaauacu | gccugauuuc | auuuauauga | gguucuaaaa | uagucaaacu | 4800 |

```
cauagaagca gagaauagaa cagugguucc uagggaaaag gaggaaggga gaaaugagga      4860
aauagggagu ugucuaauug guauaaaauu auaguaugca agaugaauua gcucuaaaga      4920
ucagcuguau agcagaguuc guauaaugaa caauacugua uuaugcacuu aacauuuugu      4980
uaagagggua ccucucaugu uaaguguucu uaccauauac auauacacaa ggaagcuuuu      5040
ggaggugaug gauauauuua uuaccuugau uguggugaug guuugacagg uaugugacua      5100
ugucuaaacu caucaaauug uauacauuaa auauaugcag uuuauaauaa ucaauuaugu      5160
cugaaugaag cuauaaaaaa gaaaagacaa caaaauucag uugucaaaac uggaaauaug      5220
accacaguca gaagguuuug uuacugagug uuucagagug uguuugguuu gagcaggucu      5280
agggugauug aacaucccug ggugcguuuc caugcucau guacuaguga aaguagaugu       5340
gugcauuugu gcacauaucc cuauguaucc cuaucagggc uguguguauu ugaaagugug      5400
uguguccgca ugaucauauc uguauagaag agagugugau uauauuucuu gaagaauaca      5460
uccauuugaa auggaugucu auggcuguuu gagaugaguu cucuacucuu ugcuuguac      5520 aguagucucc ccuuauccu uaugcuuggu ggauacguuc uuagacccca aguggaucuc      5580
ugagaccgca gaugguacca aaccucauau augcaauauu uuuccuaua cauaaauacc      5640 uaagauaaag uucaucuucu gaauuaggca caguaagaga uuaacaauaa cuaacaauaa      5700
aauugaauag uuauaauaau auauuguaau aaaaguuaug ugaaugugau cucuuucuuu      5760
cucucucuca aaaaaaaaaa aaaaaaa                                         5787

<210> SEQ ID NO 4
<211> LENGTH: 5500
<212> TYPE: RNA
<213> ORGANISM: Artificial Sequence
<220> FEATURE:
<223> OTHER INFORMATION: Chemically synthesized

<400> SEQUENCE: 4
cucuugcugu uucuuuagcc acuggucugc aggcguuuuc uucuucuaac uuccucuccu       60
gugacaaaag agauaacuau uagagaaaca aaaguccaga augcuaaggu ugccgcuuuc      120
acuuccucuc accccuuuag ccagaacugc uuugaauaca ccaauugcug uggggcggcu      180
cgaggaagag aagacaccag ugccucagaa acugcucggu cagacgguga uagcgagcca      240
cgcauucaca gggccacugc ugcucacaga agcagugagg augaugccag gaugaugucu      300
gccucgcgcc uggcugggac ucugauccca gccauggccu uccucuccug cgugagacca      360
gaaagcuggg agcccugcgu ggaggucuga aauccagaca auugaagaug ggcauauca      420 gagccuaagc caccucucua ccuuaauauu gacaggaaac cccauccaga guuuagcccu      480
gggagccuuu ucuggacuau caaguuuaca gaagcugguu gcuguggaga caaaucuagc      540
aucucuagag aacuuccca uuggacaucu caaaacuuug aaagaacuua augugggcuc      600
caaucuuauc caaucuuuca auuaccuga guauuuuucu aaucugacca aucuagagca      660
cuuggaccuu uccagcaaca agauucaaag uauuuauugc acagacuugc ggguucuaca      720
ucaaaugccc cuacucaauc ucucuuuaga ccugucccug aaccuauga acuuuauccca      780 accaggugca uuuaaagaaa uuaggcuuca uaagcugacu uuaagaaaua uuuugauag      840 uuuaaaugua augaaaacuu guauucaagg ucuggcuggu uuagaaguccc aucguuuggu      900 ucugggagaa uuuagaaaug aaggaaacuu ggaaaaguuu gacaaaucug cucuagaggg      960
ccugugcaau uugaccauug aagaauuccg auuagcauac uugacuacu accucgauga     1020
```

-continued

```
uauuauugac uuauuuaauu guuugacaaa uguuucuuca uuuucccugg ugagugugac    1080
uauugaaagg guaaaagacu uuucuuauaa uuucggaugg caacauuuag aauuaguuaa    1140
cuguaaauuu ggacaguuuc ccacauugaa acucaaaucu cucaaaaggc uuacuuucac    1200
uuccaacaaa ggugggaaug cuuuuucaga aguugaucua ccaagccuug aguuucuaga    1260
ucucaguaga aauggcuuga guucaaagg uugcuguucu caaagugauu uagggacaac     1320
cagccuaaag uauuuagauc ugagcuucaa ugguguuauu accaugaguu caaacuucuu    1380
gggcuuagaa caacuagaac aucuggauuu ccagcauucc aauuugaaac aaaugaguga    1440 guuucagua uuccaucac ucagaaaccu cauuuaccuu gacauuucuc auacucacac      1500
cagaguugcu uucaauggca ucuucaaugg cuuguccagu cucgaagucu ugaaaauggc    1560
uggcaauucu uuccaggaaa acuuccuucc agauaucuuc acagagcuga gaaacuugac    1620
cuuccuggac cucucucagu gucaacugga gcaguugucu ccaacagcau uuaacucacu    1680
cuccagucuu cagguacuaa auaugagcca caacaacuuc uuuucauugg aucguuucc    1740 uuauaagugu cugaacuccc uccagguucu ugauuacagu ucaaucaca uaaugacuuc    1800 caaaaaacag gaacuacagc auuuuccaag uagucuagcu uucuuaaauc uuacucagaa    1860
ugacuuugcu uguacuugug aacaccagag uuucccgcaa uggaucaagg accagaggca    1920
gcucuuggug aaguugaac gaauggaaug ugcaacaccu ucagauaagc agggcaugcc     1980
ugugcugagu uugaauauca ccugucagau gaauaagacc aucauggug gucggaccu     2040 caguugcuu uaguaucug uuguagcagu ucggucuau aaguucuauu uucaccugau      2100 gcucuugcu ggcugcauaa aguaugguag agugaaaac aucuaugaug ccuuuguuau     2160
cuacucaagc caggaugagg acugggaag gaaugagcua guaaagaauu uagaagaagg    2220
ggugccucca uuucagcucu gccuucacua cagagacuuu auucccggug uggccauugc    2280
ugccaacauc auccaugaag guuccauaa agccgaaag gugauguug uggugucca     2340 gcacuucauc cagagccgcu ggguauucu ugaauaugag auugcucaga ccuggcaguu    2400
ucugagcagu cgucugguua ucaucuucau ugccugcag aagguggaga agacccugcu    2460
caggcagcag guggagcugu accgccuucu cagcaggaac acuuaccugg aguggagga    2520 caguguccug gggcggcaca cuucuggag acgacucaga aaagcccugc uggaugguaa    2580
aucauggaau ccagaaggaa caguggguac aggaugcaau uggcaggaag caacaucuau    2640
cugaagagga aaauaaaaa ccuccugagg cauuucuugc ccagcugggu ccaacacuug    2700
uucaguuaau aaguauuaaa ugcugccaca ugucaggccu uaugcuaagg gugaguaauu    2760
ccauggugca cuagauaugc agggcugcua aucucaagga gcuuccagug cagagggaau    2820
aaaugcuaga cuaaaauaca gagucuucca gguggcauu ucaaccaacu cagucaagga    2880
acccaugaca aagaaaguca uuucaacucu uaccucauca aguugaauaa agacagagaa    2940
aacagaaaga gacauuguuc uuuuccagag ucuuuugaau ggaaauugua uuauguuaua    3000
gccaucauaa aaccauuuug guaguuuuga cugaacuggg uguucacuuu uuccuuuuug    3060
auugaauaca auuuaaauuc uacuugauga cugcagucgu caaggggcuc cugaugcaag    3120 augcccuuc cauuuuaagu cugucuccuu acagagguua agucuagug gcuaauuccu      3180 aaggaaaccu gauuaacaca ugcucacaac cauccugguc auucucgagc auguucuauu    3240
uuuuaacuaa ucaccccuga uauuuuuua uuuuuauaua uccaguuuuc auuuuuuuac     3300
gucuugccua uaagcuaaua ucauaaauaa gguguuuuaa gacgcuuc aaauauccau      3360 auuaaccacu auuuuucaag gaaguaugga aaaguacacu cugucacuuu gucacucgau    3420
```

```
gucauuccaa aguuauugcc uacuaaguaa ugacugucau gaaagcagca uugaaauaau    3480
uuguuuaaag ggggcacucu uuuaaacggg aagaaaauuu ccgcuuccug gucuuaucau    3540
ggacaauuug ggcuagaggc aggaaggaag ugggaugacc ucaggagguc accuuuucuu    3600
gauuccagaa acauauggc ugauaaaccc ggggugaccu caugaaauga guugcagcag    3660
aaguuuauuu uuuucagaac aagugauguu ugauggaccu cugaaucucu uuagggagac    3720
acagauggcu gggaucccuc cccguaccc uucucacugc caggagaacu acgugugaag    3780
guauucaagg cagggaguau acauugcugu uccuguugg gcaaugcucc uugaccacau    3840
uuugggaaga guggauguua ucauugagaa acaaugugu cuggaauuaa uggggpuucuu    3900 auaaagaagg uucccagaaa agaauguuca uccagccucc ucagaaacag aacauucaag    3960
aaaaggacaa ucaggauguc aucagggaaa ugaaaauaaa aaccacaaug agauaucacc    4020
uuauaccagg uagaauggcu acuauaaaaa aaugaagugu caucaaggau auagagaaau    4080
uggaacccuu cuucacugcu ggagggaaug gaaaaugguc uagccguuau gaaaacagu    4140 acggagguuu ucaaaaaau aaaaauagaa cugcuauaug auccagcaau ucacuucug    4200 uauauauacc caaauaauu gaaucagaa uuucaagaaa auauuuacac ucccauguuc    4260 auugggcac ucuucacaau cacuguuucc aaaguuaugg aaacaaccca aauuccauu    4320 gaaaaauaaa uggacaaaga aaaugugcau auacguacaa ugggauauua uucagccuaa    4380 aaaaagggg aauccuguua uuuaugacaa cauugaauaaa cccggaggcc auuaugcuau    4440
guaaaaugag caaguaacag aaagacaaau acugccugau uucauuuaua ugagguucua    4500
aaauagucaa acucauagaa gcagagaaua gaacagauggu uccuagggaa aaggaggaag    4560
ggagaaauga ggaaauaggg aguugucaaa uugguaaaa auuauagaau gcaagaugaa    4620
uuagcucuaa agaucagcug uauagcagag uucguauaau gaacaauacu guauuuaugca    4680 cuuaacauuu uguuaagagg guaccucuca uguuaagugu ucuuaccaua uacauauaca    4740
caaggaagcu uuuggaggug auggauauau uuauuaccuu gauugguggu augguuugac    4800
agguauguga cuaugucuaa acucaucaaa uguauacau uaauauaug caguuuuaua    4860 auaucaauua ugucugaaug aagcuauaaa aaagaaaaga caacaaaaug cauguguguaa    4920 aacuggaaau augaccacag ucagaagugu uguuacuga guguuucaga gugugguugg    4980
uuugagcagg ucuaggguga uugaacauuc cugggcugu uuccaugucu cauguacuag    5040
ugaaaguaga ugugugcauu ugugcacaua ucccuaugua ucccauuaag ggcugugugu    5100 auugaaagu gugugugucc gcaugaucau aucuguauau aagagagugu gauauauuu    5160 cuugaagaau acauccauuu gaaauggaug ucuauggcug uuugaagauga guucucuacu    5220 cuugugcuug uacaguaguc uccccuuauc ccuuaugcuu gguggauacg uucuuagacc    5280 ccaagguuggau cucugagacc gcagauggua ccaaaccuca uauaugcaau auuuuuuccu    5340 auacauuaaau accauaagaua aaguucaucu ucugaauuag gcacaguaag agauuaacaa    5400
uaacaaacaa uaaaauugaa uaguuauaau aauauauugu aauaaaaguu augugaaugu    5460
gaucucuuuc uuucucucuc ucaaaaaaaa aaaaaaaaaa                          5500
```

<210> SEQ ID NO 5
<211> LENGTH: 19
<212> TYPE: RNA
<213> ORGANISM: Artificial Sequence
<220> FEATURE:
<223> OTHER INFORMATION: Chemically synthesized

```
<400> SEQUENCE: 5
gccacuuaau guauguuac                                                    19

<210> SEQ ID NO 6
<211> LENGTH: 19
<212> TYPE: RNA
<213> ORGANISM: Artificial Sequence
<220> FEATURE:
<223> OTHER INFORMATION: Chemically synthesized

<400> SEQUENCE: 6
guaacauaca uuaaguggc                                                    19

<210> SEQ ID NO 7
<211> LENGTH: 19
<212> TYPE: RNA
<213> ORGANISM: Artificial Sequence
<220> FEATURE:
<223> OTHER INFORMATION: Chemically synthesized

<400> SEQUENCE: 7
gaguucaggu uaacauaua                                                    19

<210> SEQ ID NO 8
<211> LENGTH: 19
<212> TYPE: RNA
<213> ORGANISM: Artificial Sequence
<220> FEATURE:
<223> OTHER INFORMATION: Chemically synthesized

<400> SEQUENCE: 8
uauauguuaa ccugaacuc                                                    19

<210> SEQ ID NO 9
<211> LENGTH: 19
<212> TYPE: RNA
<213> ORGANISM: Artificial Sequence
<220> FEATURE:
<223> OTHER INFORMATION: Chemically synthesized

<400> SEQUENCE: 9
gugccaaccu gaugcagcu                                                    19

<210> SEQ ID NO 10
<211> LENGTH: 19
<212> TYPE: RNA
<213> ORGANISM: Artificial Sequence
<220> FEATURE:
<223> OTHER INFORMATION: Chemically synthesized

<400> SEQUENCE: 10
agcugcauca gguuggcac                                                    19
```